(12) United States Patent
Kemble et al.

(10) Patent No.: US 7,204,990 B1
(45) Date of Patent: Apr. 17, 2007

(54) ATTENUATION OF CYTOMEGALOVIRUS VIRULENCE

(75) Inventors: George Kemble, Saratoga, CA (US); Gregory M. Duke, Redwood City, CA (US); Richard Spaete, Emerald Hills, CA (US)

(73) Assignee: MedImmune Vaccines, Inc., Mountain View, CA (US)

( * ) Notice: Subject to any disclaimer, the term of this patent is extended or adjusted under 35 U.S.C. 154(b) by 12 days.

(21) Appl. No.: 09/724,935

(22) Filed: Nov. 28, 2000

(51) Int. Cl.
*A61K 39/245* (2006.01)
*A61K 39/12* (2006.01)
*C12Q 1/70* (2006.01)

(52) U.S. Cl. .............. 424/230.1; 424/199.1; 435/5

(58) Field of Classification Search ............. 424/199.1, 424/230.1; 435/69.1, 235.1; 536/23.72
See application file for complete search history.

(56) References Cited

U.S. PATENT DOCUMENTS 5,721,354 A * 2/1998 Spaete et al. ............ 536/23.72

OTHER PUBLICATIONS

Plotkin, Apr. 1999, "Vaccination Against Cytomegalovirus, The Changeling Demon," Pediatr Infect Dis J., 18:313-326.
Kemble et al., 1996, "A New Generation of Live, Attenuated Cytomegalovirus (CMV) Vaccine Strains," Interscience Conf. Antimicrob. Agents and Chem, H88.
Kemble et al., 1997, "Derivation of Novel, Recombinant, Live, Attenuated CMV Vaccine Strains," 6th Int. Cytomegalovirus Workshop, A-25(49).
Beisel, 2000, "Cytomegalovirus Vaccine Development," Jordan Reprt, 105-110.
Kemble et al., Jul. 1999, "Development of Live, Attenuated Human Cytomegalovirus Vaccine Candidates," 24th Inter. Herpesvirus Workshop; 13.007.
Spate et al., 1997, Progress in Developing a CMV Vaccine, Virology Seminar; Max-von-Pettenkofer Institute und Genz, Munchen,Germany;1-13.
Spate et al., "Controlling CMV through Vaccination," Mar. 20-22, 1998, Science Symposium; Tucson AZ.
Spate et al., 1998, "Progress in Developing a CMV Vaccine," Virology Seminar; University of California—Irvine.
Kemble et al., Apr. 1999, "Towne/Toledo Vaccine Development," 7th Intl. Cytomegalovirus Workshop, Brighton, U.K.
Kemble et al., 1996, "Genetic Determinanats of CMV Virulence," 21st Herpesvirus Workshop; 315.
Spector et al., Cleavage Maps for Human Cytomegalovirus DNA Strain AD169 for Restriction Endonucleases EcoRI, BglII, and HindIII, 1982, J Virol 42:558-82.
Pande et al., Cloning and Physical Mapping of a Gene Fragment Coding for a 64-kilodation Major Late Antigen of Human Cytomegalovirus, 1984, PNAS 54:817-24.
Cha et al., Human Cytomegalovirus Clincal Isolates Carry at Least 19 Genes Not Found In Laboratory Strains, 1996, J Virol 70:78-83.
Chee et al., Analysis of the Protein-Coding Content of the Sequence of Human Cytomegalovirus Strain AD169, 1990, Curr Top Microbiol Immunol. 154, 125-169.
Mocarski et al., A Deletion Mutant in the Human Cytomegalovirus Gene Encoding IE1-491aa is Replication Defective Due to a Failure in Autoregulation, 1998, PNAS 93:11321-11326.
Cihlar et al., Characterization of Drug Resistance-Associated Mutations in the Human Cytomegalovirus DNA Polymerase Gene by Using Recombinant Mutant Viruses Generated from Overlapping DNA Fragments, 1998, J Virol 72:5927-36.
Haberland et al., Variation Within the Glycoprotein B Gene of Human Cytomegalovirus is Due to Homologous Recombination, 1999, J Gen Virol 80:1495-1500.

* cited by examiner

*Primary Examiner*—Stacy B. Chen
(74) *Attorney, Agent, or Firm*—Lisa Kreppel; Janet Martineau; MedImmune Vaccines, Inc.

(57) ABSTRACT

A method is provided for attenuating a cytomegalovirus comprising functionally disrupting an open reading frame of a Toledo genome region or its homolog and making chimeric CMV virus genomes.

6 Claims, 36 Drawing Sheets

```
         10         20         30         40         50         60
CGCTGTAGGG ATAAATAGTG CGATGGCGTT TGTGGGAGAA CGCAGTAGCG ATGGGTTGCG
GCGACATCCC TATTTATCAC GCTACCGCAA ACACCCTCTT GCGTCATCGC TACCCAACGC
        100         80         90        100        110        120
ACGTGCACGA TCCTTCGTGG CAATGCCAAT GGGGCGTTCC CACGATTATC GTGGCCTGGA
TGCACGTGCT AGGAAGCACC GTTACGGTTA CCCCGCAAGG GTGCTAATAG CACCGGACCT
        130        140        150        160        170        180
TAACATGCGC GGCTTTAGGA ATTTGGTGTT TGGCGGGATC GTCGGCGGAT GTCTCTTCGG
ATTGTACGCG CCGAAATCCT TAAACCACAA ACCGCCCTAG CAGCCGCCTA CAGAGAAGCC
        190        200        210        220        230        240
GACCCGGCAT CGCAGCCGTA GTCGGCTGTT CTGTTTTCAT GATTTTCCTC TGCGCGTATC
CTGGGCCGTA GCGTCGGCAT CAGCCGACAA GACAAAGTA CTAAAGGAG ACGCGCATAG
        250        260        270        280        290        300
TCATCCGTTA CCGGGAATTC TTCAAAGACT CCGTAATCGA CCTCCTTACC TGCCGATGGG
AGTAGGCAAT GGCCCTTAAG AAGTTTCTGA GGCATTAGCT GGAGGAATGG ACGGCTACCC
        310        320        330        340        350        360
TTCGCTACTG CAGCTGCAGC TGTAAGTGCA GCTGCAAATG CATCTCGGGC CCCTGTAGCC
AAGCGATGAC GTCGACGTCG ACATTCACGT CGACGTTTAC GTAGAGCCCG GGGACATCGG
        370        380        390        400        410        420
GCTGCTGTTC AGCGTGTTAC AAGGAGACGA TGATTTACGA CATGGTCCAA TACGGTCATC
CGACGACAAG TCGCACAATG TTCCTCTGCT ACTAAATGCT GTACCAGGTT ATGCCAGTAG
        430        440        450        460        470        480
GACGGCGTCC CGGACACGGC GACGATCCCG ACAGGGTGAT CTGCCGAGATA GTCGAGAGTC
CTGCCGCAGG GCCTGTGCCG CTGCTAGGGC TGTCCCACTA GACGCTCTAT CAGCTCTCAG
        490        500        510        520        530        540
CCCCGGTTTC GGCGCCGACG GTGTCCGTCC CCCCGCCGTC GGAGGAGTCC CACCAGCCCG
GGGGCCAAAG CCGCGGCTGC CACAGGCAGG GGGGCGGCAG CCTCCTCAGG GTGGTCGGGC
        550        560        570        580        590        600
TCATCCCACC GCAGCCGCCA GCACCGACAT CGGAACCCAA ACCGAAGAAA GGTAGGGCGA
AGTAGGGTGG CGTCGGCGGT CGTGGCTGTA GCCTTGGGTT TGGCTTCTTT CCATCCCGCT
        610        620        630        640        650        660
AAGATAAACC GAAGGGTAGA CCGAAAGACA AACCTCCGTG CGAACCGACG GTGAGTTCAC
TTCTATTTGG CTTCCCATCT GGCTTTCTGT TTGGAGGCAC GCTTGGCTGC CACTCAAGTG
        670        680        690        700        710        720
AACCACCGTC GCAGCCGACG GCAATGCCCG GCGGTCCGCC CGACGCGCCT CCCCCCGCCA
TTGGTGGCAG CGTCGGCTGC CGTTACGGGC CGCCAGGCGG GCTGCGCGGA GGGGGGCGGT
        730        740        750        760        770        780
TGCCGCAGAT GCCACCCGGC GTGGCCGAGG CGGTACAAGC TGCCGTGCAG GCGGCCGTGG
ACGGCGTCTA CGGTGGGCCG CACCGGCTCC GCCATGTTCG ACGGCACGTC CGCCGGCACC
        790        800        810        820        830        840
CCGCGGCTCT ACAACAACAG CAGCAGCATC AGACCGGAAC GTAACCCGCC CCCGGTGCGA
GGCGCCGAGA TGTTGTTGTC GTCGTCGTAG TCTGGCCTTG CATTGGGCGG GGGCCACGCT
        850        860        870        880        890        900
TAAGGAATTT TCCGACTTGG CGCACATCTC CTTCCTCAAT GTTTGGACAA TAAACACATT
ATTCCTTAAA AGGCTGAACC GCGTGTAGAG GAAGGAGTTA CAAACCTGTT ATTTGTGTAA
        910        920        930        940        950        960
CCTTGCCAAA AAATGACGTT TCCAGAAATC CAAGGCATAA ATGTCCGTAC ACCGGCCCTT
GGAACGGTTT TTTACTGCAA AGGTCTTTAG GTTCCGTATT TACAGGCATG TGGCCGGGAA
        970        980        990       1000       1010       1020
CCCAACACGG AGTTTGAGAT TCCAAGCAGG AGAGAAGATC ATGGTGTGGA TATGGCTCGG
GGGTTGTGCC TCAAACTCTA AGGTTCGTCC TCTCTTCTAG TACCACACCT ATACCGAGCC
```

Fig. 1A (SEQ ID NO: 1)

```
              1030       1040       1050       1060       1070       1080
         CATCGGGCTC CTCGGCGGTA CCGGACTGGC TTCCCTGGTC CTGGCCATTT CCTTATTTAC
         GTAGCCCGAG GAGCCGCCAT GGCCTGACCG AAGGGACCAG GACCGGTAAA GGAATAAATG
              1090       1100       1110       1120       1130       1140
         CCAGCGCCGA GGCCGCAAGC GATCCGACGA GACTTCGTCG CGAGGCCGGC TCCCGGGTGC
         GGTCGCGGCT CCGGCGTTCG CTAGGCTGCT CTGAAGCAGC GCTCCGGCCG AGGGCCCACG
              1150       1160       1170       1180       1190       1200
         TGCTTCTGAT AAGCGTGGTG CCTGCGCGTG CTGCTATCGA AATCCGAAAG AAGACGTCGT
         ACGAAGACTA TTCGCACCAC GGACGCGCAC GACGATAGCT TTAGGCTTTC TTCTGCAGCA
              1210       1220       1230       1240       1250       1260
         CGAGCCGCTG GATCTGGAAC TGGGGCTCAT GCGGGTGGAC ACCCACCCGC CGACGCCGCA
         GCTCGGCGAC CTAGACCTTG ACCCCGAGTA CGCCCACCTG TGGGTGGGCG GCTGCGGCGT
              1270       1280       1290       1300       1310       1320
         GGTGCCGCGG TGTACGTCGC TCTACATAGG AGAGGATGGT CTGCCGATAG ATAAACCCGA
         CCACGGCGCC ACATGCAGCG AGATGTATCC TCTCCTACCA GACGGCTATC TATTTGGGCT
              1330       1340       1350       1360       1370       1380
         GTTTCCTCCG GCGCGGTTCG AGATCCCCGA CGTATCCACG CCGGGAACGC CGACCAGCAT
         CAAAGGAGGC CGCGCCAAGC TCTAGGGGCT GCATAGGTGC GGCCCTTGCG GCTGGTCGTA
              1390       1400       1410       1420       1430       1440
         CGGCCGATCT CCGTCGCATT GCTCCTCGTC GAGCTCTTTG TCGTCCTCGA CCAGCGTCGA
         GCCGGCTAGA GGCAGCGTAA CGAGGAGCAG CTCGAGAAAC AGCAGGAGCT GGTCGCAGCT
              1450       1460       1470       1480       1490       1500
         CACGGTGCTG TATCAGCCGC CGCCATCCTG GAAGCCACCT CCGCCGCCCG GGCGCAAGAA
         GTGCCACGAC ATAGTCGGCG GCGGTAGGAC CTTCGGTGGA GGCGGCGGGC CCGCGTTCTT
              1510       1520       1530       1540       1550       1560
         GCGGCCGCCT ACGCCGCCGG TCCGGGCCCC CACCACGCGG CTGTCGTCGC ACAGACCCCC
         CGCCGGCGGA TGCGGCGGCC AGGCCCGGGG GTGGTGCGCC GACAGCAGCG TGTCTGGGGG
              1570       1580       1590       1600       1610       1620
         GACGCCGATA CCCGCGCCGC GTAAGAACCT GAGCACGCCG CCCACCAAGA AAACGCCGCC
         CTGCGGCTAT GGGCGCGGCG CATTCTTGGA CTCGTGCGGC GGGTGGTTCT TTTGCGGCGG
              1630       1640       1650       1660       1670       1680
         GCCCACGAAA CCCAAGCCGG TCGGCTGGAC ACCGCCGGTG ACACCCAGGC CCTTCCCGAA
         CGGGTGCTTT GGGTTCGGCC AGCCGACCTG TGGCGGCCAC TGTGGGTCCG GGAAGGGCTT
              1690       1700       1710       1720       1730       1740
         AACGCCGACG CCACAAAAGC CGCCGCGGAA TCCAGAGACTA CCGCGCACCG TCGGTCTGGA
         TTGCGGCTGC GGTGTTTTCG GCGGCGCCTT AGGCTCTGAT GGCGCGTGGC AGCCAGACCT
              1750       1760       1770       1780       1790       1800
         GAATCTCTCG AAGGTGGGAC TCTCGTGTCC CTGTCCCCGA CCCCGCACGC CGACGGAGCC
         CTTAGAGAGC TTCCACCCTG AGAGCACAGG GACAGGGGCT GGGGCGTGCG GCTGCCTCGG
              1810       1820       1830       1840       1850       1860
         GACCACGCTG CCTATCGTGT CGGTTTCCGA GCTAGCCCCG CCTCCTCGAT GGTCGGACAT
         CTGGTGCGAC GGATAGCACA GCCAAAGGCT CGATCGGGGC GGAGGAGCTA CCAGCCTGTA
              1870       1880       1890       1900       1910       1920
         CGAGGAACTC TTGGAACAGG CGGTGCAGAG CGTCATGAAG GACGCCGAGT CGATGCAGAT
         GCTCCTTGAG AACCTTGTCC GCCACGTCTC GCAGTACTTC CTGCGGCTCA GCTACGTCTA
              1930       1940       1950       1960       1970       1980
         GACCTGAGAC CGAAAGAGCG AGCGCGTCCG TTGTACAGTT GTATAGCAGC ACACGCCTTC
         CTGGACTCTG GCTTTCTCGC TCGCGCAGGC AACATGTCAA CATATCGTCG TGTGCGGAAG
              1990       2000       2010       2020       2030       2040
         CCTCTTTTTC ACCGCAGCTA AGAGAGAGAA AGAGAGTATG TCAGTCAAGG GCGTGGAGAT
         GGAGAAAAAG TGGCGTCGAT TCTCTCTCTT TCTCTCATAC AGTCAGTTCC CGCACCTCTA
```

Fig. 1B (SEQ ID NO: 1)

```
       2050       2060       2070       2080       2090       2100
GCCAGAAATG ACGTGGGACT TGGACGTTAG AAATAAATGG CGGCGTCGAA AGGCCCTGAG
CGGTCTTTAC TGCACCCTGA ACCTGCAATC TTTATTTACC GCCGCAGCTT TCCGGGACTC
       2110       2120       2130       2140       2150       2160
TCGCATTCAC CGGTTCTGGG AATGTCGGCT ACGGGTGTGG TGGCTGAGTG ACGCCGGCGT
AGCGTAAGTG GCCAAGACCC TTACAGCCGA TGCCCACACC ACCGACTCAC TGCGGCCGCA
       2170       2180       2190       2200       2210       2220
AAGAGAAACC GACCCACCGC GTCCCCGACG CCGCCCGACT TGGATGACCG CGGTGTTTCA
TTCTCTTTGG CTGGGTGGCG CAGGGGCTGC GGCGGGCTGA ACCTACTGGC GCCACAAAGT
       2230       2240       2250       2260       2270       2280
CGTTATCTGT GCCGTTTTGC TTACGCTTAT GATTATGGCC ATCGGCGCGC TCATCGCGTA
GCAATAGACA CGGCAAAACG AATGCGAATA CTAATACCGG TAGCCGCGCG AGTAGCGCAT
       2290       2300       2310       2320       2330       2340
CTTAAGATAT TACCACCAGG ACAGTTGGCG AGACATGCTC CACGATCTAT TTTGCGGCTG
GAATTCTATA ATGGTGGTCC TGTCAACCGC TCTGTACGAG GTGCTAGATA AAACGCCGAC
       2350       2360       2370       2380       2390       2400
TCATTATCCC GAGAAGTGCC GTCGGCACCA CGAGCGGCAG AGAAGGAGAC GGCAAGCCAT
AGTAATAGGG CTCTTCACGG CAGCCGTGGT GCTCGCCGTC TCTTCCTCTG CCGTTCGGTA
       2410       2420       2430       2440       2450       2460
GGATGTGCCC GACCCGGAAC TCGGCGACCC GGCCCGCCGG CCGTTGAACG GAGCTATGTA
CCTACACGGG CTGGGCCTTG AGCCGCTGGG CCGGGCGGCC GGCAACTTGC CTCGATACAT
       2470       2480       2490       2500       2510       2520
CTACGGCAGC GGCTGTCGCT TCGACACGGT GGAAATGGTG GACGAGACGA GACCCGCGCC
GATGCCGTCG CCGACAGCGA AGCTGTGCCA CCTTTACCAC CTGCTCTGCT CTGGGCGCGG
       2530       2540       2550       2560       2570       2580
GCCGGCGCTG TCATCGCCCG AAACCGGCGA CGATAGCAAC GACGACGCGG TTGCCGGCGG
CGGCCGCGAC AGTAGCGGGC TTTGGCCGCT GCTATCGTTG CTGCTGCGCC AACGGCCGCC
       2590       2600       2610       2620       2630       2640
AGGTGCTGGC GGGGTAACAT CACCCGCGAC TCGTACGACG TCGCCGAACG CACTGCTGCC
TCCACGACCG CCCCATTGTA GTGGGCGCTG AGCATGCTGC AGCGGCTTGC GTGACGACGG
       2650       2660       2670       2680       2690       2700
AGAATGGATG GATGCGGTGC ATGTGGCGGT CCAAGCCGCC GTTCAAGCGA CCGTGCAAGT
TCTTACCTAC CTACGCCACG TACACCGCCA GGTTCGGCGG CAAGTTCGCT GGCACGTTCA
       2710       2720       2730       2740       2750       2760
AAGTGGCCCG CGGGAGAACG CCGTATCTCC CGCTACGTAA GAGGGTTGAG GGGGCCGTTC
TTCACCGGGC GCCCTCTTGC GGCATAGAGG GCGATGCATT CTCCCAACTC CCCCGGCAAG
       2770       2780       2790       2800       2810       2820
CCGCGCGAGT GCTGTACAAA AGAGAGAGAC TGGGACGTAG ATCCGGACAG AGGACGGTCA
GGCGCGCTCA CGACATGTTT TCTCTCTCTG ACCCTGCATC TAGGCCTGTC TCCTGCCAGT
       2830       2840       2850       2860       2870       2880
CCATGGACGA TCTGCCGCTG AATGTCGGGT TACCCATCAT CGGCGTGATG CTCGTGCTGA
GGTACCTGCT AGACGGCGAC TTACAGCCCA ATGGGTAGTA GCCGCACTAC GAGCACGACT
       2890       2900       2910       2920       2930       2940
TCGTGGCCAT CCTCTGCTAT CTGGCTTACC ACTGGCACGA CACCTTCAAA CTGGTGCGCA
AGCACCGGTA GGAGACGATA GACCGAATGG TGACCGTGCT GTGGAAGTTT GACCACGCGT
       2950       2960       2970       2980       2990       3000
TGTTTCTGAG CTACCGCTGG CTGATCCGCT GTTGCGAGCT GTACGGGGAG TACGAGCGCC
ACAAAGACTC GATGGCGACC GACTAGGCGA CAACGCTCGA CATGCCCCTC ATGCTCGCGG
       3010       3020       3030       3040       3050       3060
GGTTCGCGGA CCTGTCGTCT CTGGGCCTCG GCGCCGTACG GCGGGAGTCG ACAGACGAT
CCAAGCGCCT GGACAGCAGA GACCCGGAGC CGCGGCATGC CGCCCTCAGC CTGTCTGCTA
```

Fig. 1C (SEQ ID NO: 1)

```
       3070       3080       3090       3100       3110       3120
ACCGTTTCTC CGAACGGCCC GACGAGATCT TGGTCCGTTG GGAGGAAGTG TCTTCCCAGT
TGGCAAAGAG GCTTGCCGGG CTGCTCTAGA ACCAGGCAAC CCTCCTTCAC AGAAGGGTCA
       3130       3140       3150       3160       3170       3180
GCAGCTACGC GTCGTCGCGG ATAACAGACC GCCGTGTGGG TTCATCGTCT TCGTCGTCGG
CGTCGATGCG CAGCAGCGCC TATTGTCTGG CGGCACACCC AAGTAGCAGA AGCAGCAGCC
       3190       3200       3210       3220       3230       3240
TCCACGTCGC TAGCCAGAGA AACAGCGTGC CTCCGCCGGA CATGGCGGTG ACGGCGCCGC
AGGTGCAGCG ATCGGTCTCT TTGTCGCACG GAGGCGGCCT GTACCGCCAC TGCCGCGGCG
       3250       3260       3270       3280       3290       3300
TGACCGACGT CGATCTGTTG AAACCCGTGA CGGGATCCGC GACGCAGTTC ACCACCGTAG
ACTGGCTGCA GCTAGACAAC TTTGGGCACT GCCCTAGGCG CTGCGTCAAG TGGTGGCATC
       3310       3320       3330       3340       3350       3360
CCATGGTACA TTATCATCAA GAGTACACGT GAATGAGAAA AAGAAAAAAG AGGGGAGCGG
GGTACCATGT AATAGTAGTT CTCATGTGCA CTTACTCTTT TTCTTTTTTC TCCCCTCGCC
       3370       3380       3390       3400       3410       3420
ATCGCGATAA TGTCGCTTTG ACATTCTCTG CTCGATCTAC TCAGCGTCTG CACGAAACGG
TAGCGCTATT ACAGCGAAAC TGTAAGAGAC GAGCTAGATG AGTCGCAGAC GTGCTTTGCC
       3430       3440       3450       3460       3470       3480
CATCCGCACG GAGGCGAGCC CAAGCGTATC TGCAGCAAGC GGTTCTTTCC CTCGGTGATG
GTAGGCGTGC CTCCGCTCGG GTTCGCATAG ACGTCGTTCG CCAAGAAAGG GAGCCACTAC
       3490       3500       3510       3520       3530       3540
GTGGCAGCAT CGGTGGCGGG AGCTTGTTCG GACGATGGAC GGTGAGGAGT CCCTGGCGAT
CACCGTCGTA GCCACCGCCC TCGAACAAGC CTGCTACCTG CCACTCCTCA GGGACCGCTA
       3550       3560       3570       3580       3590       3600
CAGGCGGCTC CCGGGTGTGG AGTTCAACGG GTGGTAATGG TGGCGGTGAT CGGTGTTAGA
GTCCGCCGAG GGCCCACACC TCAAGTTGCC CACCATTACC ACCGCCACTA GCCACAATCT
       3610       3620       3630       3640       3650       3660
AAACGGTGGC CCTGGCAAAC ATATATCTAC TGTAAACCCT CTGCTCTGTT AATAAAAAGC
TTTGCCACCG GGACCGTTTG TATATAGATG ACATTTGGGA GACGAGACAA TTATTTTTCG
       3670       3680       3690       3700       3710       3720
ACACTTTTCA CATGAGTTCG TAATTTTATT GTGTAGTGGA AATTTTTACG TCATTGGGAA
TGTGAAAAGT GTACTCAAGC ATTAAAATAA CACATCACCT TTAAAAATGC AGTAACCCTT
       3730       3740       3750       3760       3770       3780
ACCCCAGAAT GAAAGAGTAT AATGTGCATA TCACCGGGGG TTCCCTGTCA GTACGAATGT
TGGGGTCTTA CTTTCTCATA TTACACGTAT AGTGGCCCCC AAGGGACAGT CATGCTTACA
       3790       3800       3810       3820       3830       3840
ACACAACGCG GGTTACATTA CGATAAACTT TCCGGTAAAA CGATGCCGAT ACAGCGTGTA
TGTGTTGCGC CCAATGTAAT GCTATTTGAA AGGCCATTTT GCTACGGCTA TGTCGCACAT
       3850       3860       3870       3880       3890       3900
TAACGCTGAT TGTTACGACA AACGAGTTGG TATATCCATT ATATAGTAAC GAACATGCTG
ATTGCGACTA ACAATGCTGT TTGCTCAACC ATATAGGTAA TATATCATTG CTTGTACGAC
       3910       3920       3930       3940       3950       3960
TGGATATTAG TTTTATTTGC ACTCGCCGCA TCGGCGAGTG AAACCACTAC AGGTACCAGC
ACCTATAATC AAAATAAACG TGAGCGGCGT AGCCGCTCAC TTTGGTGATG TCCATGGTCG
       3970       3980       3990       4000       4010       4020
TCTAATTCCA GTCAATCTAC TAGTGCTACC GCCAACACGA CCGTATCGAC ATGTATTAAT
AGATTAAGGT CAGTTAGATG ATCACGATGG CGGTTGTGCT GGCATAGCTG TACATAATTA
       4030       4040       4050       4060       4070       4080
GCCTCTAACG GCAGTAGCTG GACAGTACCA CAGCTCGCGC TGCTTGCCGC TAGCGGCTGG
CGGAGATTGC CGTCATCGAC CTGTCATGGT GTCGAGCGCG ACGAACGGCG ATCGCCGACC
```

Fig. 1D (SEQ ID NO: 1)

```
      4090       4100       4110       4120       4130       4140
ACATTATCTG GACTCCTTCT CTTATTTACC TGCTGCTTTT GCTGCTTTTG GCTAGTACGT
TGTAATAGAC CTGAGGAAGA GAATAAATGG ACGACGAAAA CGACGAAAAC CGATCATGCA
      4150       4160       4170       4180       4190       4200
AAAATCTGCA GCTGCTGCGG CAACTCCTCC GAGTCAGAGA GCAAAACAAC CCACGCGTAC
TTTTAGACGT CGACGACGCC GTTGAGGAGG CTCAGTCTCT CGTTTTGTTG GGTGCGCATG
      4210       4220       4230       4240       4250       4260
ACCAATGCCG CATTCACTTC TTCCGACGCA ACGTTACCCA TGGGCACTAC AGGGTCGTAC
TGGTTACGGC GTAAGTGAAG AAGGCTGCGT TGCAATGGGT ACCCGTGATG TCCCAGCATG
      4270       4280       4290       4300       4310       4320
ACTCCCCCAC AGGACGGCTC ATTTCCACCT CCGCCTCGGT GACGTAGGCT AAACCGAAAC
TGAGGGGGTG TCCTGCCGAG TAAAGGTGGA GGCGGAGCCA CTGCATCCGA TTTGGCTTTG
      4330       4340       4350       4360       4370       4380
CCACGTTGAA CCTAACGCGG TTTCGGAAGG CCTGAGACGT CACTTTCACA ATGACGTCCG
GGTGCAACTT GGATTGCGCC AAAGCCTTCC GGACTCTGCA GTGAAAGTGT TACTGCAGGC
      4390       4400       4410       4420       4430       4440
TATACACGTT CATCATAAAA CACCGTAGAG GCTAAGGCTT CGGTAGGGAG AGACCTCAAC
ATATGTGCAA GTAGTATTTT GTGGCATCTC CGATTCCGAA GCCATCCCTC TCTGGAGTTG
      4450       4460       4470       4480       4490       4500
TGTTCCTGAT GAGCACCCGT GCTCTCATCT CTTCAGACTT GTCATGACCC CCGCTCAGAC
ACAAGGACTA CTCGTGGGCA CGAGAGTAGA GAAGTCTGAA CAGTACTGGG GGCGAGTCTG
      4510       4520       4530       4540       4550       4560
TAACGCGACT ACCACCGTGC ACCCGCACGA CGCAAAAAAC GGCAGCGGCG GTAGTGCCCT
ATTGCGCTGA TGGTGGCACG TGGGCGTGCT GCGTTTTTTG CCGTCGCCGC CATCACGGGA
      4570       4580       4590       4600       4610       4620
GCCGACCCTC GTCGTTTTCG GCTTTATCGT TACGCTACTT TTCTTTCTCT TTATGCTCTA
CGGCTGGGAG CAGCAAAAGC CGAAATAGCA ATGCGATGAA AAGAAAGAGA AATACGAGAT
      4630       4640       4650       4660       4670       4680
CTTTTGGAAC AACGACGTGT TCCGTAAGCT GCTCCGTGCG CTTGGATCCA GCGCTGTTGC
GAAAACCTTG TTGCTGCACA AGGCATTCGA CGAGGCACGC GAACCTAGGT CGCGACAACG
      4690       4700       4710       4720       4730       4740
GACCGCTTCG ACGCGTGGCA AGACGAGGTC ATCTACCGTC GTCCATCACG TCGTTCCCAG
CTGGCGAAGC TGCGCACCGT TCTGCTCCAG TAGATGGCAG CAGGTAGTGC AGCAAGGGTC
      4750       4760       4770       4780       4790       4800
AGCGACGACG AGAGTCGTAC TAACAGCGTG TCATCGTACG TTCTTTTATC ACCCGCGTCC
TCGCTGCTGC TCTCAGCATG ATTGTCGCAC AGTAGCATGC AAGAAAATAG TGGGCGCAGG
      4810       4820       4830       4840       4850       4860
GATGGCGGTT TTGACAACCC GGCACTGACA GAGGCCGTCG ACAGCGTGGA CGACTGGGCG
CTACCGCCAA AACTGTTGGG CCGTGACTGT CTCCGGCAGC TGTCGCACCT GCTGACCCGC
      4870       4880       4890       4900       4910       4920
ACCACCTCGG TTTTCTACGC CACGTCCGAC GAAACGGCGG ACGCCGAGCG CCGAGACTCG
TGGTGGAGCC AAAAGATGCG GTGCAGGCTG CTTTGCCGCC TGCGGCTCGC GGCTCTGAGC
      4930       4940       4950       4960       4970       4980
CAGCAACTGC TCATCGAGCT TCCGCCGGAG CCGCTCCCGC CCGACGTGGT GGCGGCCATG
GTCGTTGACG AGTAGCTCGA AGGCGGCCTC GGCGAGGGCG GGCTGCACCA CCGCCGGTAC
      4990       5000       5010       5020       5030       5040
CAGAAAGCAG TGAAACGCGC TGTACAGAAC GCACTACGAC ACAGCCACGA CTCTTGGCAG
GTCTTTCGTC ACTTTGCGCG ACATGTCTTG CGTGATGCTG TGTCGGTGCT GAGAACCGTC
      5050       5060       5070       5080       5090       5100
CTTCATCAGA CCCTGTGACG CCAGATGAAC GTTCCTTCTT AAACATCCGA GGTAGCAATG
GAAGTAGTCT GGGACACTGC GGTCTACTTG CAAGGAAGAA TTTGTAGGCT CCATCGTTAC
```

Fig. 1E (SEQ ID NO: 1)

```
       5110        5120       5130       5140       5150       5160
AGACAGGTCG  CGTACCGCCG GCGACGGCGAG AGTTCCTGCG CGGTGCTGGT CCACCACGTC
TCTGTCCAGC  GCATGGCGGC CGCTGCGCTC TCAAGGACGC GCCACGACCA GGTGGTGCAG 5170        5180       5190       5200       5210       5220
GGCCGCGACG  GCGACGGCGA GGGGGAGGCA GCAAAAAAGA CCTGCAAAAA AACCGGACGC
CCGGCGCTGC  CGCTGCCGCT CCCCCTCCGT CGTTTTTTCT GGACGTTTTT TTGGCCTGCG 5230        5240       5250       5260       5270       5280
TCAGTTGCGG  GCATCCCGGG CGAGAAGCTG CGTCGCACGG TGGTCACCAC CACGCCGGCC
AGTCAACGCC  CGTAGGGCCC GCTCTTCGAC GCAGCGTGCC ACCAGTGGTG GTGCGGCCGG 5290        5300       5310       5320       5330       5340
CGACGTTTGA  GCGGCCGACA CACGGAGCAG GAGCAGGCGG GCATGCGTCT CTGTGAAAAA
GCTGCAAACT  CGCCGGCTGT GTGCCTCGTC CTCGTCCGCC CGTACGCAGA GACACTTTTT 5350        5360       5370       5380       5390       5400
GGGAAGAAAA  GAATCATCAT GTGCCGCCGG GAGTCGCTCC GAACTCTGCC GTGGCTGTTC
CCCTTCTTTT  CTTAGTAGTA CACGGCGGCC CTCAGCGAGG CTTGAGACGG CACCGACAAG 5410        5420       5430       5440       5450       5460
TGGGTGCTGT  TGAGCTGCCC GCGACTCCTC GAATATTCTT CCTCTTCGTT CCCCTTCGCC
ACCCACGACA  ACTCGACGGG CGCTGAGGAG CTTATAAGAA GGAGAAGCAA GGGGAAGCGG 5470        5480       5490       5500       5510       5520
ACCGCTGACA  TTGCCGAAAA GATGTGGGCC GAGAATTATG AGACCACGTC GCCGGCGCCG
TGGCGACTGT  AACGGCTTTT CTACACCCGG CTCTTAATAC TCTGGTGCAG CGGCCGCGGC 5530        5540       5550       5560       5570       5580
GTGTTGGTCG  CCGAGGGAGA GCAAGTTACC ATCCCCTGCA CGGTCATGAC ACACTCCTGG
CACAACCAGC  GGCTCCCTCT CGTTCAATGG TAGGGGACGT GCCAGTACTG TGTGAGGACC 5590        5600       5610       5620       5630       5640
CCCATGGTCT  CCATTCGCGC ACGTTTCTGT CGTTCCCACG ACGGCAGCGA CGAGCTCATC
GGGTACCAGA  GGTAAGCGCG TGCAAAGACA GCAAGGGTGC TGCCGTCGCT GCTCGAGTAG 5650        5660       5670       5680       5690       5700
CTGGACGCCG  TCAAAGGCCA TCGGCTGATG AACGGACTCC AGTACCGCCT GCCGTACGCC
GACCTGCGGC  AGTTTCCGGT AGCCGACTAC TTGCCTGAGG TCATGGCGGA CGGCATGCGG 5710        5720       5730       5740       5750       5760
ACTTGGAATT  TCTCGCAATT GCATCTCGGC CAAATATTCT CGCTTACTTT TAACGTATCG
TGAACCTTAA  AGAGCGTTAA CGTAGAGCCG GTTTATAAGA GCGAATGAAA ATTGCATAGC 5770        5780       5790       5800       5810       5820
ATGGACACAG  CCGGCATGTA CGAATGCGTG CTACGCAACT ACAGCCACGG CCTCATCATG
TACCTGTGTC  GGCCGTACAT GCTTACGCAC GATGCGTTGA TGTCGGTGCC GGAGTAGTAC 5830        5840       5850       5860       5870       5880
CAACGCTTCG  TAATTCTCAC GCAGCTGGAG ACGCTCAGCC GGCCCGACGA ACCTTGCTGC
GTTGCGAAGC  ATTAAGAGTG CGTCGACCTC TGCGAGTCGG CCGGGCTGCT TGGAACGACG 5890        5900       5910       5920       5930       5940
ACACCGGCGT  TAGGTCGCTA CTCGCTGGGA GACCAGATCT GGTCGCCGAC GCCCTGGCGT
TGTGGCCGCA  ATCCAGCGAT GAGCGACCCT CTGGTCTAGA CCAGCGGCTG CGGGACCGCA 5950        5960       5970       5980       5990       6000
CTACGGAATC  ACGACTGCGA AACGTACCGC GGCTTTCAAC GCAACTACTT CTATATCGGC
GATGCCTTAG  TGCTGACGCC TTGCATGGCG CCGAAAGTTG CGTTGATGAA GATATAGCCG 6010        6020       6030       6040       6050       6060
CCCGCCGACG  CCGAGGATTG CTGGAAACCC GCATGTCCGG ACGAGGAACC CGACCGCTGT
GCGCGGCTGC  GGCTCCTAAC GACCTTTGGG CGTACAGGCC TGCTCCTTGG GCTGGCGACA 6070        6080       6090       6100       6110       6120
TGGACAGTGA  TACAGCGTTA CCGGCTCCCC GGCGACTGCT ACCGTTCGCA GCCACACCCG
ACCTGTCACT  ATGTCGCAAT GGCCGAGGGG CCGCTGACGA TGGCAAGCGT CGGTGTGGGC
```

Fig. 1F (SEQ ID NO: 1)

```
              6130       6140       6150       6160       6170       6180
         CCGAAATTTT TACCGGTGAC GCCAGCACCG CCGGCCGACA TAGACACCGG GATGTCTCCC
         GGCTTTAAAA ATGGCCACTG CGGTCGTGGC GGCCGGCTGT ATCTGTGGCC CTACAGAGGG
              6190       6200       6210       6220       6230       6240
         TGGGCCACTC GGGGAATCGC GGCGTTTTTG GGGTTTTGGA GTATTTTTAC CGTATGTTTC
         ACCCGGTGAG CCCCTTAGCG CCGCAAAAAC CCCAAAACCT CATAAAAATG GCATACAAAG
              6250       6260       6270       6280       6290       6300
         CTATGCTACC TGTGTTATCT GCAGTGTTGT GGACGCTGGT GTCCCACGCC GGGAAGGGGA
         GATACGATGG ACACAATAGA CGTCACAACA CCTGCGACCA CAGGGTGCGG CCCTTCCCCT
              6310       6320       6330       6340       6350       6360
         CGACGAGGCG GTGAGGGCTA TCGACGCCTA CCGACTTACG ATAGTTACCC CGGTGTTAGA
         GCTGCTCCGC CACTCCCGAT AGCTGCGGAT GGCTGAATGC TATCAATGGG GCCACAATCT
              6370       6380       6390       6400       6410       6420
         AAGATGAAGA GGTGAGAACA CGTATAAAAT AAAAAAATAA TATGTTAAAA AATGCAGTGT
         TTCTACTTCT CCACTCTTGT GCATATTTTA TTTTTTTATT ATACAATTTT TTACGTCACA
              6430       6440       6450       6460       6470       6480
         GTGAAGTGTG AATAGTGTGA TTAAAATATG CGGATTGAAT GGGTGTGGTG GTTATTCGGA
         CACTTCACAC TTATCACACT AATTTTATAC GCCTAACTTA CCCACACCAC CAATAAGCCT
              6490       6500       6510       6520       6530       6540
         TACTTTGTGT CATCCGTTGG GAGCGAACGG TCATTATCCT ATCGTTACCA CTTGGAATCT
         ATGAAACACA GTAGGCAACC CTCGCTTGCC AGTAATAGGA TAGCAATGGT GAACCTTAGA
              6550       6560       6570       6580       6590       6600
         AATTCATCTA CCAACGTGGT TTGCAACGGA AACATTTCCG TGTTTGTAAA CGGCACCCTA
         TTAAGTAGAT GGTTGCACCA AACGTTGCCT TTGTAAAGGC ACAAACATTT GCCGTGGGAT
              6610       6620       6630       6640       6650       6660
         GGTGTGCGGT ATAACATTAC GGTAGGAATC AGTTCGTCTT TATTAATAGG ACACCTTACT
         CCACACGCCA TATTGTAATG CCATCCTTAG TCAAGCAGAA ATAATTATCC TGTGGAATGA
              6670       6680       6690       6700       6710       6720
         ATACAAGTAT TGGAATCATG GTTCACACCC TGGGTCCAAA ATAAAAGTTA CAACAAACAA
         TATGTTCATA ACCTTAGTAC CAAGTGTGGG ACCCAGGTTT TATTTTCAAT GTTGTTTGTT
              6730       6740       6750       6760       6770       6780
         CCCCTAGGTG ACACTGAAAC GCTTTATAAT ATAGATAGCG AAAACATTCA TCGCGTATCT
         GGGGATCCAC TGTGACTTTG CGAAATATTA TATCTATCGC TTTTGTAAGT AGCGCATAGA
              6790       6800       6810       6820       6830       6840
         CAATATTTTC ACACAAGATG GATAAAATCT CTGCAAGAGA ATCACACTTG CGACCTCACA
         GTTATAAAAG TGTGTTCTAC CTATTTTAGA GACGTTCTCT TAGTGTGAAC GCTGGAGTGT
              6850       6860       6870       6880       6890       6900
         AACAGTACAC CTACCTATAC ATATCAAGTA AACGTGAACA ACACGAATTA CCTAACACTA
         TTGTCATGTG GATGGATATG TATAGTTCAT TTGCACTTGT TGTGCTTAAT GGATTGTGAT
              6910       6920       6930       6940       6950       6960
         ACATCCTCGG GATGGCAAGA CCGTCTAAAT TACACCGTCA TAAATAGTAC ACACTTTAAC
         TGTAGGAGCC CTACCGTTCT GGCAGATTTA ATGTGGCAGT ATTTATCATG TGTGAAATTG
              6970       6980       6990       7000       7010       7020
         CTCACAGAAT CGAACATAAC CAGCATTCAA AAATATCTCA ACACTACCTG CATAGAAAGA
         GAGTGTCTTA GCTTGTATTG GTCGTAAGTT TTTATAGAGT TGTGATGGAC GTATCTTTCT
              7030       7040       7050       7060       7070       7080
         CTCCGTAACT ACACCTTGGA GTCCGTATAC ACCACAACTG TGCCTCAAAA CATAACAACA
         GAGGCATTGA TGTGGAACCT CAGGCATATG TGGTGTTGAC ACGGAGTTTT GTATTGTTGT
              7090       7100       7110       7120       7130       7140
         TCTCAACACG CAACAACCAC TATGCACACA ATACCTCCAA ATACAATAAC AATTCAAAAT
         AGAGTTGTGC GTTGTTGGTG ATACGTGTGT TATGGAGGTT TATGTTATTG TTAAGTTTTA
```

Fig. 1G (SEQ ID NO: 1)

```
          7150       7160       7170       7180       7190       7200
     ACAACTCAAA GCCATACTGT ACAGACGCCG TCTTTTAACG ACACACATAA CGTGACGAAA
     TGTTGAGTTT CGGTATGACA TGTCTGCGGC AGAAAATTGC TGTGTGTATT GCACTGCTTT
          7210       7220       7230       7240       7250       7260
     CACACGTTAA ACATAAGCTA CGTTTTATCA CAAAAAACGA ATAACACAAC ATCACCGTGG
     GTGTGCAATT TGTATTCGAT GCAAAATAGT GTTTTTTGCT TATTGTGTTG TAGTGGCACC
          7270       7280       7290       7300       7310       7320
     ATATATGCCA TACCTATGGG CGCTACAGCC ACAATAGGCG CCGGTTTATA TATCGGGAAA
     TATATACGGT ATGGATACCC GCGATGTCGG TGTTATCCGC GGCCAAATAT ATAGCCCTTT
          7330       7340       7350       7360       7370       7380
     CACTTTACGC CGGTTAAGTT CGTATACGAG GTATGGCGCG GTCAGTAAAG ACGATTCGGA
     GTGAAATGCG GCCAATTCAA GCATATGCTC CATACCGCGC CAGTCATTTC TGCTAAGCCT
          7390       7400       7410       7420       7430       7440
     TTCAACACAT ATACTCCCCA CGATCCTCGA ACACCTTACA GCATATGAGC AAAAAACAAG
     AAGTTGTGTA TATGAGGGGT GCTAGGAGCT TGTGGAATGT CGTATACTCG TTTTTTGTTC
          7450       7460       7470       7480       7490       7500
     AAAGTATAGC CACAATCACA TTTGGGCGAA TAACATGCTG TCATCCACTA GCGTCTATTA
     TTTCATATCG GTGTTAGTGT AAACCCGCTT ATTGTACGAC AGTAGGTGAT CGCAGATAAT
          7510       7520       7530       7540       7550       7560
     ATCTAATGTT TAACGGGAGC TGTACTGTCA CCGTTAAAAT ATCCATGGGA ATCAACGGGT
     TAGATTACAA ATTGCCCTCG ACATGACAGT GGCAATTTTA TAGGTACCCT TAGTTGCCCA
          7570       7580       7590       7600       7610       7620
     CAACCAACGT CCATCAGCTT GTGATTGTGC TCCATCTGGG TAACCGCTGT CAGCCTTGGC
     GTTGGTTGCA GGTAGTCGAA CACTAACACG AGGTAGACCC ATTGGCGACA GTCGGAACCG
          7630       7640       7650       7660       7670       7680
     GACAGGTGTA ATCACAGCTG TCACATAACT CACGAAGCCT CCAATCACAG CAGCACACAT
     CTGTCCACAT TAGTGTCGAC AGTGTATTGA GTGCTTCGGA GGTTAGTGTC GTCGTGTGTA
          7690       7700       7710       7720       7730       7740
     AGTCCTAACG CCATTGGCGT GTATAAAAGT TCGGAAAACT TGACGGTTGT ACGGCACGAC
     TCAGGATTGC GGTAACCGCA CATATTTTCA AGCCTTTTGA ACTGCCAACA TGCCGTGCTG
          7750       7760       7770       7780       7790       7800
     AAATCGATGT AGTGGTATGT TTTTCCAGCA GAGACCGTGT GCGGTCTCTT AGGTTCGCTA
     TTTAGCTACA TCACCATACA AAAAGGTCGT CTCTGGCACA CGCCAGAGAA TCCAAGCGAT
          7810       7820       7830       7840       7850       7860
     TACTGTGGCT GGAAACTGGT TACCTGTGAA GATGGCTAAC TATCCTGTTC TGTCCTGGAA
     ATGACACCGA CCTTTGACCA ATGGACACTT CTACCGATTG ATAGGACAAG ACAGGACCTT
          7870       7880       7890       7900       7910       7920
     AAACTTTTGG CGTCGTAGGT GGACTTTGCA GTATGCGGGT TAGTGAAGTT ATGTCATTTA
     TTTGAAAACC GCAGCATCCA CCTGAAACGT CATACGCCCA ATCACTTCAA TACAGTAAAT
          7930       7940       7950       7960       7970       7980
     TTTACGTTTA CGATCTCGTA TTACAAACCG CGGAGAGGAT GATACCGTTC GGCCCCATGA
     AAATGCAAAT GCTAGAGCAT AATGTTTGGC GCCTCTCCTA CTATGGCAAG CCGGGGTACT
          7990       8000       8010       8020       8030       8040
     GTTATTTTA TTCTTCCGGT AGGAGGCATG AAGCCTCTGA TAATGCTCAT CTGCTTTGCT
     CAATAAAAAT AAGAAGGCCA TCCTCCGTAC TTCGGAGACT ATTACGAGTA GACGAAACGA
          8050       8060       8070       8080       8090       8100
     GTGATATTAT TGCAGCTTGG AGTGACTAAA GTGTGTCAGC ATAATGAAGT GCAACTGGGC
     CACTATAATA ACGTCGAACC TCACTGATTT CACACAGTCG TATTACTTCA CGTTGACCCG
          8110       8120       8130       8140       8150       8160
     AATGAGTGCT GCCCTCCGTG TGGTTCGGGA CAAAGAGTTA CTAAAGTATG CACGGATTAT
     TTACTCACGA CGGGAGGCAC ACCAAGCCCT GTTTCTCAAT GATTTCATAC GTGCCTAATA
```

Fig. 1H (SEQ ID NO: 1)

```
         8170       8180       8190       8200       8210       8220
    ACCAGTGTAA CGTGTACCCC TTGCCCCAAC GGCACGTATG TATCGGGACT TTACAACTGT
    TGGTCACATT GCACATGGGG AACGGGGTTG CCGTGCATAC ATAGCCCTGA AATGTTGACA
         8230       8240       8250       8260       8270       8280
    ACCGATTGCA CTCAATGTAA CGTCACTCAG GTCATGATTC GTAACTGCAC TTCCACCAAT
    TGGCTAACGT GAGTTACATT GCAGTGAGTC CAGTACTAAG CATTGACGTG AAGGTGGTTA
         8290       8300       8310       8320       8330       8340
    AATACCGTAT GCGCACCTAA GAACCATACG TACTTTTCCA CTCCAGGCGT CCAACATCAC
    TTATGGCATA CGCGTGGATT CTTGGTATGC ATGAAAAGGT GAGGTCCGCA GGTTGTAGTG
         8350       8360       8370       8380       8390       8400
    AAACAACGAC AGCAAAATCA TACCGCACAT ATAACCGTCA AACAAGGAAA AAGCGGTCGT
    TTTGTTGCTG TCGTTTTAGT ATGGCGTGTA TATTGGCAGT TTGTTCCTTT TTCGCCAGCA
         8410       8420       8430       8440       8450       8460
    CATACTCTAG CCTGGTTGTC TCTCTTTATC TTTCTTGTGG GTATCATACT TTTAATTCTC
    GTATGAGATC GGACCAACAG AGAGAAATAG AAAGAACACC CATAGTATGA AAATTAAGAG
         8470       8480       8490       8500       8510       8520
    TATCTTATAG CCGCCTATCG GAGTGAGAGA TGCCAACAGT GTTGCTCAAT CGGCAAAATT
    ATAGAATATC GGCGGATAGC CTCACTCTCT ACGGTTGTCA CAACGAGTTA GCCGTTTTAA
         8530       8540       8550       8560       8570       8580
    TTCTACCGCA CCCTGTAAGC TTCCTGTTGT TGTTTTTACA TCACGGTACG ATGAAGTCAC
    AAGATGGCGT GGGACATTCG AAGGACAACA ACAAAAATGT AGTGCCATGC TACTTCAGTG
         8590       8600       8610       8620       8630       8640
    ACAGATAATT ACAGATGAGC TGTTCATATT TTTTATTATT TTTTCCAATT CCTGCACTAA
    TGTCTATTAA TGTCTACTCG ACAAGTATAA AAAATAATAA AAAAGGTTAA GGACGTGATT
         8650       8660       8670       8680       8690       8700
    AAAAAGAAGC ACTTTACGGA ACCGTGTCTG AGTATCTGTG GGGAATTTAG GTACTTTTTG
    TTTTTCTTCG TGAAATGCCT TGGCACAGAC TCATAGACAC CCCTTAAATC CATGAAAAAC
         8710       8720       8730       8740       8750       8760
    CCGACGTCAG GAAAAATAAG TGTCGCCTAC ATAAGAGCCC GGTGCTATCG TGCTGTCACT
    GGCTGCAGTC CTTTTTATTC ACAGCGGATG TATTCTCGGG CCACGATAGC ACGACAGTGA
         8770       8780       8790       8800       8810       8820
    CTTTCTTGTT GCCTTCGATG TACGGCGTCC TGGCTCATTA CTACTCCTTC ATCAGTAGCC
    GAAAGAACAA CGGAAGCTAC ATGCCGCAGG ACCGAGTAAT GATGAGGAAG TAGTCATCGG
         8830       8840       8850       8860       8870       8880
    CCAGCGTTAT GGTTAATTTT AAGCATCATA ACGCCGTGCA GCTGTTATGT GCACGGACCC
    GGTCGCAATA CCAATTAAAA TTCGTAGTAT TGCGGCACGT CGACAATACA CGTGCCTGGG
         8890       8900       8910       8920       8930       8940
    GAGACGCACT GCCGGATGGG AACGTTTAAC CCATCATGCG TCGTATCACG CGAACTACGG
    CTCTGCGTGA CGGCCTACCC TTGCAAATTG GGTAGTACGC AGCATAGTGC GCTTGATGCC
         8950       8960       8970       8980       8990       9000
    GGCATACGCC GTGTTGATGG CTACATCGCA AAGAAAGTCC CTAGTGTTAC ATCGATACAG
    CCGTATGCGG CACAACTACC GATGTAGCGT TTCTTTCAGG GATCACAATG TAGCTATGTC
         9010       9020       9030       9040       9050       9060
    TGCCGTGACA GCCGTGGCCC TGCAGCTCAT GCCTGTTGAG ATCGTCCGCA AGCTAGATCA
    ACGGCACTGT CGGCACCGGG ACGTCGAGTA CGGACAACTC TAGCAGGCGT TCGATCTAGT
         9070       9080       9090       9100       9110       9120
    GTCGGACTGG GTGCGGGGTG CCTGGATCGT GTCAGAGACT TTTCCAACTA GCGACCCCAA
    CAGCCTGACC CACGCCCCAC GGACCTAGCA CAGTCTCTGA AAAGGTTGAT CGCTGGGGTT
         9130       9140       9150       9160       9170       9180
    AGGAGTTTGG AGCGACGATG ACTCCTCGAT GGGTGGAAGT GATGATTGAT GATGAGAACC
    TCCTCAAACC TCGCTGCTAC TGAGGAGCTA CCCACCTTCA CTACTAACTA CTACTCTTGG
```

Fig. 11 (SEQ ID NO: 1)

```
        9190       9200       9210       9220       9230       9240
    TGACAAGAAA GACGAGAGAG AAATTTAGAG CTGTCATTGT AGAATTAGTC TAGATTCCTG
    ACTGTTCTTT CTGCTCTCTC TTTAAATCTC GACAGTAACA TCTTAATCAG ATCTAAGGAC
        9250       9260       9270       9280       9290       9300
    ATAATAAACA GTATCGATTT TGAAACCTAA TTGACGTGTG ATCGATTTTT AAACCTCTGT
    TATTATTTGT CATAGCTAAA ACTTTGGATT AACTGCACAC TAGCTAAAAA TTTGGAGACA
        9310       9320       9330       9340       9350       9360
    GTTGTGTGAT TGATTGGTAT GTGGGGGGAT CCGATTCAA AGGGGGGTAC TTATCGGGAA
    CAACACACTA ACTAACCATA CACCCCCCTA GGCTAAAGTT TCCCCCCATG AATAGCCCTT
        9370       9380       9390       9400       9410       9420
    TTGATGTGTC ATGGACGCAG TTTTGAGCGA TTTTCCGGGA ATACCGGATA TTACGAATTA
    AACTACACAG TACCTGCGTC AAAACTCGCT AAAAGGCCCT TATGGCCTAT AATGCTTAAT
        9430       9440       9450       9460       9470       9480
    CTGGTAGTGA CGTAGATAAT AAAATTATAA TGCGATTAAT TTTTGGTGCG TTGATTATTT
    GACCATCACT GCATCTATTA TTTTAATATT ACGCTAATTA AAAACCACGC AACTAATAAA
        9490       9500       9510       9520       9530       9540
    TTTTAGCATA TGTGTATCAT TATGAGGTGA ATGGAACAGA ATTACGCTGC AGATGTCTTC
    AAAATCGTAT ACACATAGTA ATACTCCACT TACCTTGTCT TAATGCGACG TCTACAGAAG
        9550       9560       9570       9580       9590       9600
    ATAGAAAATG GCCGCCTAAT AAAATTATAT TGGGTAATTA TTGGCTTCAT CGCGATCCCA
    TATCTTTTAC CGGCGGATTA TTTTAATATA ACCCATTAAT AACCGAAGTA GCGCTAGGGT
        9610       9620       9630       9640       9650       9660
    GAGGGCCCGG ATGCGATAAA AATGAACATT TATTGTATCC AGACGGAAGG AAACCGCCTG
    CTCCCGGGCC TACGCTATTT TTACTTGTAA ATAACATAGG TCTGCCTTCC TTTGGCGGAC
        9670       9680       9690       9700       9710       9720
    GACCTGGAGT ATGTTTATCG CCCGATCACC TCTTCTCAAA ATGGTTAGAC AAACACAACG
    CTGGACCTCA TACAAATAGC GGGCTAGTGG AGAAGAGTTT TACCAATCTG TTTGTGTTGC
        9730       9740       9750       9760       9770       9780
    ATAATAGGTG GTATAATGTT AACATAACGA AATCACCAGG ACCGAGACGA ATAAATATAA
    TATTATCCAC CATATTACAA TTGTATTGCT TTAGTGGTCC TGGCTCTGCT TATTTATATT
        9790       9800       9810       9820       9830       9840
    CCTTGATAGG TGTTAGAGGA TAATATTTAA TGTATGTTTT CAAACAGACA AGTTCGTTAA
    GGAACTATCC ACAATCTCCT ATTATAAATT ACATACAAAA GTTTGTCTGT TCAAGCAATT
        9850       9860       9870       9880       9890       9900
    AACAAAATAT TACAGTATGT GTTTAATATG GTGCTAACAT GGTTGCACCA TCCGGTTTCA
    TTGTTTTATA ATGTCATACA CAAATTATAC CACGATTGTA CCAACGTGGT AGGCCAAAGT
        9910       9920       9930       9940       9950       9960
    AACTCGCATA TCAATCTGTT ATCGGTACGA CACCTGTCAT TAATCGCATA TATGTTACTT
    TTGAGCGTAT AGTTAGACAA TAGCCATGCT GTGGACAGTA ATTAGCGTAT ATACAATGAA
        9970       9980       9990      10000      10010      10020
    ACCATATGTC CCCTAGCCGT CCATGTTTTA GAACTAGAAG ATTACGACAG GCGCTGCCGT
    TGGTATACAG GGGATCGGCA GGTACAAAAT CTTGATCTTC TAATGCTGTC CGCGACGGCA
       10030      10040      10050      10060      10070      10080
    TGCAACAACC AAATTCTGTT GAATACCCTG CCGGTCGGAA CCGAATTGCT TAAGCCAATC
    ACGTTGTTGG TTTAAGACAA CTTATGGGAC GGCCAGCCTT GGCTTAACGA ATTCGGTTAG
       10090      10100      10110      10120      10130      10140
    GCAGCGAGCG AAAGCTGCAA TCGTCAGGAA GTGCTGGCTA TTTTAAAGGA CAAGGGAACC
    CGTCGCTCGC TTTCGACGTT AGCAGTCCTT CACGACCGAT AAAATTTCCT GTTCCCTTGG
       10150      10160      10170      10180      10190      10200
    AAGTGTCTCA ATCCTAACGC GCAAGCCGTG CGTCGTCACA TCAACCGGCT ATTTTTTCGG
    TTCACAGAGT TAGGATTGCG CGTTCGGCAC GCAGCAGTGT AGTTGGCCGA TAAAAAAGCC
```

Fig. 1J (SEQ ID NO: 1)

```
       10210      10220      10230      10240      10250      10260
TTAATCTTAG ACGAGGAACA ACGCATTTAC GACGTAGTGT CTACCAATAT TGAGTTCGGT
AATTAGAATC TGCTCCTTGT TGCGTAAATG CTGCATCACA GATGGTTATA ACTCAAGCCA
       10270      10280      10290      10300      10310      10320
GCCTGGCCAG TCCCTACGGC CTACAAAGCC TTTCTTTGGA AATACGCCAA GAGACTGAAC
CGGACCGGTC AGGGATGCCG GATGTTTCGG AAAGAAACCT TTATGCGGTT CTCTGACTTG
       10330      10340      10350      10360      10370      10380
TACCACCACT TCAGACTGCG CTGGTGATCA TGTCCCTATT TTACCGTGCG GTAGCTCTGG
ATGGTGGTGA AGTCTGACGC GACCACTAGT ACAGGGATAA AATGGCACGC CATCGAGACC
       10390      10400      10410      10420      10430      10440
GCACGCTAAG CGCTTTGGTG TGGTACAGCA CTAGCATCCT CGCAGAGATT AACGAAAATT
CGTGCGATTC GCGAAACCAC ACCATGTCGT GATCGTAGGA GCGTCTCTAA TTGCTTTTAA
       10450      10460      10470      10480      10490      10500
CCTGCTCCTC ATCTTCTGCG GATCACGAAG ACTGCGAGGA ACCGGACGAG ATCGTTCGCG
GGACGAGGAG TAGAAGACGC CTAGTGCTTC TGACGCTCCT TGGCCTGCTC TAGCAAGCGC
       10510      10520      10530      10540      10550      10560
AAGAGCAAGA CTATCGGGCT CTGCTGGCCT TTTCCCTAGT GATTTGCGGT ACGCTCCTCG
TTCTCGTTCT GATAGCCCGA GACGACCGGA AAAGGGATCA CTAAACGCCA TGCGAGGAGC
       10570      10580      10590      10600      10610      10620
TCACTTGTGT GATCTGAGAC GTCATGCTGG TAGCGTTTAT GAGTCGGGCG GTGGCCGACA
AGTGAACACA CTAGACTCTG CAGTACGACC ATCGCAAATA CTCAGCCCGC CACCGGCTGT
       10630      10640      10650      10660      10670      10680
CGCCGCATTT CCTAACCCGC GCAGCATGTT GCGCTTGCTG TTCACGCTCG TCCTGCTGGC
GCGGCGTAAA GGATTGGGCG CGTCGTACAA CGCGAACGAC AAGTGCGAGC AGGACGACCG
       10690      10700      10710      10720      10730      10740
CCTCCACGGG CAGTCTGTCG GCGCTAGCCG CGACTATGTG CATGTTCGGC TACTGAGCTA
GGAGGTGCCC GTCAGACAGC CGCGATCGGC GCTGATACAC GTACAAGCCG ATGACTCGAT
       10750      10760      10770      10780      10790      10800
CCGAGGCGAC CCCCTGGTCT TCAAGCACAC TTTCTCGGGT GTGCGTCGAC CCTTCACCGA
GGCTCCGCTG GGGGACCAGA AGTTCGTGTG AAAGAGCCCA CACGCAGCTG GGAAGTGGCT
       10810      10820      10830      10840      10850      10860
GCTAGGCTGG GCTGCGTGTC GCGACTGGGA CAGTATGCAT TGCACACCCT TCTGGTCTAC
CGATCCGACC CGACGCACAG CGCTGACCCT GTCATACGTA ACGTGTGGGA AGACCAGATG
       10870      10880      10890      10900      10910      10920
CGATCTGGAG CAGATGACCG ACTCGGTGCG GCGTTACAGC ACGGTGAGCC CCGGCAAGGA
GCTAGACCTC GTCTACTGGC TGAGCCACGC CGCAATGTCG TGCCACTCGG GGCCGTTCCT
       10930      10940      10950      10960      10970      10980
AGTGACGCTT CAGCTTCACG GGAACCAAAC CGTACAGCCG TCGTTTCTAA GCTTTACGTG
TCACTGCGAA GTCGAAGTGC CCTTGGTTTG GCATGTCGGC AGCAAAGATT CGAAATGCAC
       10990      11000      11010      11020      11030      11040
CCGCCTGCAG CTAGAACCCG TGGTGGAAAA TGTTGGCCTC TACGTGGCCT ACGTGGTCAA
GGCGGACGTC GATCTTGGGC ACCACCTTTT ACAACCGGAG ATGCACCGGA TGCACCAGTT
       11050      11060      11070      11080      11090      11100
CGACGGCGAA CGCCCACAAC AGTTTTTTAC ACCGCAGGTA GACGTGGTAC GCTTTGCTCT
GCTGCCGCTT GCGGGTGTTG TCAAAAAATG TGGCGTCCAT CTGCACCATG CGAAACGAGA
       11110      11120      11130      11140      11150      11160
ATATCTAGAA ACACTCTCCC GGATCGTGGA ACCGTTAGAA TCAGGTCGCC TGGCAGTGGA
TATAGATCTT TGTGAGAGGG CCTAGCACCT TGGCAATCTT AGTCCAGCGG ACCGTCACCT
       11170      11180      11190      11200      11210      11220
ATTTGATACG CCTGACCTAG CTCTGGCGCC CGATTTAGTA AGCAGCCTCT TCGTGGCCGG
TAAACTATGC GGACTGGATC GAGACCGCGG GCTAAATCAT TCGTCGGAGA AGCACCGGCC
```

Fig. 1K (SEQ ID NO: 1)

```
       11230      11240      11250      11260      11270      11280
  ACACGGCGAG ACCGACTTTT ACATGAACTG GACGCTGCGT CGCAGTCAGA CCCACTACCT
  TGTGCCGCTC TGGCTGAAAA TGTACTTGAC CTGCGACGCA GCGTCAGTCT GGGTGATGGA
       11290      11300      11310      11320      11330      11340
  GGAGGAGATG GCCTTACAGG TGGAGATTCT AAAACCCCGC GGCGTACGTC ACCGCGCTAT
  CCTCCTCTAC CGGAATGTCC ACCTCTAAGA TTTTGGGGCG CCGCATGCAG TGGCGCGATA
       11350      11360      11370      11380      11390      11400
  TATCCACCAT CCGAAGCTAC AGCCGGGCGT TGGCCTGTGG ATAGATTTCT GCGTGTACCG
  ATAGGTGGTA GGCTTCGATG TCGGCCCGCA ACCGGACACC TATCTAAAGA CGCACATGGC
       11410      11420      11430      11440      11450      11460
  CTACAACGCG CGCCTGACCC GCGGCTACGT ACGATACACC CTGTCACCGA AAGCGCGCTT
  GATGTTGCGC GCGGACTGGG CGCCGATGCA TGCTATGTGG GACAGTGGCT TTCGCGCGAA
       11470      11480      11490      11500      11510      11520
  GCCCGCAAAA GCAGAGGGTT GGCTGGTGTC ACTAGACAGA TTCATCGTGC AGTACCTCAA
  CGGGCGTTTT CGTCTCCCAA CCGACCACAG TGATCTGTCT AAGTAGCACG TCATGGAGTT
       11530      11540      11550      11560      11570      11580
  CACATTGCTG ATTACAATGA TGGCGGCGAT ATGGGCTCGC GTTTTGATAA CCTACCTGGT
  GTGTAACGAC TAATGTTACT ACCGCCGCTA TACCCGAGCG CAAAACTATT GGATGGACCA
       11590      11600      11610      11620      11630      11640
  GTCGCGGCGT CGGTAGAGGC TTGCGGAAAC CACGTCCTCG TCACACGTCG TTCGCGGACA
  CAGCGCCGCA GCCATCTCCG AACGCCTTTG GTGCAGGAGC AGTGTGCAGC AAGCGCCTGT
       11650      11660      11670      11680      11690      11700
  TAGCAAGAAA TCCACGTCGC CACATCTCGA GAATGCCGGC CTTGCGGGGT CCCCTTCGCG
  ATCGTTCTTT AGGTGCAGCG GTGTAGAGCT CTTACGGCCG GAACGCCCCA GGGGAAGCGC
       11710      11720      11730      11740      11750      11760
  CAACATTCCT GGCCCTGGTC GCGTTCGGGT TGCTGCTTCA GATAGACCTC AGCGACGCTA
  GTTGTAAGGA CCGGGACCAG CGCAAGCCCA ACGACGAAGT CTATCTGGAG TCGCTGCGAT
       11770      11780      11790      11800      11810      11820
  CGAATGTGAC CAGCAGCACA AAAGTCCCTA CTAGCACCAG CAACAGAAAT AACGTCGACA
  GCTTACACTG GTCGTCGTGT TTTCAGGGAT GATCGTGGTC GTTGTCTTTA TTGCAGCTGT
       11830      11840      11850      11860      11870      11880
  ACGCCACGAG TAGCGGACCC ACAACCGGGA TCAACATGAC CACCACCCAC GAGTCTTCCG
  TGCGGTGCTC ATCGCCTGGG TGTTGGCCCT AGTTGTACTG GTGGTGGGTG CTCAGAAGGC
       11890      11900      11910      11920      11930      11940
  TTCACAACGT GCGCAATAAC GAGATCATGA AAGTGCTGGC TATCCTCTTC TACATCGTGA
  AAGTGTTGCA CGCGTTATTG CTCTAGTACT TTCACGACCG ATAGGAGAAG ATGTAGCACT
       11950      11960      11970      11980      11990      12000
  CAGGCACCTC CATTTTCAGC TTCATAGCGG TACTGATCGC GGTAGTTTAC TCCTCGTGTT
  GTCCGTGGAG GTAAAAGTCG AAGTATCGCC ATGACTAGCC CCATCAAATG AGGAGCACAA
       12010      12020      12030      12040      12050      12060
  GCAAGCACCC GGGCCGCTTT CGTTTCGCCC ACGAAGAGGC CGTCAACCTG TTGGACGACA
  CGTTCGTGGG CCCGGCGAAA GCAAAGCGGC TGCTTCTCCG GCAGTTGGAC AACCTGCTGT
       12070      12080      12090      12100      12110      12120
  CGGACGACAG TGGCGGCAGC AGCCCGTTTG GCAGCGGTTC CCGACGAGGT TCTCAGATCC
  GCCTGCTGTC ACCGCCGTCG TCGGGCAAAC CGTCGCCAAG GCTGCTCCA AGAGTCTAGG
       12130      12140      12150      12160      12170      12180
  CCGCCGGATT TTGTTCCTCG AGCCCTTATC AGCGGTTGGA AACTCGGGAC TGGGACGAGG
  GGCGGCCTAA AACAAGGAGC TCGGGAATAG TCGCCAACCT TTGAGCCCTG ACCCTGCTCC
       12190      12200      12210      12220      12230      12240
  AGGAGGAGGC GTCCGCGGCC CGCGAGCGCA TGAAACATGA TCCTGAGAAC GTCATCTATT
  TCCTCCTCCG CAGGCGCCGG GCGCTCGCGT ACTTTGTACT AGGACTCTTG CAGTAGATAA
```

Fig. 1L (SEQ ID NO: 1)

```
           12250      12260      12270      12280      12290      12300
       TCAGAAAGGA TGGCAACTTG GACACGTCGT TCGTGAATCC CAATTATGGG AGAGGCTCGC
       AGTCTTTCCT ACCGTTGAAC CTGTGCAGCA AGCACTTAGG GTTAATACCC TCTCCGAGCG
           12310      12320      12330      12340      12350      12360
       CTTTGACCAT CGAATCTCAC CTCTCGGACA ATGAGGAGGA CCCCATCAGG TACTACGTTT
       GAAACTGGTA GCTTAGAGTG GAGAGCCTGT TACTCCTCCT GGGGTAGTCC ATGATGCAAA
           12370      12380      12390      12400      12410      12420
       CGGTGTACGA TGAACTGACC GCCTCGGAAA TGGAAGAACC TTCGAACAGC ACCAGCTGGC
       GCCACATGCT ACTTGACTGG CGGAGCCTTT ACCTTCTTGG AAGCTTGTCG TGGTCGACCG
           12430      12440      12450      12460      12470      12480
       AGATTCCCAA ACTAATGAAA GTTGCCATGC AACCCGTCTC GCTCAGAGAT CCCGAGTACG
       TCTAAGGGTT TGATTACTTT CAACGGTACG TTGGGCAGAG CGAGTCTCTA GGGCTCATGC
           12490      12500      12510      12520      12530      12540
       ACTAGGCTTT TTTTTTTGTC TTTCGGTTCC AACTCTTTCC CCGCCCCATC ACCTCGCCTG
       TGATCCGAAA AAAAAAACAG AAAGCCAAGG TTGAGAAAGG GGCGGGGTAG TGGAGCGGAC
           12550      12560      12570      12580      12590      12600
       TACTATGTGT ATGATGTCTC ATAATAAAGC TTTCTTTCTC AGTCTGCAAC ATGCAGCTGT
       ATGATACACA TACTACGAGA TATTATTTCG AAAGAAAGAG TCAGACGTTG TACGTCGACA
           12610      12620      12630      12640      12650      12660
       GTCGGGTGTG GCTGTCTGTT TGTCTGTGCG CCGTGGTGCT GGGTCAGTGC CAGCGGGAAA
       CAGCCCACAC CGACAGACAA ACAGACACGC GGCACCACGA CCCAGTCACG GTCGCCCTTT
           12670      12680      12690      12700      12710      12720
       CCGCGGAAAA AAACGATTAT TACCGAGTAC CGCATTACTG GGACGCGTGC TCTCGCGCGC
       GGCGCCTTTT TTTGCTAATA ATGGCTCATG GCGTAATGAC CCTGCGCACG AGAGCGCGCG
           12730      12740      12750      12760      12770      12780
       TGCCCGACCA AACCCGTTAC AAGTATGTGG AACAGCTCGT GGACCTCACG TTGAACTACC
       ACGGGCTGGT TTGGGCAATG TTCATACACC TTGTCGAGCA CCTGGAGTGC AACTTGATGG
           12790      12800      12810      12820      12830      12840
       ACTACGATGC GAGCCACGGC TTGGACAACT TTGACGTGCT CAAGAGGTGA GGGTACGCGC
       TGATGCTACG CTCGGTGCCG AACCTGTTGA AACTGCACGA GTTCTCCACT CCCATGCGCG
           12850      12860      12870      12880      12890      12900
       TAAAGGTGCA TGACAACGGG AAGGTAAGGG CGAACGGGTA ACGGCTAAGT AACCGCATGG
       ATTTCCACGT ACTGTTGCCC TTCCATTCCC GCTTGCCCAT TGCCGATTCA TTGGCGTACC
           12910      12920      12930      12940      12950      12960
       GGTATGAAAT GACGTTTGGA ACCTGTGCTT GCAGAATCAA CGTGACCGAG GTGTCGTTGC
       CCATACTTTA CTGCAAACCT TGGACACGAA CGTCTTAGTT GCACTGGCTC CACAGCAACG
           12970      12980      12990      13000      13010      13020
       TCATCAGCGA CTTTAGACGT CAGAACCGTC GCGGCGGCAC CAACAAAAGG ACCACGTTCA
       AGTAGTCGCT GAAATCTGCA GTCTTGGCAG CGCCGCCGTG GTTGTTTTCC TGGTGCAAGT
           13030      13040      13050      13060      13070      13080
       ACGCCGCCGG TTCGCTGGCG CCACACGCCC GGAGCCTCGA GTTCAGCGTG CGGCTCTTTG
       TGCGGCGGCC AAGCGACCGC GGTGTGCGGG CCTCGGAGCT CAAGTCGCAC GCCGAGAAAC
           13090      13100      13110      13120      13130      13140
       CCAACTAGCC TGCGTCACGG GAAATAATAT GCTGCGGCTT CTGCTTCGTC ACCACTTTCA
       GGTTGATCGG ACGCAGTGCC CTTTATTATA CGACGCCGAA GACGAAGCAG TGGTGAAAGT
           13150      13160      13170      13180      13190      13200
       CTGCCTGCTT CTGTGCGCGG TTTGGGCAAC GCCCTGTCTG GCGTCTCCGT GGTCGACGCT
       GACGGACGAA GACACGCGCC AAACCCGTTG CGGGACAGAC CGCAGAGGCA CCAGCTGCGA
           13210      13220      13230      13240      13250      13260
       AACGGCAAAC CAGAATCCGT CCCCGCCATG GTCTAAACTG ACGTATTCCA AACCGCATGA
       TTGCCGTTTG GTCTTAGGCA GGGGCGGTAC CAGATTTGAC TGCATAAGGT TTGGCGTACT
```

Fig. 1M (SEQ ID NO: 1)

```
         13270      13280      13290      13300      13310      13320
     CGCGGCGACG TTTTACTGTC CTTTTCTCTA TCCCTCGCCC CCACGGTCCC CCTTGCAATT
     GCGCCGCTGC AAAATGACAG GAAAAGAGAT AGGGAGCGGG GGTGCCAGGG GGAACGTTAA
         13330      13340      13350      13360      13370      13380
     CTCGGGGTTC CAGCAGGTAT CAACGGGTCC CGAGTGTCGC AACGAGACCC TGTATCTGCT
     GAGCCCCAAG GTCGTCCATA GTTGCCCAGG GCTCACAGCG TTGCTCTGGG ACATAGACGA
         13390      13400      13410      13420      13430      13440
     GTACAACCGG GAAGGCCAGA CCTTGGTGGA GAGAAGCTCC ACCTGGGTGA AAAAGGTGAT
     CATGTTGGCC CTTCCGGTCT GGAACCACCT CTCTTCGAGG TGGACCCACT TTTTCCACTA
         13450      13460      13470      13480      13490      13500
     CTGGTATCTG AGCGGTCGCA ACCAGACCAT CCTCCAACGG ATGCCCCAAA CGGCTTCGAA
     GACCATAGAC TCGCCAGCGT TGGTCTGGTA GGAGGTTGCC TACGGGGTTT GCCGAAGCTT
         13510      13520      13530      13540      13550      13560
     ACCGAGCGAC GGAAACGTGC AGATCAGCGT GGAAGACGCC AAGATTTTTG GAGCGCACAT
     TGGCTCGCTG CCTTTGCACG TCTAGTCGCA CCTTCTGCGG TTCTAAAAAC CTCGCGTGTA
         13570      13580      13590      13600      13610      13620
     GGTGCCCAAG CAGACCAAGC TGCTACGCTT CGTCGTCAAC GATGGCACGC GTTATCAGAT
     CCACGGGTTC GTCTGGTTCG ACGATGCGAA GCAGCAGTTG CTACCGTGCG CAATAGTCTA
         13630      13640      13650      13660      13670      13680
     GTGTGTGATG AAGCTGGAGA GCTGGGCCCA CGTCTTCCGG GACTACAGCG TGTCTTTTCA
     CACACACTAC TTCGACCTCT CGACCCGGGT GCAGAAGGCC CTGATGTCGC ACAGAAAAGT
         13690      13700      13710      13720      13730      13740
     GGTGCGATTG ACGTTCACCG AGGCCAATAA CCAGACTTAC ACCTTCTGTA CCCATCCCAA
     CCACGCTAAC TGCAAGTGGC TCCGGTTATT GGTCTGAATG TGGAAGACAT GGGTAGGGTT
         13750      13760      13770      13780      13790      13800
     TCTCATCATT TGAGCCCGTC GCGCGCGCAG GGAATTTTGA AAACCGCGCG TCATGAGTCC
     AGAGTAGTAA ACTCGGGCAG CGCGCGCGTC CCTTAAAACT TTTGGCGCGC AGTACTCAGG
         13810      13820      13830      13840      13850      13860
     CAAAGACCTG ACGCCGTTCT TGACGACGTT GTGGCTGCTA TTGGGTCACA GCCGCGTGCC
     GTTTCTGGAC TGCGGCAAGA ACTGCTGCAA CACCGACGAT AACCCAGTGT CGGCGCACGG
         13870      13880      13890      13900      13910      13920
     GCGGGTGCGC GCAGAAGAAT GTTGCGAATT CATAAACGTC AACCACCCGC CGGAACGCTG
     CGCCCACGCG CGTCTTCTTA CAACGCTTAA GTATTTGCAG TTGGTGGGCG GCCTTGCGAC
         13930      13940      13950      13960      13970      13980
     TTACGATTTC AAAATGTGCA ATCGCTTCAC CGTCGCGTAC GTATTTTCAT GATTGTCTGC
     AATGCTAAAG TTTTACACGT TAGCGAAGTG GCAGCGCATG CATAAAAGTA CTAACAGACG
         13990      14000      14010      14020      14030      14040
     GTTCTGTGGT GCGTCTGGAT TTGTCTCTCG ACGTTTCTGA TAGCCATGTT CCATCGACGA
     CAAGACACCA CGCAGACCTA AACAGAGAGC TGCAAAGACT ATCCGGTACA GGTAGCTGCT
         14050      14060      14070      14080      14090      14100
     TCCTCGGGAA TGCCAGAGTA GATTTTCATG AATCCACAGG CTGCGGTGTC CGGACGGCGA
     AGGAGCCCTT ACGGTCTCAT CTAAAAGTAC TTAGGTGTCC GACGCCACAG GCCTGCCGCT
         14110      14120      14130      14140      14150      14160
     AGTCTGCTAC AGTCCCGAGA AAACGGCTGA GATTCGCGGG ATCGTCACCA CCATGACCCA
     TCAGACGATG TCAGGGCTCT TTTGCCGACT CTAAGCGCCC TAGCAGTGGT GGTACTGGGT
         14170      14180      14190      14200      14210      14220
     TTCATTGACA CGCCAGGTCG TACACAACAA ACTGACGAGC TGCAACTACA ATCCGTAAGT
     AAGTAACTGT GCGGTCCAGC ATGTGTTGTT TGACTGCTCG ACGTTGATGT TAGGCATTCA
         14230      14240      14250      14260      14270      14280
     CTCTTCCTCG AGGGCCTTAC AGCCTATGGG AGAGTAAGAC AGAGAGGGAC AAAACATCAT
     GAGAAGGAGC TCCCGGAATG TCGGATACCC TCTCATTCTG TCTCTCCCTG TTTTGTAGTA
```

Fig. 1N (SEQ ID NO: 1)

```
       14290      14300      14310      14320      14330      14340
   TAAAAAAAAA AGTCTAATTT CACGTTTTGT ACCCCCCTTC CCCTCCGTGT TGTAGCCCAT
   ATTTTTTTTT TCAGATTAAA GTGCAAAACA TGGGGGGAAG GGGAGGCACA ACATCGGGTA
       14350      14360      14370      14380      14390      14400
   CGGCCGCGGC GATCTCCTAG TAACACTCGT CCGACACTTC CACCATCTCC AGCTCGGCCG
   GCCGGCGCCG CTAGAGGATC ATTGTGAGCA GGCTGTGAAG GTGGTAGAGG TCGAGCCGGC
       14410      14420      14430      14440      14450      14460
   GCGGTTCGGC ATCCTCTACC AGCGGCGTCG TCTCATCTTT GCCGCAGCAG CGGACGCACA
   CGCCAAGCCG TAGGAGATGG TCGCCGCAGC AGAGTAGAAA CGGCGTCGTC GCCTGCGTGT
       14470      14480      14490      14500      14510      14520
   CCTTCTCCAG GCAGAACGCC ACCAGCTGCC GCCGAACGTA CCACAGGTAC ACGTGCAGAC
   GGAAGAGGTC CGTCTTGCGG TGGTCGACGG CGGCTTGCAT GGTGTCCATG TGCACGTCTG
       14530      14540      14550      14560      14570      14580
   CTGCGAACAG GACTACGGAG GTCATGACCA CCACGACGCA CACGGGAATC CAGGGATCGA
   GACGCTTGTC CTGATGCCTC CAGTACTGGT GGTGCTGCGT GTGCCCTTAG GTCCCTAGCT
       14590      14600      14610      14620      14630      14640
   GATTGTTGCT GGAACTCATG GCTATCGCCA CCGACGTGCC CGCGTCTGTC TCACCGCCGC
   CTAACAACGA CCTTGAGTAC CGATAGCGGT GGCTGCACGG GCGCAGACAG AGTGGCGGCG
       14650      14660      14670      14680      14690      14700
   TCGCCCGATG TCGCGCGGCT TGTTATACGC TAGCCCGTCG CCGCCTCGGG GCACGGTGCC
   AGCGGGCTAC AGCGCGCCGA ACAATATGCG ATCGGGCAGC GGCGGAGCCC CGTGCCACGG
       14710      14720      14730      14740      14750      14760
   CTCCTACCCA CGTAACTTCC TCCGTGACTT AAAGTCGCGT GTGGTAGATC TCCTGCTCCG
   GAGGATGGGT GCATTGAAGG AGGCACTGAA TTTCAGCGCA CACCATCTAG AGGACGAGGC
       14770      14780      14790      14800      14810      14820
   TGGACGAACC GTCCGGCAGG ATAGCGGTTA AGGATTCGGT GCTAAGGCCG TGTCGCCAAC
   ACCTGCTTGG CAGGCCGTCC TATCGCCAAT TCCTAAGCCA CGATTCCGGC ACAGCGGTTG
       14830      14840      14850      14860      14870      14880
   GTCGAATGCT ACGTTGCAAC AGCTTGACG GACGGCCATC CCCTCTCTCA TCGCAATAAT
   CAGCTTACGA TGCAACGTTG TCGAAGCTGC CTGCCGGTAG GGGAGAGAGT AGCGTTATTA
       14890      14900      14910      14920      14930      14940
   AAAACACCAG CAGCGCGCAC GACGCGATCA CGGTGACACC CATGATTAGA CCCACGCAGA
   TTTTGTGGTC GTCGCGCGTG CTGCGCTAGT GCCACTGTGG GTACTAATCT GGGTGCGTCT
       14950      14960      14970      14980      14990      15000
   TAGCCAGCCC CGCTAGCGTA TCTAGCGCCA TCCCGTTCGC TCCCGTTGTC TCCTGAGCGA
   ATCGGTCGGG GCGATCGCAT AGATCGCGGT AGGGCAAGCG AGGGCAACAG AGGACTCGCT
       15010      15020      15030      15040      15050      15060
   AGCAACTTCT CGGTCCCCGT TTTCAACAGT TTTTGTTTCC TTCTCCGCGA CTAGATGTTA
   TCGTTGAAGA GCCAGGGGCA AAAGTTGTCA AAAACAAAGG AAGAGGCGCT GATCTACAAT
       15070      15080      15090      15100      15110      15120
   ACGCCCGCGG TCTTTCCGGC CGTGCTCTAC CTCCTGGCGC TTGTCGTCTG GGTTGAGATG
   TGCGGGCGCC AGAAAGGCCG GCACGAGATG GAGGACCGCG AACAGCAGAC CCAACTCTAC
       15130      15140      15150      15160      15170      15180
   TTCTGCCTCG TCGCCGTAGC CGTCGTCGAG CGCGAGATCG CCTGGGCGCT GCTGCTGCGG
   AAGACGGAGC AGCGGCATCG GCAGCAGCTC GCGCTCTAGC GGACCCGCGA CGACGACGCC
       15190      15200      15210      15220      15230      15240
   ATGCTGGTCG TTGGCCTGAT GGTGGAAGTC GGCGCCGCCG CCGCTTGGAC CTTCGTGCGT
   TACGACCAGC AACCGGACTA CCACCTTCAG CCGCGGCGGC GGCGAACCTG GAAGCACGCA
       15250      15260      15270      15280      15290      15300
   TGTCTTGCCT ATCAGCGCTC CTTCCCCGTG CTTACGGCCT TCCCCTGAAA CCCACGTTAA
   ACAGAACGGA TAGTCGCGAG GAAGGGGCAC GAATGCCGGA AGGGGACTTT GGGTGCAATT
```

Fig. 1O (SEQ ID NO: 1)

```
         15310      15320      15330      15340      15350      15360
     CCGACCGTCC CAAAAACGCC GGTGTTAACA CAGGAAAAAA AGAAACCACG CAGGAACCGC
     GGCTGGCAGG GTTTTTGCGG CCACAATTGT GTCCTTTTTT TCTTTGGTGC GTCCTTGGCG 15370      15380      15390      15400      15410      15420
     GCAGGAACCA CGCGGAACAT GGGACACTAT CTGGAAATCC TGTTCAACGT CATCGTCTTC
     CGTCCTTGGT GCGCCTTGTA CCCTGTGATA GACCTTTAGG ACAAGTTGCA GTAGCAGAAG 15430      15440      15450      15460      15470      15480
     ACTCTGCTGC TCGGCGTCAT GGTCAGTATC GTCGCTTGGT ACTTCACGTG AACCACCGTC
     TGAGACGACG AGCCGCAGTA CCAGTCATAG CAGCGAACCA TGAAGTGCAC TTGGTGGCAG 15490      15500      15510      15520      15530      15540
     GTCCCGGTTT AAAAACCATC ATCGACGGCC GTTATAAAGC CACCCGGACA CGCGCCGCGG
     CAGGGCCAAA TTTTTGGTAG TAGCTGCCGG CAATATTTCG GTGGGCCTGT GCGCGGCGCC 15550      15560      15570      15580      15590      15600
     CACTTGCCTA CGGCGCTGCT TCAGGGAAAC TCCTCTTCCT TCTGCTCTTC CTCCTTCACC
     GTGAACGGAT GCCGCGACGA AGTCCCTTTG AGGAGAAGGA AGACGAGAAG GAGGAAGTGG 15610      15620      15630      15640      15650      15660
     GCAGGGATCG TTTCCCTCGA CCAGGGACTC GCCGAAGCAA CCGCCGGAGC AACCTGGAGG
     CGTCCCTAGC AAAGGGAGCT GGTCCCTGAG CGGCTTCGTT GGCGGCCTCG TTGGACCTCC 15670      15680      15690      15700      15710      15720
     AGTCGCGGCA TGACGGCGCC CAAGTGTGTC ACCACCAGTA CTTATCTGGT CAAGACCAAG
     TCAGCGCCGT ACTGCCGCGG GTTCACACAG TGGTGGTCAT GAATAGACCA GTTCTGGTTC 15730      15740      15750      15760      15770      15780
     GAACAGCCCT GGTGGCCCGA CAACGCCATC AGGAGATGGT GGATCAGTGT TGCTATCGTC
     CTTGTCGGGA CCACCGGGCT GTTGCGGTAG TCCTCTACCA CCTAGTCACA ACGATAGCAG 15790      15800      15810      15820      15830      15840
     ATCTTCATCG GAGTCTGTCT GGTGGCCCTG ATGTACTTTA CGCAGCAGCA GGCACGCAGC
     TAGAAGTAGC CTCAGACAGA CCACCGGGAC TACATGAAAT GCGTCGTCGT CCGTGCGTCG 15850      15860      15870      15880      15890      15900
     GGGAGCAGCA GCGGCTAGAC AAGTCTCTGG CGGCTACAGC TCCAAGCGCC GTAGCCGGGC
     CCCTCGTCGT CGCCGATCTG TTCAGAGACC GCCGATGTCG AGGTTCGCGG CATCGGCCCG 15910      15920      15930      15940      15950      15960
     CGCCTGCCGA TCGCGACGTC GTGGACCATC GAACAGAGAC TCACGCGTAC GAGACCCGA
     GCGGACGGCT AGCGCTGCAG CACCTGGTAG CTTGTCTCTG AGTGCGCATG CTCTGGGGCT 15970      15980      15990      16000      16010      16020
     GGTACGCCAC GCGGTGCCTA ACGCGGTATA CCACACCCGT ACGGTCTGCA GTGCGGCGTA
     CCATGCGGTG CGCCACGGAT TGCGCCATAT GGTGTGGGCA TGCCAGACGT CACGCCGCAT 16030      16040      16050      16060      16070      16080
     CAACGTGTGG AAAACGCGTT GCGTCGCAGA GTCCGCCACG TTCCTGTCTT GTCGCTCCCC
     GTTGCACACC TTTTGCGCAA CGCAGCGTCT CAGGCGGTGC AAGGACAGAA CAGCGAGGGG 16090      16100      16110      16120      16130      16140
     AATCGTCTCC CGCACACCCC CCGCGACACC CAGAGGGCGG GTGAGCCAAG TATTCTTAAG
     TTAGCAGAGG GCGTGTGGGG GGCGCTGTGG GTCTCCCGCC CACTCGGTTC ATAAGAATTC 16150      16160      16170      16180      16190      16200
     GCCGTTCTTT GTTCCATAGC CCATAAATTG TTGATTCCGG AGCTCGTTGG CGCGGAAATA
     CGGCAAGAAA CAAGGTATCG GGTATTTAAC AACTAAGGCC TCGAGCAACC GCGCCTTTAT 16210      16220      16230      16240      16250      16260
     GCCGGATAAG GGGAGCAACA ACCGTTGGCG AAAGCCGTCC CGCTCATTCA GTCCGGGTTT
     CGGCCTATTC CCCTCGTTGT TGGCAACCGC TTTCGGCAGG GCGAGTAAGT CAGGCCCAAA 16270      16280      16290      16300      16310      16320
     CGCGTCCAGT CGGACGTGTG ACCGTTGGGC AACGGAACGG CGTTTCACTG CCAAAATCGT
     GCGCAGGTCA GCCTGCACAC TGGCAACCCG TTGCCTTGCC GCAAAGTGAC GGTTTTAGCA
```

Fig. 1P (SEQ ID NO: 1)

```
          16330      16340      16350      16360      16370      16380
     ATCGGGTAGT GTACGAGACG TCGGCGGTGC AGAATGCGAC TCGCGGCGTA GCTCGCCGTC
     TAGCCCATCA CATGCTCTGC AGCCGCCACG TCTTACGCTG AGCGCCGCAT CGAGCGGCAG
          16390      16400      16410      16420      16430      16440
     GCTATGCGGC TCGTCGCCGT GTGGCGCGGC CTGGCCGGCT GTCTGCGTCC AGATCTGTTG
     CGATACGCCG AGCAGCGGCA CACCGCGCCG GACCGGCCGA CAGACGCAGG TCTAGACAAC
          16450      16460      16470      16480      16490      16500
     GCCTTTTGGT TCCTCTGGCT GCTGCTGCGT GTGTGCTTTG GTAGACGCGG TGGCAGTTTG
     CGGAAAACCA AGGAGACCGA CGACGACGCA CACACGAAAC CATCTGCGCC ACCGTCAAAC
          16510      16520      16530      16540      16550      16560
     CGGTCTGCGG TAAGTGAGGA TGTCGCCGAG CAAACGCACT TGCGGCGCGT GGGCGGCACG
     GCCAGACGCC ATTCACTCCT ACAGCGGCTC GTTTGCGTGA ACGCCGCGCA CCCGCCGTGC
          16570      16580      16590      16600      16610      16620
     CGTGTCATTG TAGGTTCGTT GCCAGATGGC AAGTGCTGTC AACAGCAGGC GTTGTGGGCG
     GCACAGTAAC ATCCAAGCAA CGGTCTACCG TTCACGACAG TTGTCGTCCG CAACACCCGC
          16630      16640      16650      16660      16670      16680
     GTCGGTGTAT TTTTGTGGGT TGCGGTGAGA GTCGGCACTC GGTGTTTTGT GAGTCATCTC
     CAGCCACATA AAAACACCCA ACGCCACTCT CAGCCGTGAG CCACAAAACA CTCAGTAGAG
          16690      16700      16710      16720      16730      16740
     AACTATCTGT GTTGCTTTGA GCAGCGTCCA GAACAGCGAC GCGACTTTGG GGATGGCCTC
     TTGATAGACA CAACGAAACT CGTCGCAGGT CTTGTCGCTG CGCTGAAACC CCTACCGGAG
          16750      16760      16770      16780      16790      16800
     GTGCTCACCT CCGCGGAGAG CGCCGCCGGA CCTGCTCGTC AGCAGCGAGC TACGCAGACG
     CACGAGTGGA GGCGCCTCTC GCGGCGGCCT GGACGAGCAG TCGTCGCTCG ATGCGTCTGC
          16810      16820      16830      16840      16850      16860
     GAATATCTGG AGGAGAGTTA CGTGTGTCAC AGGAGAGCGC GGGTCTCCGG CGGTAACGAC
     CTTATAGACC TCCTCTCAAT GCACACAGTG TCCTCTCGCG CCCAGAGGCC GCCATTGCTG
          16870      16880      16890      16900      16910      16920
     GGCGGTGTCG TCGACACGTG TGCGGCCTGT TGTGCTCTGC GGAAAAGTGC CGGTCTCGGA
     CCGCCACAGC AGCTGTGCAC ACGCCGGACA ACACGAGACG CCTTTTCACG GCCAGAGCCT
          16930      16940      16950      16960      16970      16980
     GACCGTGGAC GAAAAAGAGA ACGCAGCAGC TACCGCTGGC GGCGGCGGCG TTAATGCAGC
     CTGGCACCTG CTTTTTCTCT TGCGTCGTCG ATGGCGACCG CCGCCGCCGC AATTACGTCG
          16990      17000      17010      17020      17030      17040
     CGTTGATGTT CGACGTTGTG AGCACTCGGA AACAGCGGTG AGGCAGAAGG TCGATTCTCC
     GCAACTACAA GCTGCAACAC TCGTGAGCCT TTGTCGCCAC TCCGTCTTCC AGCTAAGAGG
          17050      17060      17070      17080      17090      17100
     AGGGAACGAC AGTCGATGCG TGGTAGCCGC AGCAGGTGAG GTTGGGGCGG ACAACGTGTT
     TCCCTTGCTG TCAGCTACGC ACCATCGGCG TCGTCCACTC CAACCCCGCC TGTTGCACAA
          17110      17120      17130      17140      17150      17160
     GCGGATTGTG GCGAGAACGT CGTCCTCCCC TTCTTCACCG CCCCACCCAC CCTCGGTTGG
     CGCCTAACAC CGCTCTTGCA GCAGGAGGGG AAGAAGTGGC GGGGTGGGTG GGAGCCAACC
          17170      17180      17190      17200      17210      17220
     TGTTTCTTTT TTCTTGTGTC CTGCAGATAG TTCCACGGAC AGCGACGGCA AGTCCATAAT
     ACAAAGAAAA AAGAACACAG GACGTCTATC AAGGTGCCTG TCGCTGCCGT TCAGGTATTA
          17230      17240      17250      17260      17270      17280
     CAGCGGTGTG CAAGTGGTGG AACACGACGA AGATATCATC GCGCCGCAGA GTTTGTGGTG
     GTCGCCACAC GTTCACCACC TTGTGCTGCT TCTATAGTAG CGCGGCGTCT CAAACACCAC
          17290      17300      17310      17320      17330      17340
     CACGGCGTTC AAGGAAGCCC TCTGGGATGT GGCTCTGTTG GAAGTGCCGC GTTGGGCGTG
     GTGCCGCAAG TTCCTTCGGG AGACCCTACA CCGAGACAAC CTTCACGGCG CAACCCGCAC
```

Fig. 1Q (SEQ ID NO: 1)

```
       17350      17360      17370      17380      17390      17400
   GCAGGGCTGG AAGAGGTGGC GCAACAGCGA GGCCGGGCGT CGATGGAGTG CTGGGTCTGC
   CGTCCCGACC TTCTCCACCG CGTTGTCGCT CCGGCCCGCA GCTACCTCAC GACCCAGACG 17410      17420      17430      17440      17450      17460
   GTCGGCTTCC AGCTTGTCTG ACTTGGCGGG CGAGGCCGTT GGAGAATTGG TGGGATCGGT
   CAGCCGAAGG TCGAACAGAC TGAACCGCCC GCTCCGGCAA CCTCTTAACC ACCCTAGCCA 17470      17480      17490      17500      17510      17520
   CGTCGCGTAC GTGATCCTTG AACGTCTGTG GTTGGCAGCC AGAGGTTGGG TGTGCGAAAC
   GCAGCGCATG CACTAGGAAC TTGCAGACAC CAACCGTCGG TCTCCAACCC ACACGCTTTG 17530      17540      17550      17560      17570      17580
   AGGTGTGGAA GCCCGAGGAGG CCATGTCGCG GCGGCGACAG CGCATGCTGT GGCGTATTGT
   TCCACACCTT CGGCTCCTCC GGTACAGCGC CGCCGCTGTC GCGTACGACA CCGCATAACA 17590      17600      17610      17620      17630      17640
   TCTCTCGTGG AGGCGACGGC GAATGCAGCA GACGGTGTTC GATGGAGATG GCGTGCGGGG
   AGAGAGCACC TCCGCTGCCG CTTACGTCGT CTGCCACAAG CTACCTCTAC CGCACGCCCC 17650      17660      17670      17680      17690      17700
   AAGAAAGCGC CGTGTTGTGA GCAGACGACG TAGGATGCGG GACGTCGGAG CACATGGGCC
   TTCTTTCGCG GCACAACACT CGTCTGCTGC ATCCTACGCC CTGCAGCCTC GTGTACCCGG 17710      17720      17730      17740      17750      17760
   ATGTGTGGTG GCAGATGGCG GTGTCCGCTG GTGTCTGCTG CGGCAGTGCA TAGACGAAGC
   TACACACCAC CGTCTACCGC CACAGGCGAC CACAGACGAC GCCGTCACGT ATCTGCTTCG 17770      17780      17790      17800      17810      17820
   AACATGTCGC TGTGAAGAGA TAGAGTGTGA GCATAGCTGC ATGCAGCGTT GCGTGTATAA
   TTGTACAGCG ACACTTCTCT ATCTCACACT CGTATCGACG TACGTCGCAA CGCACATATT 17830      17840      17850      17860      17870      17880
   GCGGGGGGGA TTAAGACGTT AATAAAGAAT AGCGGCGGTT CTGATAGGGC GACCGCTGAA
   CGCCCCCCCT AATTCTGCAA TTATTTCTTA TCGCCGCCAA GACTATCCCG CTGGCGACTT 17890      17900      17910      17920      17930      17940
   GTGAGCTGCG TGTGCGTGTG GTTTGTGGAG TCCCCGCCGC CCCCGGTCCC GTGTCCGCCG
   CACTCGACGC ACACGCACAC CAAACACCTC AGGGGCGGCG GGGGCCAGGG CACAGGCGGC 17950      17960      17970      17980      17990      18000
   GCAAAGCCCC CCGGNTCCGC ACACTCCTGG CCGCGCAACC CTCGTCGCTG CAAAAGCCCC
   CGTTTCGGGG GGCCNAGGCG TGTGAGGACC GGCGCGTTGG GAGCAGCGAC GTTTTCGGGG 18010      18020      18030      18040      18050      18060
   CCGTCCCCGC ACACCCCCGC GACCGCCGGT CCCGCGAGTC CCCGTCCCCG CCGCAAAAGG
   GGCAGGGGCG TGTGGGGCG CTGGCGGCCA GGGCGCTCAG GGGCAGGGGC GGCGTTTTCC 18070      18080      18090      18100      18110      18120
   CCCCCGTCCT CGCCGCAAAC ACCCCCGTCA CCCCCGTCCC TCAGNCCGGG TCCGCGAGTC
   GGGGGCAGGA GCGGCGTTTG TGGGGGCAGT GGGGGCAGGG AGTCNGGCCC AGGCGCTCAG 18130      18140      18150      18160      18170      18180
   CCCGTTCCCA GCGTAATCCC CGTACCCGCA ACGNCCCGGN CCCACCGTCG TCCCGCACAC
   GGGCAAGGGT CGCATTAGGG GCATGGGCGT TGCNGGGCCN GGGTGGCAGC AGGGCGTGTG 18190      18200      18210      18220      18230      18240
   CCCCCGTCCC CCAGCCCGGT GCCCAGCGTG CGAAAAAAGC TCCGTCCCTC ACACCCGCAG
   GGGGGCAGGG GGTCGGGCCA CGGGTCGCAC GCTTTTTTCG AGGCAGGGAG TGTGGGCGTC 18250      18260      18270      18280      18290      18300
   AAAGATCCCT CAGCGCGGTG AAACCCCGTC CCCAGCGCCG TGCCGCTGAC AAAGACCATG
   TTTCTAGGGA GTCGCGCCAC TTTGGGGCAG GGGTCGCGGC ACGGCGACTG TTTCTGGTAC 18310      18320      18330      18340      18350      18360
   GGACGACACG CACAGGCA..  .......... .......... .......... ..........
   CCTGCTGTGC GTGTCCGT..  .......... .......... .......... ..........
```

Fig. 1R (SEQ ID NO: 1)

Toledo UL130

```
         10         20         30         40         50         60
MLRLLLRHHF HCLLLCAVWA TPCLASPWST LTANQNPSPP WSKLTYSKPH DAATFYCPFL 70         80         90        100        110        120
YPSPPRSPLQ FSGFQQVSTG PECRNETLYL LYNREGQTLV ERSSTWVKKV IWYLSGRNQT 130        140        150        160        170        180
ILQRMPQTAS KPSDGNVQIS VEDAKIFGAH MVPKQTKLLR FVVNDGTRYQ MCVMKLESWA 190        200        210        220        230        240
HVFRDYSVSF QVRLTFTEAN NQTYTFCTHP NLII*..... .......... ..........
```

Toledo UL132

```
         10         20         30         40         50         60
MPALRGPLRA TFLALVAFGL LLQIDLSDAT NVTSSTKVPT STSNRNNVDN ATSSGPTTGI 70         80         90        100        110        120
NMTTTHESSV HNVRNNEIMK VLAILFYIVT GTSIFSFIAV LIAVVYSSCC KHPGRFRFAD 130        140        150        160        170        180
EEAVNLLDDT DDSGGSSPFG SGSRRGSQIP PDFVPRALIS GWKLGTGTRR RRRPRPASA*

190        200        210        220        230        240
NMILRTSSIS ERMATWTRRS *IPIMGEARL *PSNLTSRTM RRTPSGTTFR CTMN*PPRKW 250        260        270        280        290        300
KNLRTAPAGR FPN**KLPCN PSRSEIPSTT R......... .......... ..........
```

Toledo UL133

```
         10         20         30         40         50         60
MGCDVHDPSW QCQWGVPTII VAWITCAALG IWCLAGSSAD VSSGPGIAAV VGCSVFMIFL 70         80         90        100        110        120
CAYLIRYREF FKDSVIDLLT CRWVRYCSCS CKCSCKCISG PCSRCCSACY KETMIYDMVQ 130        140        150        160        170        180
YGHRRRPGHG DDPDRVICEI VESPPVSAPT VSVPPPSEES HQPVIPPQPP APTSEPKPKK 190        200        210        220        230        240
GRAKDKPKGR PKDKPPCEPT VSSQPPSQPT AMPGGPPDAP PPAMPQMPPG VAEAVQAAVQ 250        260        270        280        290        300
AAVAAALQQQ QQHQTGT*.. .......... .......... .......... ..........
```

Fig. 2A

Toledo UL134

```
           10         20         30         40         50         60
    MARTREASPV PPRSPMPSHI HTMIFSPAWN LKLRVGKGRC TDIYALDFWK RHFLARNVFI 70         80         90        100        110        120
    VQTLRKEMCA KSENSLSHRG RVTFRSDAAA VVVEPRPRPP ARQLVPPRPR RVASAAWRGE 130        140        150        160        170        180
    ARRADRRALP SAATVVVNSP SVRTEVCLSV YPSVYLSPYL SSVWVPMSVL AAAVG*....
```

Toledo UL135

```
           10         20         30         40         50         60
    MSVHRPFPTR SLRFQAGEKI MVWIWLGIGL LGGTGLASLV LAISLFTQRR GRKRSDETSS 70         80         90        100        110        120
    RGRLPGAASD KRGACACCYR NPKEDVVEPL DLELGLMRVD THPPTPQVPR CTSLYIGEDG 130        140        150        160        170        180
    LPIDKPEFPP ARFEIPDVST PGTPTSIGRS PSHCSSSSSL SSSTSVDTVL YQPPPSWKPP 190        200        210        220        230        240
    PPPGRKKRPP TPPVRAPTTR LSSHRPPTPI PAPRKNLSTP PTKKTPPPTK PKPVGWTPPV 250        260        270        280        290        300
    TPRPFPKTPT PQKPPRNPRL PRTVGLENLS KVGLSCPCPR PRTPTEPTTL PIVSVSELAP 310        320        330        340        350        360
    PPRWSDIEEL LEQAVQSVMK DAESMQMT*. .......... .......... ..........
```

Toledo UL136

```
           10         20         30         40         50         60
    MSVKGVEMPE MTWDLDVRNK WRRRKALSRI HRFWECRLRV WWLSDAGVRE TDPPRPRRRP 70         80         90        100        110        120
    TWMTAVFHVI CAVLLTLMIM AIGALIAYLR YYHQDSWRDM LHDLFCGCHY PEKCRRHHER 130        140        150        160        170        180
    QRRRRQAMDV PDPELGDPAR RPLNGAMYYG SGCRFDTVEM VDETRPAPPA LSSPETGDDS 190        200        210        220        230        240
    NDDAVAGGGA GGVTSPATRT TSPNALLPEW MDAVHVAVQA AVQATVQVSG PRENAVSPAT 250        260        270        280        290        300
    *......... .......... .......... .......... .......... ..........
```

Fig. 2B

Toledo UL137

```
         10         20         30         40         50         60
MATISTSITP MMGNPTFSGR SSMVTVLCPD LRPSLSLLYS TRAGTAPSTL LRSGRYGVLP 70         80         90        100        110        120
RATYLHGRLN GGLDRHMHRI HPFWQQCVRR RRTSRG*... .......... ..........
```

Toledo UL138

```
         10         20         30         40         50         60
MDDLPLNVGL PIIGVMLVLI VAILCYLAYH WHDTFKLVRM FLSYRWLIRC CELYGEYERR 70         80         90        100        110        120
FADLSSLGLG AVRRESDRRY RFSERPDEIL VRWEEVSSQC SYASSRITDR RVGSSSSSSV 130        140        150        160        170        180
HVASQRNSVP PPDMAVTAPL TDVDLLKPVT GSATQFTTVA MVHYHQEYT* ..........
```

Toledo UL139

```
         10         20         30         40         50         60
MLWILVLFAL AASASETTTG TSSNSSQSTS ATANTTVSTC INASNGSSWT VPQLALLAAS 70         80         90        100        110        120
GWTLSGLLLL FTCCFCCFWL VRKICSCCGN SSESESKTTH AYTNAAFTSS DATLPMGTTG 130        140        150        160        170        180
SYTPPQDGSF PPPPR*.... .......... .......... .......... ..........
```

Toledo UL140

```
         10         20         30         40         50         60
MTPAQTNATT TVHPHDAKNG SGGSALPTLV VFGFIVTLLF FLFMLYFWNN DVFRKLLRAL 70         80         90        100        110        120
GSSAVATAST RGKTRSSTVV HHVVPRATTR VVLTACHRTF FYHPRPMAVL TTRH*.....
```

Fig. 2C

Toledo UL141

```
         10         20         30         40         50         60
 MRQVAYRRRR ESSCAVLVHH VGRDGDGEGE AAKKTCKKTG RSVAGIPGEK LRRTVVTTTP 70         80         90        100        110        120
 ARRLSGRHTE QEQAGMRLCE KGKKRIIMCR RESLRTLPWL FWVLLSCPRL LEYSSSSFPF 130        140        150        160        170        180
 ATADIAEKMW AENYETTSPA PVLVAEGEQV TIPCTVMTHS WPMVSIRARF CRSHDGSDEL 190        200        210        220        230        240
 ILDAVKGHRL MNGLQYRLPY ATWNFSQLHL GQIFSLTFNV SMDTAGMYEC VLRNYSHGLI 250        260        270        280        290        300
 MQRFVILTQL ETLSRPDEPC CTPALGRYSL GDQIWSPTPW RLRNHDCGTY RGFQRNYFYI 310        320        330        340        350        360
 GRADAEDCWK PACPDEEPDR CWTVIQRYRL PGDCYRSQPH PPKFLPVTPA PPADIDTGMS 370        380        390        400        410        420
 PWATRGIAAF LGFWSIFTVC FLCYLCYLQC CGRWCPTPGR GRRGEGYRR  LPTYDSYPGV 430        440        450        460        470        480
 RKMKR*.... .......... .......... .......... .......... ..........
```

Toledo UL142

```
         10         20         30         40         50         60
 MRIEWVWWLF GYFVSSVGSE RSLSYRYHLE SNSSTNVVCN GNISVFVNGT LGVRYNITVG 70         80         90        100        110        120
 ISSSLLIGHL TIQVLESWFT PWVQNKSYNK QPLGDTETLY NIDSENIHRV SQYFHTRWIK 130        140        150        160        170        180
 SLQENHTCDL TNSTPTYTYQ VNVNNTNYLT LTSSGWQDRL NYTVINSTHF NLTESNITSI 190        200        210        220        230        240
 QKYLNTTCIE RLRNYTLESV YTTTVPQNIT TSQHATTTMH TIPPNTITIQ NTTQSHTVQT 250        260        270        280        290        300
 PSFNDTHNVT KHTLNISYVL SQKTNNTTSP WIYAIPMGAT ATIGAGLYIG KHFTPVKFVY 310        320        330        340        350        360
 EVWRGQ*... .......... .......... .......... .......... ..........
```

Fig. 2D

Toledo_UL143

```
         10         20         30         40         50         60
MARSVKTIRI QHIYSPRSSN TLQHMSKKQE SIATITFGRI TCCHPLASIN LMFNGSCTVT 70         80         90        100        110        120
VKISMGINGS TNVHQLVIVL HLGNRCQPWR QV*....... .......... ..........
```

Toledo_UL144

```
         10         20         30         40         50         60
MKPLIMLICF AVILLQLGVT KVCQHNEVQL GNECCPPCGS GQRVTKVCTD YTSVTCTPCP 70         80         90        100        110        120
NGTYVSGLYN CTDCTQCNVT QVMIRNCTST NNTVCAPKNH TYFSTPGVQH HKQRQQNHTA 130        140        150        160        170        180
HITVKQGKSG RHTLAWLSLF IFLVGIILLI LYLIAAYRSE RCQQCCSIGK IFYRTL*...
```

Toledo_UL145

```
         10         20         30         40         50         60
MCTDPRRTAG WERLTHHASY HANYGAYAVL MATSQRKSLV LHRYSAVTAV ALQLMPVEIV 70         80         90        100        110        120
RKLDQSDWVR GAWIVSETFP TSDPKGVWSD DDSSMGGSDD *......... ..........
```

Toledo_UL146

```
         10         20         30         40         50         60
MRLIFGALII FLAYVYHYEV NGTELRCRCL HRKWPPNKII LGNYWLHRDP RGPGCDKNEH 70         80         90        100        110        120
LLYPDGRKPP GPGVCLSPDH LFSKWLDKHN DNRWYNVNIT KSPGPRRINI TLIGVRG*..
```

Fig. 2E

Toledo UL147

```
           10         20         30         40         50         60
    MVLTWLHHPV SNSHINLLSV RHLSLIAYML LTICPLAVHV LELEDYDRRC RCNNQILLNT 70         80         90        100        110        120
    LPVGTELLKP IAASESCNRQ EVLAILKDKG TKCLNPNAQA VRRHINRLFF RLILDEEQRI 130        140        150        160        170        180
    YDVVSTNIEF GAWPVPTAYK AFLWKYAKRL NYHHFRLRW*
```

Toledo UL148

```
           10         20         30         40         50         60
    MLRLLFTLVL LALHGQSVGA SRDYVHVRLL SYRGDPLVFK HTFSGVRRPF TELGWAACRD 70         80         90        100        110        120
    WDSMHCTPFW STDLEQMTDS VRRYSTVSPG KEVTLQLHGN QTVQPSFLSF TCRLQLEPVV 130        140        150        160        170        180
    ENVGLYVAYV VNDGERPQQF FTPQVDVVRF ALYLETLSRI VEPLESGRLA VEFDTPDLAL 190        200        210        220        230        240
    APDLVSSLFV AGHGETDFYM NWTLRRSQTH YLEEMALQVE ILKPRGVRHR AIIHHPKLQP 250        260        270        280        290        300
    GVGLWIDFCV YRYNARLTRG YVRYTLSPKA RLPAKAEGWL VSLDRFIVQY LNTLLITMMA 310        320        330        340        350        360
    AIWARVLITY LVSRRR*
```

Toledo UL149

```
           10         20         30         40         50         60
    MVDQCCYRHL HRSLSGGPDV LYAAAGTQRE QQRLDKSLAA TAPSAVAGPP ADRDVVDHRT 70         80         90        100        110        120
    ETHAYETPRY ATRCLTRYTT PVRSAVRRTT CGKRVASQSP PRSCLVAPQS SPAHPPRHPE 130        140        150        160        170        180
    GG*
```

Fig. 2F

Toledo UL150

```
         10         20         30         40         50         60
MQLCSHSISS QRHVASSMHC RSRHQRTPPS ATTHGPCAPT SRILRRLLTT RRFLPRTPSP 70         80         90        100        110        120
SNTVCCIRRR LHERTIRHSM RCRRRDMASS ASTPVSHTQP LAANHRRSRI TYATTDPTNS 130        140        150        160        170        180
PTASPAKSDK LEADADPALH RRPASLLRHL FQPCHAQRGT SNRATSQRAS LNAVHHKLCG 190        200        210        220        230        240
AMISSSCSTT CTPLIMDLPS LSVELSAGHK KKETPTEGGW GGEEGEDDVL ATIRNTLSAP 250        260        270        280        290        300
TSPAAATTHR LSFPGESTFC LTAVSECSQR RTSTAALTPP PPAVAAAFSF SSTVSETGTF 310        320        330        340        350        360
PQSTTGRTRV DDTAVVTAGD PRSPVTHVTL LQIFRLRSSL LTSRSGGALR GGEHEAIPKV 370        380        390        400        410        420
ASLFWTLLKA TQIVEMTHKT PSADSHRNPQ KYTDRPQRLL LTALAIWQRT YNDTRAAHAP 430        440        450        460        470        480
QVRLLGDILT YRRPQTATAS TKAHTQQQPE EPKGQQIWTQ TAGQAAPHGD EPHSDGELRR 490        500        510        520        530        540
ESHSAPPTSR TLPDTILAVK RRSVAQRSHV RLDAKPGLNE RDGFRQRLLL PLSGYFRANE 550        560        570        580        590        600
LRNQQFMGYG TKNGLKNTWL TRPLGVAGGV RETIGERQDR NVADSATQRV FHTLYAALQT 610        620        630        640        650        660
VRVWYTALGT AWRTSGSRTR ESLFDGPRRR DRQAARLRRL EL*....... ..........
```

Fig. 2G

Toledo UL151

```
            10          20          30          40          50          60
    MVFVSGTALG  TGFHRAEGSF  CGCEGRSFFR  TLGTGLGDGG  CAGRRWXRXV  AGTGITLGTG 70          80          90         100         110         120
    TRGPGLRDGG  DGGVCGEDGG  LLRRGRGLAG  PAVAGVCGDG  GLLQRRGLRG  QECAXPGGFA 130         140         150         160         170         180
    GGHGTGGGGD  STNHTHTQLT  SAVALSEPPL  FFINVLIPPA  YTRNAACSYA  HTLSLHSDML 190         200         210         220         230         240
    LRLCTAAADT  SGHRHLPPHM  AHVLRRPASY  VVCSQHGAFF  PARHLHRTPS  AAFAVASTRE 250         260         270         280         290         300
    QYATACAVAA  ATWPPRLPHL  FRTPNLWLPT  TDVQGSRTRR  PIPPILQRPR  PPSQTSWKPT 310         320         330         340         350         360
    QTQHSIDARP  RCCATSSSPA  TPNAALPTEP  HPRGLP*...  ..........  ..........
```

Fig. 2H

Clinical Strains of CMV
Contain Sequences
Homologous
to the Toledo $U_L/b'$ Region

Previous Towne Vaccine Strains Hybridize to the Toledo U$_L$/b' Region

Fig. 8

Cotransfection of Cosmids Regenerates Infectious CMV
Towne•AV
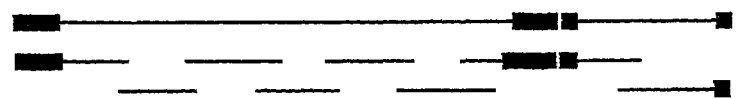
Toledo
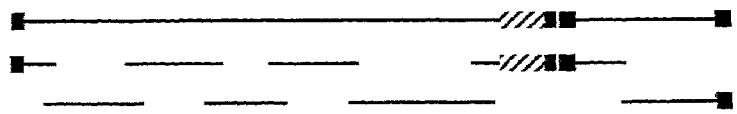
Figure 9

ATTENUATION OF CYTOMEGALOVIRUS VIRULENCE

TECHNICAL FIELD

The present invention is related generally to methods and compositions for treating or preventing cytomegalovirus (CMV) infections, such as congenital CMV disease, CMV retinitis, CMV mononucleosis, and the like, and methods of attenuating pathogenic cytomegalovirus isolates and strains, genetically engineered cytomegaloviruses and combinations thereof, methods for altering the phenotype of CMV viruses, attentuated viral vaccine compositions, and uses thereof. More particularly, the present invention is related to methods and compositions for prophylaxis and therapy of human cytomegalovirus infection, including the use of methods that functionally inactivate a subset of cytomegalovirus genes present in pathogenic isolates of human cytomegalovirus.

BACKGROUND

Cytomegalovirus (CMV) is a widespread herpesvirus in the human population, with between 0.2 and 2.2% of the infant population becoming infected in utero and another 8–60% becoming infected during the first six months of life (Reynolds et al. (1973) *New Engl. J. Med.* 289: 1). Although CMV infections are most commonly subclinical, CMV-induced sensorineural hearing loss and fatal cytomegalovirus infections ("cytomegalic inclusion disease") are important public health problems. Moreover, CMV is one of the more common opportunistic infections associated with Acquired Immune Deficiency Syndrome ("AIDS") and frequently produces disease, with recurrent infection occurring in HIV-positive individuals, typically taking the form of retinitis or ulcerative lesions in the colon and esophagus, and occasionally producing extensive necrotization of the bowel with a grave prognosis (Rene et al. (1988) *Div. Dis. Sci.* 33: 741; Meiselman et al. (1985) *Gastroenterology:* 88: 171). Cytomegalovirus (CMV) infection is the major infectious cause of mental retardation and congenital deafness. CMV is also responsible for a great deal of disease among the immunosuppressed, producing general and often severe systemic effects in patients with AIDS, in organ transplant recipients who have been iatrogenically immunosuppressed, and in bone marrow transplant patients.

It is clear that cytomegalovirus infections are a significant human health problem. Therefore, it is desirable to develop prophylactic and therapeutic methods and compositions to prevent cytomegalovirus infection and/or inhibit recurrent infectious outbreaks from persistent latent infections, particularly for treating CMV retinitis, CMV mononucleosis, and related CMV pathology in human patients.

One approach that has been used to treat herpesvirus infections is to inhibit CMV viral DNA replication. For example, viral DNA replication can frequently be inhibited by agents that inhibit virally-encoded DNA polymerase. The most notable examples of such inhibitors of viral DNA polymerase are acyclovir, ganciclovir, citrusine-I, and the acyclic guanosine phosphonate (R,S)-HPMPC (Terry et al. (1988) *Antiviral Res.* 10: 235; Yamamoto et al. (1989) *Antiviral Res.* 12: 21). However, these compounds are not completely selective for viral thymidylate synthetases or DNA polymerases and therefore can disadvantageously cause inhibition of host DNA replication at high doses. Moreover, the development of mutant viruses which are resistant to the inhibitory effects of these compounds have been reported, and appear to result from mutations in the viral DNA polymerase (Coen et al. (1982) *J. Virol.* 41: 909; Coen et al. (1980) *Proc. Natl. Acad. Sci.* (*U.S.A.*) 77: 2265; Larder et al. (1987) *EMBO J.* 6: 169). Thus, while CMV infections, such as CMV retinitis, can be initially treated with foscarnet and ganciclovir, after a period of time CMV replication and progression of the pathological viral infection recurs.

Passive immunization with antibodies (e.g., immune globulin) has been tested in combination with ganciclovir for therapeutic efficacy in humans. Such antibody preparations are obtained from the serum of donors, who possess a high antibody titre to the virus as a result of an earlier infection. One disadvantage of such conventional antibody preparations is the limited number of suitable donors and the poor reproducibility or quality of the various preparations, including potential contamination with pathogens and pathogenic viruses. Unfortunately, the use of intravenous immune globulin in combination with ganciclovir apparently does not produce significantly improved efficacy as compared to ganciclovir treatment alone (Jacobson et al. (1990) *Antimicrob. Agents and Chemother.* 34: 176).

The safety and pharmacokinetic profiles of anti-cytomegalovirus monoclonal antibodies are discussed in Aulitzky et al. (1991) *J. Infect. Dis.* 163: 1344 and Drobyski et al. (1991) *Transplantation* 51: 1190. However, none of the reported human anti-CMV monoclonal antibodies have been shown to possess significant therapeutic efficacy in treating CMV infections (e.g., retinitis) in humans.

Attempts to use recombinantly produced hCMV glycoproteins as a subunit vaccine to provide protective immunity against hCMV infection and pathogenesis have not proven to be effective, but remain candidates for additional evaluation.

Thus, there exists a need in the art for effective methods and compositions for inhibiting human cytomegalovirus replication, attenuating CMV virulence in vivo, neutralizing CMV virions, and for preventing and treating human cytomegalovirus infections, and especially CMV infections in preborns, newborns, and immunosuppressed patients such as AIDS patients. For example but not limitation, a suitable attenuated human CMV vaccine which elicits satisfactory immunoprotection against CMV infection is needed in the art. The present invention fulfills these and other needs.

SUMMARY OF THE INVENTION

A basis of the present invention is the surprising and unexpected finding that: (1) clinical isolates of pathogenic CMV variants contain a genomic region ("virulence region") which typically is not present in CMV strains which have undergone extensive laboratory passaging of the virus in cell culture (hereafter termed "highly passaged strain variants") and (2) functional disruption (e.g., deletion or insertional inactivation and the like) of genes in this genomic region produces a substantial attenuation of CMV virulence and/or pathogenicity in vivo. Furthermore, the virulence region of a clinical isolate of CMV is frequently deleted, rearranged, or substantially changed over the course of passaging the virus in cell culture.

In one aspect of the invention, the virulence region is obtained from an early passage Toledo strain and is conveniently termed the "Toledo genomic region" herein, although equivalent (e.g., homologous) regions or subsequences thereof are present in other clinical isolates of CMV besides the Toledo strain of CMV; the term "Toledo genomic region" encompasses these homologous regions in other clinical CMV isolates, many early passage CMV strains, and non-isolated pathogenic CMV variants.

The Toledo genomic region which is present in pathogenic CMV isolates and which is typically substantially absent in highly passaged CMV strains (e.g., AD169, high-passage Towne) has been sequenced and several open-reading frames have been identified (PCT Publication WO96/30387, U.S. Ser. No. 08/414,926, U.S. Ser. No. 08/644,543 filed 10 May 1996, each incorporated herein in their entirety by reference). Functional disruption of these open reading frames, either singly or in combination, has been unexpectedly found to substantially reduce virulence of the resultant CMV mutant(s) in vivo. Thus, in part, the invention provides methods and compositions for suppressing or inactivating expression of genes of the Toledo genomic region and its homolog regions in other CMV variants, and thereby reducing virulence and pathogenicity of clinically important CMV variants to generate a "Toledo region-attenuated CMV variant"; such Toledo region-attenuated CMV variants have altered phenotypes which generally make them candidates for use in live attenuated virus vaccines for prophylaxis and/or treatment of CMV disease. The invention is, in part, further based on the heretofore unrecognized finding that pathogenic clinical isolates of CMV have a distinct genome as compared to the commonly used laboratory-passaged strains of human CMV (e.g., AD169, highly-passaged Towne), and that the genomic region which is present in the clinical isolates and which is substantially absent in laboratory-passaged strains confers enhanced virulence in vivo. Most common approaches to development of CMV therapies and vaccines have heretofore relied on laboratory-passaged strains which typically lack all or part of the Toledo genomic region and the genes encoded therein which have been unexpectedly found to confer enhanced in vivo virulence and are believed to contribute to clinical pathology and CMV-related disease.

The invention provides a method for attenuating virulence of CMV comprising functionally inactivating at least one open reading frame in a virulence region of a CMV genome having substantial identity to at least 300 bp, typically at least 500 bp, of a 15 kb sequence present in the genome of the AD169 strain of CMV and/or absent from the genome of highly-passaged Towne (i.e., more than 50–100 passages). In an aspect, the method functionally inactivates at least one open reading frame present in a genomic region of a CMV genome having substantial identity to at least 300 bp of a 13 kb sequence present in the genome of the Toledo strain of CMV and absent from the genome of the Towne strain of CMV. In an embodiment, the method functionally inactivates at least one open reading frame present in a genomic region of a CMV genome having substantial identity to at least 500 bp of the sequence shown in FIGS. 1A through 1R (SEQ ID NO:1). In an embodiment, the method functionally inactivates at least the open reading frame corresponding to UL 148 as identified herein. In a variation, the method functionally inactivates open reading frames in the region spanning UL138 to UL 148. In an embodiment, the method functionally inactivates UL138, UL139, UL140, UL141, UL 142, UL 143, UL144, UL145, UL146, UL147, and/or UL148. In a variation, UL148 is inactivated singly or in combination with other open reading frames of the Toledo genomic region. In a specific embodiment, UL148 is inactivated in combination with UL141 and/or UL144. Typically, such Toledo region-attenuated CMV variants comprise at least 500 bp of the Toledo genomic region or a homolog region having at least 80 percent sequence identity; frequently they comprise at least 1.0 kbp of the Toledo genomic region or hmolog virulence region; often they contain at least 5.0 kbp to 8.0 kbp of the Todedo genomic region or homolog virulence region, and can comprise up to a complete Toledo genomic region or homolog virulence region. It is possible for a synthetic virulence region to be comprised of portions of two or more virulence regions (e.g., such as a chimeric virulence region comprising part of the Toledo genomic region from a first clinical isolate with a complementing portion of the Toledo genomic region of a second clinical isolate).

In an aspect, the invention provides a method for attenuating a CMV strain or isolate containing an encoding polynucleotide sequence encoding a polypeptide which is at least 80 percent sequence identical to a polypeptide encoded by UL138, UL139, UL140, UL141, UL142, UL143, UL144, UL145, UL146, UL147, and/or UL148 of the Toledo genomic region; the method comprising functionally inactivating (e.g., deleting or introducing a nonsense or missense mutation) said encoding polynucleotide sequence to produce a Toledo region-attenuated CMV variant. In a variation, all open reading frames (ORFs) in the CMV isolate that are at least 80% sequence identical to the corresponding sequence of the Toledo genomic region are functionally inactivated. In a variation, all open reading frames (ORFs) in the CMV isolate that are at least 80% sequence identical to UL138, UL139, UL140, UL141, UL142, UL143, UL144, UL145, UL146, UL147, and/or UL148 of the Toledo genomic region are functionally inactivated. In an alternate variation, only one or a subset of the open reading frames (ORFs) in the CMV isolate that are at least 80% sequence identical to the corresponding sequence(s) of the Toledo genomic region are functionally inactivated. Such Toledo region-attenuated CMV variants comprise at least 500 bp of a Toledo genomic region and can comprise up to a complete Toledo genomic region (including a chimeric Toledo genomic region composed from distinct clinical isolates or strains).

In an aspect, the invention provides a recombinant CMV virus, comprising a genome having at least 500 bp of a virulence region wherein at least one ORF has been functionally inactivated by a genetic alteration which is predetermined and/or which does not occur in known isolates or strains of CMV regardless of passage history.

In an aspect, the method of attenuating virulence comprises functional inactivation of open reading frames by predetermined structural mutation (e.g., deletion, insertion, missense or nonsense mutation, and the like) of at least one open reading frame, or a predetermined mutation of a transcriptional control sequence that controls transcription of the open reading frame, or predetermined mutation of a splicing signal sequence or the like necessary for efficient expression of the encoded gene product of the open reading frame. In an embodiment, a selectable marker gene is introduced into an open reading frame, often in the portion of the open reading frame believed to encode the amino-terminal two-thirds of the gene product, to structurally disrupt the open reading frame and result in the inactivation of the open reading frame's capacity to encode its functional gene product. In a variation, open reading frame UL148 is structurally disrupted by mutation; in one embodiment the structural disruption results from insertion of a selectable and/or screenable marker gene (e.g., gpt/lacZ). In an embodiment, a selectable marker gene is used to replace all or part of at least one open reading frame, such as by replacement of a deleted region of the Toledo genomic region with a selectable marker gene. In a variation, a region spanning open reading frame UL138 to UL148 is structurally disrupted by mutation; in one embodiment the structural disruption results from deletion of the UL138–UL148 region and replacement with a selectable and/or screenable marker gene (e.g., gpt/lacZ).

In an aspect, the functional inactivation of a Toledo genomic region gene is provided by transcriptional and/or translational suppression with an antisense polynucleotide having a sequence of at least 15 nucleotides, typically at least 25 nucleotides, that are substantially complementary to a Toledo genomic region, most usually the antisense polynucleotide is substantially complementary to an open reading frame sequence of a Toledo genomic region open reading frame. In an embodiment, the antisense polynucleotide is substantially complementary to at least 25 nucleotides of UL148. In an embodiment, the antisense polynucleotide is complementary to UL148 and further comprises additional 5' and/or 3' nucleotide(s) which are not substantially complementary to UL148. In variations, the antisense polynucleotides comprise non-natural chemical modifications, and can include, for instance, methylphosphonates, phosphorothioates, phosphoramidites, phosphorodithioates, phosphorotriesters, and boranophosphates. In a variation the antisense molecules can comprise non-phosphodiester polynucleotide analogs wherein the phosphodiester backbone is replaced by a structural mimic linkage include: alkanes, ethers, thioethers, amines, ketones, formacetals, thioformacetals, amides, carbamates, ureas, hydroxylamines, sulfamates, sulfamides, sulfones, and glycinylamides. In a variation, the invention provides peptide nucleic acids (PNAs) having a nucleobase sequence which is substantially complementary to a Toledo genomic region sequence, such as an open reading frame (e.g., UL148, UL141, UL142, etc.).

The invention also provides attenuated live virus CMV vaccines wherein at least one open reading frame of a Toledo genomic region is structurally disrupted. Typically, the UL148 open reading frame is structurally disrupted, either singly or in combination with other Toledo region open reading frames (e.g., UL141, UL144, and the like). Often the disruption of the open reading frame is an insertion, deletion, or replacement mutation which confers the property of reduced virulence as determined by a suitable in vivo virulence assay (e.g., see Experimental Examples). Toledo genomic region mutants which exhibit at least one log reduction, preferably two logs or more reduction, in virulence as determined by in vivo virulence assay, or other equivalent virulence measure, are attenuated CMV vaccines. Such attenuated CMV vaccines are used to immunize individuals to confer protective immunity, typically antibody-mediated and/or cell-mediated immunity, to prevent or reduce the severity of subsequent CMV infection following a suitable immunization period.

In an aspect, the invention also provides attenuated live virus CMV vaccines wherein at least one open reading frame of a Toledo genomic region is replaced by a segment of Towne genome which is not present in AS169. The Towne genome comprises a region no present in AD169; the region contains open reading frame designated UL147, UL152, UL153, and UL154 and generally is spanned by nucleotides 178221 to 180029 of the Towne genome according to the AD169 (EMBL accession number X17403) numbering convention. An attenuated virus of the invention can, in one embodiment, comprise a Toledo genome wherein the Toledo genome region spanning open reading frames UL133 to UL151 are replaced with a Towne genome region spanning UL147, UL152, UL153, and UL154; this engineered CMV virus variant is an attenuated Toledo virus which comprises desirable features of Towne while reducing undesirable virulence of the Toledo genome region. The invention provides other variations of this basic method, whereby a segment of the Toledo genome region comprising at least one open reading frame is deleted or otherwise structurally disrupted in a CMV variant having a Toledo genome region or its homolog, and a segment of a Towne genome region comprising at least one open reading frame in inserted in the CMV variant. In an embodiment, the engineered CMV variant comprises: (1) Toledo DNA (DNA substantially identical to a Toledo strain, preferably identical to it) from about nucleotides 1 to about 168,000 corresponding to (i.e., according to) the AD169 nucleotide (EMBL accession number X17403) numbering convention, operably linked to (2) Towne DNA (DNA substantially identical to a Towne strain, preferably identical to it) from about nucleotides 143,824 to 189,466 according to the AD169 nucleotide (EMBL accession number X17403) numbering convention, operably linked to (3) Toledo DNA (DNA substantially identical to a Toledo strain, preferably identical to it) from about nucleotides 189,466 to about 209,514 corresponding to (i.e., according to) the AD169 nucleotide (EMBL accession number X17403) numbering convention, operably linked to (4) Towne DNA (DNA substantially identical to a Towne strain, preferably identical to it) from about nucleotides 200,080 to 229,354 according to the AD169 nucleotide (EMBL accession number X17403) numbering convention. The invention also provides vaccine compositions and formulations of such attenuated CMV viruses, which can include adjuvants, delivery vehicles, liposomal formulations, and the like. The invention also provides the use of such attenuated CMV variants for prevention of CMV disease and infection; in one aspect this use includes administration of such vaccine to human subjects.

In a variation, the functional inactivation of a Toledo genomic region gene is provided by suppressing function of a gene product encoded by a Toledo region open reading frame by contacting or administering an antibody which is specifically reactive with said gene product. In an embodiment, the Toledo genomic region gene is UL148, UL141, and/or UL144, typically at least UL148, although other Toledo open reading frames can be used. The antibody binds to a gene product encoded by a Toledo region open reading frame with an affinity of at least about $1 \times 10^7$ $M^{-1}$, typically at least about $1 \times 10^8$ $M^{-1}$, frequently at least $1 \times 10^9$ $M^{-1}$ to $1 \times 10^{10}$ $M^{-1}$ or more. In some aspects, the antibody is substantially monospecific. In an embodiment, the antibody is a human antibody raised by immunizing an individual with an immunogenic dose of a gene product of a Toledo region open reading frame. In an embodiment, the human antibody is a monoclonal antibody, or collection of human monoclonal antibodies which bind to the Toledo region gene product(s). In an embodiment, the antibody is a humanized antibody comprising complementarity-determining regions substantially obtained from a non-human species immunoglobulin reactive with the Toledo region gene product, and further comprising substantially human sequence framework and constant regions. The invention also comprises pharmaceutical formulations of such antibodies and the use of such antibodies to treat or prevent CMV diseases, such as by passive immunization or the like.

In an aspect, the invention provides a composite CMV variant comprising a highly-passaged Towne genome and at least one open reading frame of a Toledo genome region, typically present in or adjacent to the $U_L/b'$ region of the composite CMV. In an aspect, the composite CMV is a highly-passaged Towne genome further comprising a Toledo UL148, UL141, and/or UL144. In an embodiment, the composite CMV is a highly-passaged Towne genome with a complete Toledo genome region; in a variation said Toledo genome region has at least one open reading frame functionally inactivated to further attenuate the virulence of the composite CMV. In a variation, a low passage Towne genome (i.e, less than 40 passages in culture) is used in place of a highly-passaged Towne genome. In an alternate variation, a virulence region from a low-passage Towne genome is emplaced in a Toledo genome so as to thereby replace at least 1 kpb of the virulence region of the Toledo genome with at least 500 bp, typically approximately the same length, of a corresponding region (e.g., substantial sequence identity) of low-passage Towne.

In an aspect, the invention provides a chimeric CMV virus, comprising a genome having a plurality of polynucleotide sequences, linked in conventional phosphodiester linkage, wherein at least two of said polynucleotide sequences are derived from different clinical isolates or strains of CMV. Said chimeric CMV virus can comprise a genome having a plurality of polynucleotide sequences, linked in conventional phosphodiester linkage, wherein a first CMV genome sequence of at least 500 bp and less than a complete CMV genome length (e.g., less than 250 kbp) is at least 98 percent sequence identical to a first CMV isolate or strain, and at least one additional CMV sequence of at least 500 bp and less than a complete CMV genome length (e.g., less than 250 kbp) is at least 98 percent sequence identical to a second CMV isolate or strain which has a genome having a polynucleotide sequence of at least 500 bp which is less than 60 percent sequence identical to any portion of the genome of said first CMV isolate or strain and/or which is absent or substantially absent in the genome of said first CMV isolate or strain. Said chimeric CMV virus comprises a genome having sufficient genetic information to replicate as a virus, typically as an infectious virus, in suitable host cells or a suitable host organism or replication system (e.g., SCID/hu thy/liv mice, human lung fibroblasts, and other systems known in the art). Generally, said chimeric CMV virus has a genome that comprises genetic information which is substantially sequence identical, generally at least 80 percent sequence identical, usually at least 95 percent sequence identical or more, to a high-passage Towne genome; said chimeric CMV virus genome typically further comprises genetic information which is substantially sequence identical, generally at least 80 percent sequence identical, usually at least 95 percent sequence identical or more, to at least 1 kbp of a virulence region of a clinical isolate of CMV or a low-passage strain of CMV other than low-passage Towne; in an embodiment, a complete virulence region (e.g., Toledo genome region) of a clinical isolate or low-passage CMV strain is present.

In an aspect, the invention provides a chimeric CMV virus, comprising a chimeric genome comprising a polynucleotide having a first CMV sequence of at least 500 bp having at least 97 percent sequence identity with a genome of a first CMV isolate or CMV strain and a second CMV sequence of at least 500 bp having at least 97 percent sequence identity with a genome of a second CMV isolate or CMV strain, and wherein said chimeric genome comprises genetic information having substantial identity (e.g., at least 80 percent sequence identity, preferably at least 95 percent sequence identity) spanning at least about the complete low-passage Towne genome. Typically, the chimeric genome comprises at least 500 bp containing at least one ORF having at least 95 to preferably 100 percent sequence identity to a virulence region of low-passage Towne genome other than low-passage Towne.

In an aspect, the invention provides a chimeric CMV virus, comprising a chimeric genome comprising a polynucleotide having a first CMV sequence of at least 500 bp having at least 97 percent sequence identity with a genome of a first CMV isolate or CMV strain and a second CMV sequence of at least 500 bp having at least 97 percent sequence identity with a genome of a second CMV isolate or CMV strain, and wherein said chimeric genome comprises genetic information having substantial identity (e.g., at least 80 percent sequence identity, preferably at least 95 percent sequence identity) spanning at least about the complete Toledo genome excepting at least 1 kbp of the virulence determinign region of Toledo (Toledo genome region), and preferably excepting at least 5 kbp to the entire approximately 15 kbp virulence-detemrning Toledo genome region. Typically, the chimeric genome comprises at least 500 bp containing at least one ORF having at least 95 to preferably 100 percent sequence identity to a virulence region of low-passage Towne.

In specific embodiments, the invention provides exemplary CMV chimeric viruses composed of genome portions of high-passage Towne and genome portions of Toledo; the exemplary CMV chimeric viruses are designated herein as Chimera I, Chimera II, Chimera III, Chimera IV, and Towne/ Tol 11. In an aspect, the invention encompasses these specific embodiments and variants of each exemplified Chimera wherein the boundaries (splice junctions/recombination joints) between the various Towne and Toledo genome portions vary from the specific exemplified Chimeras by less than 20 kbp, typically less than 10 kbp, usually by less than 5 kbp, and in many embodiments by less than 1 kbp from the specific examples provided herein.

In a variation, the invention provides a diagnostic method for identifying a virulent CMV strain in a sample by detecting the presence of unique Toledo genome region polynucleotide sequences and/or by detecting the presence of a polypeptide encoded by an open reading frame of the Toledo genomic region. Detection of polynucleotide sequences can be by any suitable method, including but not limited to PCR amplification using suitable primers, LCR, hybridization of a labeled polynucelotide probe, and the like. Detection of polypeptide speceis is typically done by immunoassay using a pecific antibody to the Toledo region gene product(s).

The invention also provides a method of treating or preventing CMV infection, the method comprising administering to an individual an efficacious dose of a polypeptide which is substantially identical to the deduced amino acid sequence of UL148. In a variation, the polypeptide is a truncated variant, mutein, or analog of the deduced amino acid sequence of UL148, wherein the polypeptide is soluble.

A further understanding of the nature and advantages of the invention will become apparent by reference to the remaining portions of the specification and drawings.

BRIEF DESCRIPTION OF THE DRAWINGS

FIGS. 1A–1R. Nucleotide sequence of Toledo genome region isolated from Toledo strain of HCMV (SEQ ID NO: 1).

FIGS. 2A–2H. Deduced amino acid sequences of open reading frames UL130, and UL132 through UL151 (SEQ ID NOs:2–27, respectively). Conventional single letter abbreviations are used.

FIG. 8. Southern blot showing that previous variants of the Towne strain hybridize to the Toledo $U_L/b'$ region. Twn•Merck indicates Towne strain from the Merck clinical trial. Twn•MA, Twn•MA#5 and Twn•MA#8 are variants of Towne obtained from Microbiological Associates. Twn•Aviron is highly-passaged Towne obtained at Aviron.

FIG. 9. Schematic depiction of generation of chimeric CMV virus genomes by cotransfection of cosmids containing portions of Towne and Toledo genomes.

DEFINITIONS

Figure 3:
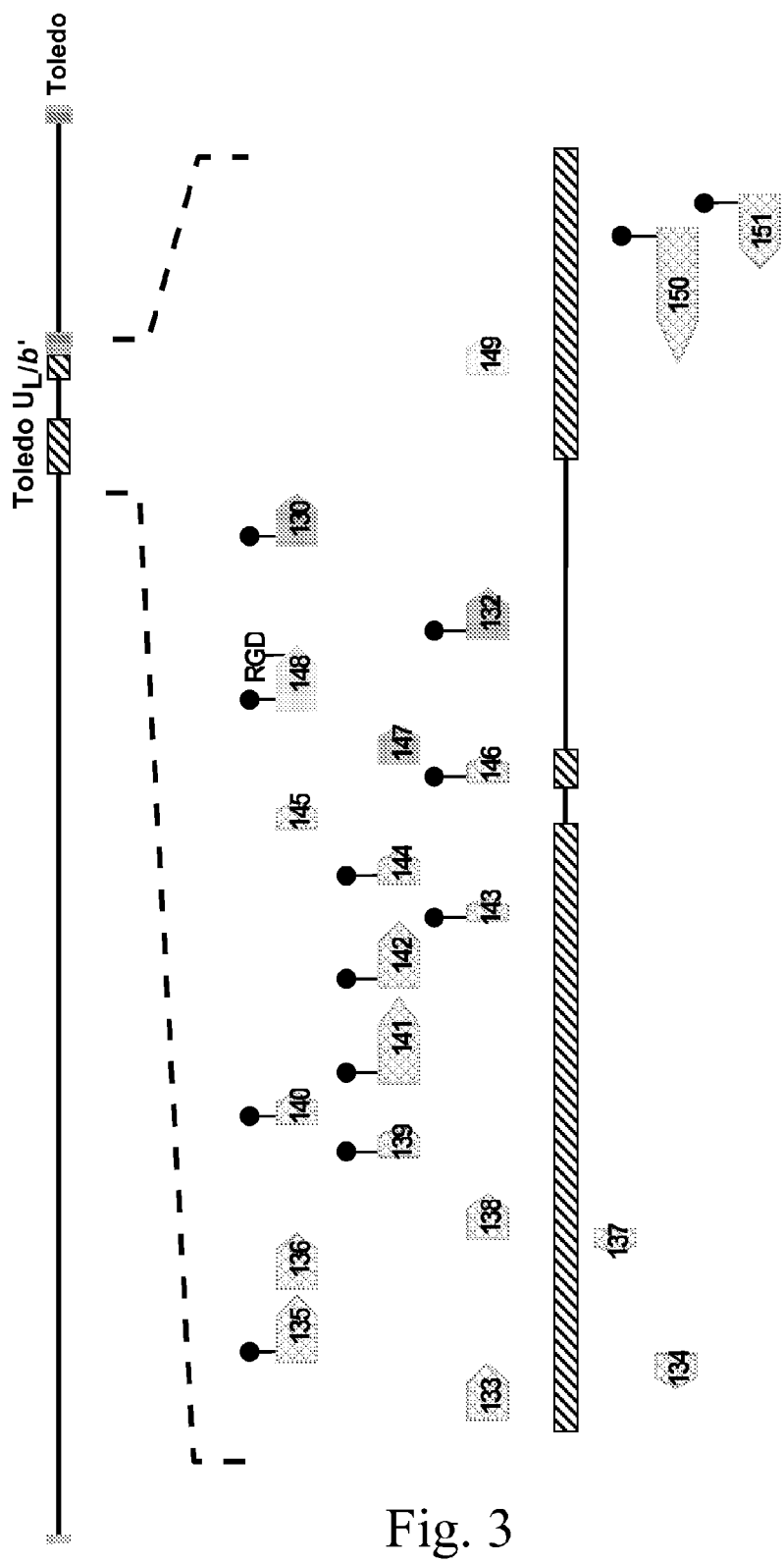
FIG. 3. Schematic representation of open reading frames and their location in Toledo genome region. Top line schematically portrays entire Toledo genome with $U_L/b'$ region identified. Bottom line shows enlarged view of $U_L/b'$ region. Arrows indicate polarity and length of open reading frame. Solid circles indicate potential glycosylation sites.
Figure 4:
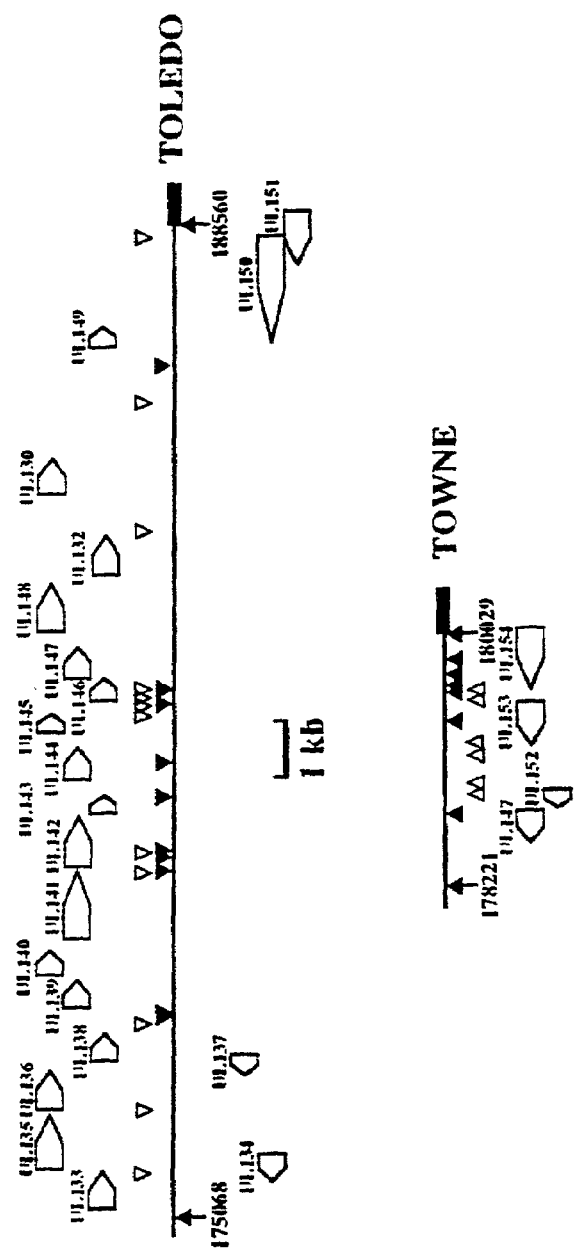
FIG. 4. Schematic comparison of the novel genome regions of Toledo and highly-passaged Towne as compared to AD169.
Figure 5:
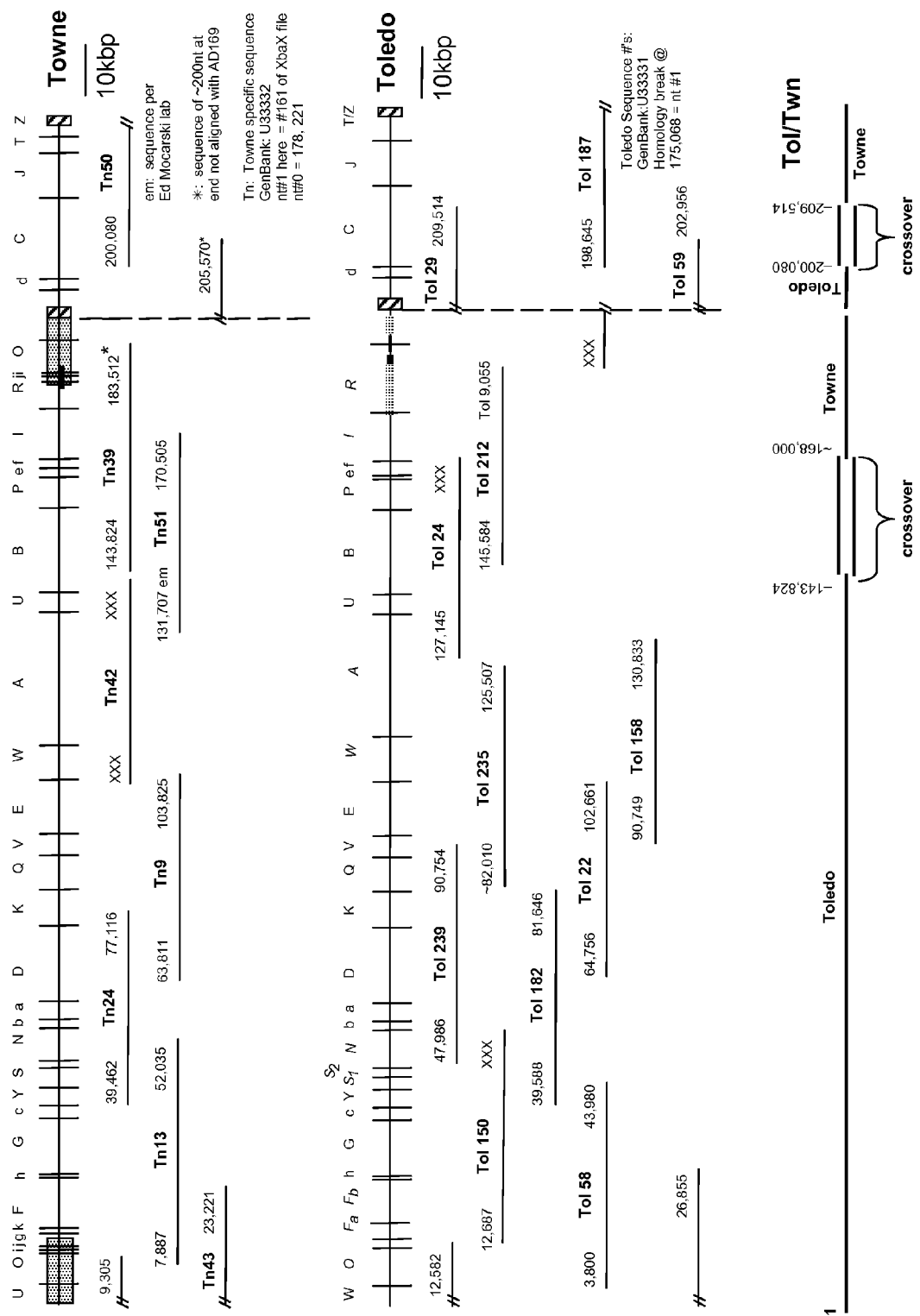
FIG. 5. CMV Towne and Toledo cosmids used to regenerate specific chimeric CMV viruses. The location of the cosmid insert are indicated beneath the appropriate viral genome. The numbers at the end of the insert denote the endpoints determined by DNA sequence analysis; the numbers correspond to AD169 genomic sequence in GenBank (EMBL accession number X17403). "XXX" "denotes an end which was refractory to DNA sequence analysis. These ends were mapped by restriction enzyme and Southern blot analyses. The vertical dashed line represents the location of the internal "a" sequence of the virus. The lower line depicts the structure of the Tol/Twn 39/50 genome. The thick gray line denotes sequences derived from Toledo and the thin black line depicts sequences contributed from highly-passaged Towne strain. Regions of overlap could be derived from either virus and are repregented by a region of a thick gray and a thin black line together. The Tol/Twn 39/50 genome does not contain the Toledo genomic region.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991)). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences" sequence regions on the DNA strand having the same sequence as the RNA and which are 3' to the 3' end of the coding RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATAT".

The following terms are used to describe the sequence relationships between two or more polynucleotides: "reference sequence", "comparison window", "sequence identity", "percentage of sequence identity", and substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1A–1R (SEQ ID NO. 1), or may comprise a complete cDNAa or gene sequence. A full-length cDNA or gene sequence is defined as a polynucleotide containing the sequence(s) necessary to encode a complete protein product, including a translation initiation codon and a translation termination codon, unless linked to another encoding sequence in a format for production as a fusion protein. Generally, a reference sequence is at least 20 nucleotides in length, frequently at least 25 nucleotides in length, and often at least 50 nucleotides in length. Since two polynucotides may each (1) comprise a sequence (i.e., a portion of the complete polynucleotide sequence) that is similar between the two polynucleotides, and (2) may further comprise a sequence that is divergent between the two polynucleotides, sequence comparisions between two (or more) polynucoeotides are typically performed by comparing sequences of the two polynucloeotides over a "comparison window" to identify and compare local regions of sequence similarity.

A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of an open reading frame shown in FIG. 1A–1R.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "analog", "mutein" or "mutant" as used herein refers to polypeptides which are comprised of a segment of at least 10 amino acids that has substantial identity to a portion of the naturally occurring protein The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition.

The term "agent" is used herein to denote a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as antineoplastics, anti-inflammatories, or apoptosis modulators by inclusion in screening assays described hereinbelow. Agents are evaluated for potential activity as specific protein interaction inhibitors (i.e., an agent which selectively inhibits a binding interaction between two predetermined polypeptides but which does not substantially interfere with cell viability) by inclusion in screening assays.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The term "primer" as used herein refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single-stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primers. For example, depending on the complexity of the target sequence, the oligonucleotide primer typically contains 15–25 or more nucleotides, although it may contain fewer nucleotides. Short primer molecules generally require cooler temperatures to form sufficiently stable hybrid complexes with template. In some embodiments, the primers can be large polynucleotides, such as from about 200 nucleotides to several kilobases or more. The primers herein are selected to be substantially complementary to the different strands of each specific sequence to be amplified. The primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, noncomplementary bases or longer sequences can be interspersed into the primer, provided that the primer sequence has sufficient complementarity with the sequence of the strand to be amplified to hybridize therewith and thereby form a template for synthesis of the extension product of the other primer.

The term "recombinant" used herein refers to macromolecules produced by recombinant DNA techniques wherein the gene coding for a polypeptide is cloned by known recombinant DNA technology. For example, an amplified or assembled product polynucleotide may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, Aspergillus and insect cells. One preferred embodiment employs bacterial cells as the host. Alternatively, the product polynucleotide may serve a non-coding function (e.g., promoter, origin of replication, ribosome-binding site, etc.).

DETAILED DESCRIPTION

Commonly-assigned U.S. patent application U.S. Ser. No. 08/414,926 filed 31 Mar. 1995 is incorporated herein by reference.

The nomenclature used hereafter and the laboratory procedures in cell culture, molecular genetics, and nucleic acid chemistry and hybridization described below may involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Stockton Press, New York, N.Y. (1989); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; and U.S. Pat. Nos. 4,683,202 and 4,965,188, each of which are incorporated herein by reference) and exemplified hereinbelow.

It is evident that optimal PCR and hybridization conditions will vary depending upon the sequence composition and length(s) of the targeting polynucleotide(s) and target(s), and the experimental method selected by the practitioner. Various guidelines may be used to select appropriate primer sequences and hybridization conditions (see, Maniatis et al., *Molecular Cloning: A Laboratory Manual* (1989), 2nd Ed., Cold Spring Harbor, N.Y.; Berger and Kimmel, *Methods in Enzymology, Volume* 152, *Guide to Molecular Cloning Techniques* (1987), Academic Press, Inc., San Diego, Calif.; *PCR Protocols: A Guide to Methods and Applications*, eds. Innis, Gelfland, Snisky, and White, Academic Press, San Diego, Calif. (1990); Benton W D and Davis R W (1977) *Science* 196: 180; Goodspeed et al. (1989) *Gene* 76: 1; Dunn et al. (1989) *J. Biol. Chem.* 264: 13057 which are incorporated herein by reference.

A basis of the invention is the unexpected discovery that there are significant genomic differences between clinical isolates of CMV and highly-passaged CMV strains, including differences between low-passage Towne and high-passage Towne, as well as differences as compared to Toledo strain; the identification of these genomic differences, including definition of novel genomic region(s); and the phenotypic significance and biological function of said genomic differences and specific ORFs within said novel genomic regions. Based, in part, on these unexpected discoveries, it is possible to construct and use chimeric CMV viruses which have predetermined genome compositions comprising at least a portion of a genome of a first CMV isolate or strain and at least a portion of a genome of a second (or subsequent) CMV isolate or strain, so as to form a complete, replicable recombinant chimeric CMV genome, with and the resultant chimeric CMV genome being capable of replication in a suitable host replication system and being useful for a variety of uses, such as human or veterinary vaccines, commercial reagents for laboratory use (e.g., as restriction enzymes are sold), use in screening systems to identify novel candidate drugs to inhibit replication or pathogenesis (e.g., virulence, tropism, host range, etc.) of pathogenic, clinically relevant CMV virus types, and other uses such as diagnostic reagents, gene expression vectors, anti-tumor agents, heterologous gene expression systems, and the like.

Overview

An approach of the invention starts with identification of DNA sequences which confer virulence on human cytomegalovirus (HCMV). These sequences can be manipulated to produce a new, more efficacious HCMV vaccine strain with predicted characteristics. Introduction of the virulence genes into an overattenuated strain can improve its immunogenicity and deletion of the virulence genes from a virulent strain can render it safe in humans by decreasing its virulence. Specifically, deletion of genetic information from a clinical isolate called Toledo is used to attenuate an HCMV virus, and in one embodiment, a segment from a laboratory strain called Towne, especially a highly-passaged Towne variant, is transferred to the deleted region of Toledo to act as a "spacer". Deleting genetic information has utility in improving a clinical isolate such as Toledo as an immunizing composition. Removing these sequences from Toledo, which has been shown to cause disease in people, can result in an attenuated virus which may be a safe vaccine candidate.

The Towne strain of HCMV has been used as a vaccine in humans. In some clinical settings, Towne has been used to prevent the disease consequences associated with infection by HCMV (reviewed by Marshall and Plotkin In: *The Human Herpesviruses* B. Roizman, R. J. Whitley, & C. Lopez Eds. Raven Press, New York). The Towne strain is believed to be overattenuated as a vaccine candidate and consequently, is poorly immunogenic. This loss of immunogenicity may have been the result of an extensive passage history in tissue culture. Genetic information in the virulence region may have been lost during passage, particularly after about Passage 40. Variation in DNA content among isolated strains does exist based on crude hybridization experiments. Other investigators have reported minor regions of sequence heterogeneity between two so-called laboratory strains of HCMV, the Towne and AD169 strains. Heterogeneities can exist within HCMV strains depending upon the extent of passages in their culture history.

The public health impact of HCMV infections have not been well controlled by current treatment strategies or available antiviral chemotherapies. Preventive vaccine strategies are likely to prove efficacious because of the observations that seropositive renal allograft recipients are protected from severe HCMV disease and maternal immunity protects the fetus from disease after intrauterine infection. HCMV (Towne) was developed as a vaccine strain by serial passage 125 times in WI38 human diploid fibroblasts (Towne 125). It has been administered to humans without significant adverse reactions. However, in one study, vaccinees were directly challenged by wild-type virus and found to resist only low challenge doses of 10 plaque-forming units or less. The consensus view is that the Towne strain may be overly attenuated. One positive feature of the Towne strain is that it has never been shown to reactivate.

One important obstacle to the development of a vaccine for HCMV is the lack of an animal model system that can be used to test the safety and efficacy of vaccine candidates. Therefore, cell culture systems or surrogate animal models such as the SCID-hu (thy/liv) mouse have to be developed to test vaccine strains. Replicative differences in HCMV strains have been described in a variety of cell types and in the SCID-hu mouse model. These differences correlate to the virulence and passage history of the virus. Thus, low passage, virulent clinical isolates, such as Toledo, can replicate better in the human implant of SCID-hu (thy/liv) mice and in cultures of human endothelial cells than cell culture adapted, highly-passaged avirulent laboratory strains such as Towne or AD169 (Brown et al. 1995; Waldman et al., 1991). This observation can be exploited to measure the "virulence" of a strain by assessing its growth characteristics in the SCID-hu mouse, in vivo in humans, or by other means. Recombinant vaccine candidates such as the ones described here which have deleted or incorporated DNA sequences are believed to replicate less well than the virulent parent in a suitable virulence assay. This observation would be indicative of an attenuated vaccine candidate. Deletion of the Toledo UL/b' region from the low passage, virulent HCMV Toledo genome results in a virus with reduced replicative ability in the SCID-hu mouse. This recombinant virus should have a concomitantly reduced virulence which allows administration of the virus without causing the undesired clinical manifestations exhibited by the Toledo virus in humans.

The invention identifies, maps, and sequences differences between the virulent Toledo strain and the avirulent highly passaged Towne strain, for the purpose of transferring novel genetic information to Towne to restore its immunogenicity or, alternatively, to remove information from Toledo to render it safe as a vaccine candidate. One major region of difference mapped to the internal portion of the L component. This large 13 kbp region present in Toledo but not highly passaged Towne is located at the border between the unique long (UL) and the inverted repeats bordering the UL region termed IRL or b'. We have deduced the coding information resident in the Toledo sequences and have extensively compared the information resident in AD169, highly passaged Towne and Toledo. We have made recombinant viruses which have either inserted the UL/b' region from the virulent Toledo strain, into the corresponding region of Towne, and have also deleted this region from Toledo and replaced it with a selectable marker and reporter gene or with the corresponding UL/b' region from Towne. Deletion of the virulence genes from Toledo decreased the ability of the recombinant to replicate within the SCID-hu (thy/liv) mouse, a model for CMV virulence. The new recombinant viruses exhibit growth properties in the SCID-hu mouse that indicate that vaccine candidates with attenuated virulence can be generated by deleting the UL/b' region from the Toledo virus. We have also demonstrated that we can add the Toledo region to the Towne virus which will presumably result in increased immunogenicity for the highly passaged Towne virus while retaining its safe profile for humans.

FIGS. 1A–1R show the nucleotide sequence of Toledo genome region isolated from Toledo strain of HCMV (SEQ ID NO. 1). FIGS. 2A–2H show the deduced amino acid sequences of open reading frames UL130, and UL132 through UL151 (SEQ ID NOs 2–27, respectively).

A basis of the present invention is the surprising and unexpected finding that: (1) clinical isolates of pathogenic CMV variants contain a genomic region which typically is not present in CMV strains which have undergone extensive laboratory passaging of the virus in cell culture, and (2) functional disruption (e.g., deletion or insertional inactivation and the like) of genes in this genomic region produces a substantial attenuation of CMV virulence and pathogenicity in vivo. The genomic region is conveniently termed the "Toledo genomic region" herein, although equivalent (e.g., homologous) regions or subsequences thereof are present in other clinical isolates of CMV besides the Toledo strain of CMV; the term "Toledo genomic region" encompasses these homologous regions in other clinical CMV isolates and non-isolated pathogenic CMV variants which have a genomic region of at least 500 bp having at least 80 percent sequence identity to the Toledo genomic region of the Toledo strain having the sequences disclosed herein and in WO96/30387, incorporated herein by reference. The Toledo genomic region which is present in pathogenic CMV isolates and which is typically substantially absent in laboratory passaged CMV strains (e.g., AD169, Towne) has been sequenced and several open-reading frames have been identified. Functional disruption of these open reading frames, either singly or in combination, has been unexpectedly found to substantially reduce virulence of the resultant CMV mutant(s) in vivo. Thus, in part, the invention provides methods and compositions for suppressing or inactivating expression of genes of the Toledo genomic region and its homolog regions in other CMV variants, and thereby reducing virulence and pathogenicity of clinically important CMV variants. The invention is, in part, further based on the heretofore unrecognized finding that pathogenic clinical isolates of CMV have a distinct genome as compared to the commonly used laboratory-passaged strains of human CMV (e.g., AD169, Towne), and that the genomic region which is present in the clinical isolates and which is substantially absent in laboratory-passaged strains confers enhanced virulence in vivo. Most common approaches to development of CMV therapies and vaccines have heretofore relied on laboratory-passaged strains which lack the Toledo genomic region and the genes encoded therein which have been unexpectedly found to confer enhanced in vivo virulence and are believed to contribute to clinical pathology and CMV-related disease.

The invention provides a method for attenuating virulence of CMV comprising functionally inactivating at least one open reading frame in a genomic region of a CMV genome having substantial identity to at least 300 bp, typically at least 500 bp, of an approximately 15 kb sequence present in the genome of the Toledo strain of CMV and absent from the genome of the AD169 strain of CMV. In an aspect, the method functionally inactivates at least one open reading frame present in a genomic region of a CMV genome having substantial identity to at least 300 bp of a 13 kb sequence present in the genome of the Toledo strain of CMV and absent from the genome of the highly-passaged Towne strain of CMV. In an embodiment, the method functionally inactivates at least one open reading frame present in a genomic region of a CMV genome having substantial identity to at least 500 bp of the sequence shown in FIGS. 1A through 1R (SEQ ID NO: 1). In an embodiment, the method functionally inactivates at least the open reading frame corresponding to UL 148 as identified herein. In a variation, the method functionally inactivates open reading frames in the region spanning UL138 to UL 148. In an embodiment, the method functionally inactivates UL138, UL139, UL140, UL141, UL 142, UL 143, UL144, UL145, UL146, UL147, and/or UL148. In a variation, UL148 is inactivated singly or in combination with other open reading frames of the Toledo genomic region. In a specific embodiment, UL148 is inactivated in combination with UL141 and/or UL144. Inactivation is typically accomplished by genetic engineering and involves predetermined mutations (which may include additions, transpositions, or deletions), generally of the specific type which are not known to occur naturally in CMV strains even after extensive passaging.

In an aspect, the method of attenuating virulence comprises functional inactivation of open reading frames by structural mutation (e.g., deletion, insertion, missense or nonsense mutation, and the like) of at least one open reading frame, or a mutation of a transcriptional control sequence that controls transcription of the open reading frame, or mutation of a splicing signal sequence or the like necessary for efficient expression of the encoded gene product of the open reading frame. In an embodiment, a selectable marker gene is introduced into an open reading frame, often in the portion of the open reading frame believed to encode the amino-terminal two-thirds of the gene product, to structurally disrupt the open reading frame and result in the inactivation of the open reading frame's capacity to encode its functional gene product. In a variation, open reading frame UL148 is structurally disrupted by predetermined mutation, often produced by site-directed mutagenesis or in vitro recombination; in one embodiment the structural disruption results from insertion of a selectable and/or screenable marker gene (e.g., gpt/lacZ). In an embodiment, a selectable marker gene is used to replace all or part of at least one open reading frame, such as by replacement of a deleted region of the Toledo genomic region with a selectable marker gene. In a variation, a region spanning open reading frame UL138 to UL148 is structurally disrupted by predetermined mutation; in one embodiment the structural disruption results from deletion of the UL138–UL148 region and replacement with a selectable and/or screenable marker gene (e.g., gpt/lacZ).

In an aspect, the functional inactivation of a Toledo genomic region gene is provided by transcriptional and/or translational suppression with an antisense polynucleotide having a sequence of at least 15 nucleotides, typically at least 25 nucleotides, that are substantially complementary to a Toledo genomic region, most usually the antisense polynucleotide is substantially complementary to an open reading frame sequence of a Toledo genomic region open reading frame. In an embodiment, the antisense polynucleotide is substantially complementary to at least 25 nucleotides of UL148. In an embodiment, the antisense polynucleotide is complementary to UL148 and further comprises additional 5' and/or 3' nucleotide(s) which are not substantially complementary to UL148. In variations, the antisense polynucleotides comprise non-natural chemical modifications, and can include, for instance, methylphosphonates, phosphorothioates, phosphoramidites, phosphorodithioates, phosphorotriesters, and boranophosphates. In a variation the antisense molecules can comprise non-phosphodiester polynucleotide analogs wherein the phosphodiester backbone is replaced by a structural mimic linkage include: alkanes, ethers, thioethers, amines, ketones, formacetals, thioformacetals, amides, carbamates, ureas, hydroxylamines, sulfamates, sulfamides, sulfones, and glycinylamides. In a variation, the invention provides peptide nucleic acids (PNAs) having a nucleobase sequence which is substantially complementary to a Toledo genomic region sequence, such as an open reading frame (e.g., UL148, UL141, UL142, etc.).

The invention also provides attenuated live virus CMV vaccines wherein at least one open reading frame of a Toledo genomic region is structurally disrupted by predetermined mutation. Typically, the UL148 open reading frame is structurally disrupted, either singly or in combination with other Toledo region open reading frames (e.g., UL141, UL144, and the like). Often the disruption of the open reading frame is an insertion, deletion, or replacement mutation which confers the property of reduced virulence as determined by a suitable in vivo virulence assay (e.g., see Experimental Examples). Toledo genomic region mutants which exhibit at least one log reduction, preferably two logs or more reduction, in virulence as determined by in vivo virulence assay, or other equivalent virulence measure, are attenuated CMV vaccines. Such attenuated CMV vaccines are used to immunize individuals to confer protective immunity, typically antibody-mediated and/or cell-mediated immunity, to prevent or reduce the severity of subsequent CMV infection following a suitable immunization period.

In an aspect, the invention also provides attenuated live virus CMV vaccines wherein at least one open reading frame of a Toledo genomic region is replaced by a segment of Towne genome which is not present in AS169. The highly-passagedTowne genome comprises a region no present in AD169; the region contains open reading frame designated UL147, UL152, UL153, and UL154 and generally is spanned by nucleotides 178221 to 180029 of the Towne genome according to the AD169 (EMBL accession number X17403) numbering convention. An attenuated virus of the invention can, in one embodiment, comprise a Toledo genome wherein the Toledo genome region spanning open reading frames UL133 to UL151 are replaced with a Towne genome region spanning UL147, UL 152, UL153, and UL154; this engineered CMV virus variant is an attenuated Toledo virus which comprises desirable features of Towne while reducing undesirable virulence of the Toledo genome region. The invention provides other variations of this basic method, whereby a segment of the Toledo genome region comprising at least one open reading frame is deleted or otherwise structurally disrupted in a CMV variant having a Toledo genome region or its homolog, and a segment of a Towne genome region comprising at least one open reading frame in inserted in the CMV variant. In an embodiment, the engineered CMV variant comprises: (1) Toledo DNA (DNA substantially identical to a Toledo strain, preferably identical to it) from about nucleotides 1 to about 168,000 corresponding to (i.e., according to) the AD169 nucleotide (EMBL accession number X17403) numbering convention, operably linked to (2) Towne DNA (DNA substantially identical to a Towne strain, preferably identical to it) from about nucleotides 143,824 to 189,466 according to the AD169 nucleotide (EMBL accession number X17403) numbering convention, operably linked to (3) Toledo DNA (DNA substantially identical to a Toledo strain, preferably identical to it) from about nucleotides 189,466 to about 209,514 corresponding to (i.e., according to) the AD169 nucleotide (EMBL accession number X17403) numbering convention, operably linked to (4) Towne DNA (DNA substantially identical to a Towne strain, preferably identical to it) from about nucleotides 200,080 to 229,354 according to the AD 169 nucleotide (EMBL accession number X17403) numbering convention. The invention also provides vaccine compositions and formulations of such attenuated CMV viruses, which can include adjuvants, delivery vehicles, liposomal formulations, and the like. The invention also provides the use of such attenuated CMV variants for prevention of CMV disease and infection; in one aspect this use includes administration of such vaccine to human subjects.

In a variation, the functional inactivation of a Toledo genomic region gene is provided by suppressing function of a gene product encoded by a Toledo region open reading frame by contacting or administering an antibody which is specifically reactive with said gene product. In an embodiment, the Toledo genomic region gene is UL148, UL141, and/or UL144, typically at least UL148, although other Toledo open reading frames can be used. The antibody binds to a gene product encoded by a Toledo region open reading frame with an affinity of at least about $1 \times 10^7$ $M^{-1}$, typically at least about $1 \times 10^8$ $M^{-1}$, frequently at least $1 \times 10^9$ $M^{-1}$ to $1 \times 10^{10}$ $M^{-1}$ or more. In some aspects, the antibody is substantially monospecific. In an embodiment, the antibody is a human antibody raised by immunizing an individual with an immunogenic dose of a gene product of a Toledo region open reading frame. In an embodiment, the human antibody is a monoclonal antibody, or collection of human monoclonal antibodies which bind to the Toledo region gene product(s). In an embodiment, the antibody is a humanized antibody comprising complementarity-determining regions substantially obtained from a non-human species immunoglobulin reactive with the Toledo region gene product, and further comprising substantially human sequence framework and constant regions. The invention also comprises pharmaceutical formulations of such antibodies and the use of such antibodies to treat or prevent CMV diseases, such as by passive immunization or the like.

In an aspect, the invention provides a composite CMV variant comprising a Towne genome and at least one open reading frame of a Toledo genome region, typically present in or adjacent to the $U_L/b'$ region of the composite CMV. In an aspect, the composite CMV is a Towne genome further comprising a Toledo UL148, UL141, and/or UL144. In an embodiment, the composite CMV is a highly-passaged Towne genome with a complete Toledo genome region; in a variation said Toledo genome region has at least one open reading frame functionally inactivated to further attenuate the virulence of the composite CMV.

In a variation, the invention provides a diagnostic method for identifying a virulent CMV strain in a sample by detecting the presence of unique Toledo genome region polynucleotide sequences and/or by detecting the presence of a polypeptide encoded by an open reading frame of the Toledo genomic region. Detection of polynucleotide sequences can be by any suitable method, including but not limited to PCR amplification using suitable primers, LCR, hybridization of a labeled polynucelotide probe, and the like. Detection of polypeptide speceis is typically done by immunoassay using a pecific antibody to the Toledo region gene product(s).

The invention also provides a method of treating or preventing CMV infection, the method comprising administering to an individual an efficacious dose of a polypeptide which is substantially identical to the deduced amino acid sequence of UL148. In a variation, the polypeptide is a truncated variant, mutein, or analog of the deduced amino acid sequence of UL148, wherein the polypeptide is soluble.

Experimental Examples

Overview

The growth advantage of Toledo in the SCID-hu mouse model resides in the genetic information encoded by the additional sequences (Toledo genomic region) we have identified. One gene in particular, UL148, has been mutagenized in Toledo by insertion of a selectable marker (gptILacZ) and the Toledo-based recombinant has been shown to replicate less well than Toledo in the SCID-hu assay. The genetic information of the corresponding region of the avirulent Towne virus has been deduced by nucleotide sequence analysis and demonstrated to lack an open reading frame in Towne. UL148 can be considered to be representative of a "virulence determinant" for Toledo. The new Toledo sequence identified at the inverted repeats has been analyzed to reveal novel genes in Toledo. Deletion of genes encompassing UL138 to UL148 in recombinant viruses have been tested for growth properties in the SCID-hu (thy/liv) mouse. These recombinants have been shown to replicate to levels similar to the Towne virus and represent attenuated vaccine candidates, since Towne has been shown to be safe and avirulent in humans. Such recombinants should show increased immunogenicity owing to their greater similarity to low passage virulent strains over that shown by highly-passaged Towne in humans. In addition, these strains should not exhibit the fully virulent phenotype shown by unmodified Toledo in humans due to the alterations we have introduced into their genomes.

This invention describes new recombinant HCMV viruses not previously described which are attenuated in virulence relative to low passage, virulent isolates by virtue of deletion of sequences shown to be present in low passage, virulent isolates but which are lacking in laboratory strains. The identification of these sequences was essential in order to prepare transfer vectors capable of shuttling deletions (or insertions such as selectable markers) resulting in an effective removal of coding information. Knowledge of the ORF usage on these DNAs permits deletion or insertion of one DNA into the other to specifically disrupt existing coding information. In addition, this invention identifies sequences which can be used as "spacer" DNA for substitution into deleted regions of HCMV clinical isolates for purposes of attenuation.

Cosmid Subclones of Towne and Toledo

Cosmid subclones of the CMV(Towne) and CMV(Toledo) genomes were constructed according to the method of Kemble et al. (1996) *J. Virol.* 70: 2044, incorporated herein by reference. Human foreskin fibroblast (HF) cells were infected with either Towne or Toledo and following the development of extensive CPE, DNA was isolated from nucleocapsids by a procedure similar to that used for the preparation of HSV nucleocapsids (Denniston et al. (1981) *Gene* 15: 365, incorporated herein by reference). The DNA was partially digested with Sau3AI, fractionated by agarose gel electrophoresis, and ligated to the BamHI site of BamHI, XbaI digested arms of the SuperCos•A1 cosmid vector. SuperCos•A1 was derived from SuperCos-1 (Stratagene, San Diego, Calif.) by the insertion of an oligonucleotide incorporating SrfI and PacI recognition sequences flanking a unique BamHI site. The position of the cosmid subclones relative to the viral genome was identified by Southern and DNA sequence analyses.

Overlapping Cosmids for Virus Regeneration

Mapping the extent of the viral insert within the cosmid subclones was used as a basis to form specific Towne/Toledo chimeric viruses by choosing the appropriate cosmids from each virus. The ends of adjacent cosmids should overlap (~200 bp or more) such that homologous recombination is permitted in eucaryotic cells.

To construct a Toledo based virus which lacked the Toledo $U_L$/b' region and in its place contained the Towne $U_L$/b' region, the following set of cosmids was used: Tol29, Tol58, Tol182, Tol22, Tol158, Tol124, Tn39, and Tn50. The resulting virus was designated Tol/Twn 39/50 (see FIG. 5). Other viruses were regenerated by cosmid cotransfection which lacked portions of the Toledo $U_L$/b' region. Toledo based viruses were generated by the cotransfection of the Toledo cosmids, Tol29, Tol58, Tol182, Tol22, Tol158, Tol24, Tol 212, Tol187 OR Tol59, Tol150, Tol239, Tol235, Tol158, Tol24, Tol212, Tol187. Towne/Toledo chimeras lacking portions of the Toledo $U_L$/b' region were regenerated by cotransfection of Tn43, Tn13, Tn24, Tn9, Tn42, Tn51, Tol212, Tol187. Because Tol 212 and Tol187 did not overlap, deletions resulted in the viruses regenerated from these cosmid sets which lacked varying portions of the Toledo $U^L$/b' region.

Preparation of Cosmids for Cotransfection

A set of overlapping cosmid clones constituting the appropriate viral genome were individually digested with PacI to release the intact viral insert from the cosmid vector. The restriction enzyme was inactivated by heating at 65° C. for 20 minutes, the cosmids were combined and the DNA precipitated with ethanol. A $CaPO_4$ precipitate was formed from approximately 8 to 16 μg of this mixture and transfected using general transfection methods. The DNA was transfected into approximately $1\times10^6$ low passage (<15 passes) HF, LF (human embryonic lung fibroblast) or IFIE1.3 (a gift of Ed Mocarski; these cells are immortalized HF cells that express the CMV major immediate early protein) cells. All these cells are permissive for CMV replication.

For HF and LF cells, approximately $1\times10^6$ cells were plated onto a 25 $cm^2$ flask 3 to 5 hours prior to the addition of the DNA-$CaPO_4$ precipitate. At this point, the precipitate was adsorbed directly to the cell monolayer for 30 minutes prior to the addition of media. 2 ml of media was added and incubation continued for 4 hours at 37° C.

For IFIE1.3 cells, the cells were trypsinized approximately 16 hours prior to the addition of the DNA-$CaPO_4$ precipitate and seeded at a 1:2 density. At the appropriate time post seeding, the DNA-$CaPO_4$ precipitate was added in addition to 2 ml of media and incubated at 37° C. for 4 hours.

Following the 4 hour incubation, the DNA-$CaPO_4$ precipitate was removed, the cells incubated at 37° C. for 3 min in 15% glycerol in Hepes buffered saline, rinsed one time with media and fed with 5 ml of media. The media on the cells was changed every 3 to 4 days and plaques appeared in 10 to 21 days.

Construction of Recombinant CMV by Insertion of a gpt/LacZ Marker

Two plasmids encompassing the Toledo $U_L$/b' region and derivatives thereof were constructed which contained a marker gene. A segment of DNA encompassing AD169 bases 156251–174483 was removed from pON2601 (Cha et al. (1996) *J. Virol.* 70: 78, incorporated herein by reference) and a PacI linker was introduced at AD169 base 174484 to yield a subclone of pON2601. FIGS. 3 and 4 show a schematic drawing of the open reading frames in the Toledo $U_L$/b' region using sequence numbering from the Toledo $U_L$/b' region DNA insert. A 4.8 kb DNA fragment containing the *E. coli* gpt and lac Z genes driven by the HSV thymidine kinase and β actin promoters (Prichard et al. (1996) *J. Virol.* 70: 3018, incorporated herein by reference), respectively, was then inserted into the NsiI site in Toledo UL148 within the pON2601 subclone. The resulting plasmid containing the gpt and lacZ insert in UL148 was designated pGD6. Toledo open reading frames UL138 to UL148 were removed from pGD6 by a BamHI collapse to produce the plasmid pGD7. Toledo recombinant viruses Tol pGD6 and Tol pGD7 were constructed using plasmids pGD6 and pGD7, respectively, as described (Prichard et al. (1996) *op.cit.*

Analysis of Recombinant CMV in SCID-hu (thy/liv) Mice

SCID-hu (thy/liv) mice were derived by implanting human fetal thymus and liver beneath the kidney capsule of a female C.B. -17 scid/scid IcrTac mouse (McCune et al. (1988) *Science* 241: 1632, incorporated herein by reference). The SCID-hu (thy/liv) mouse model serves as an animal model that can distinguish virulent from avirulent strains of CMV based on their replication levels within the human implant (Mocarski et al. (1993) *Proc. Natl. Acad. Sci.* (*U.S.A.*) 90: 104 and Brown et al. (1995) *J. Infect. Dis.* 171 1599, each incorporated herein by reference). Several weeks following implantation, the human implant on the murine kidney was surgically exposed and an inoculum of ~$10^4$ PFU of the appropriate virus was injected directly into the human tissue in a volume of 10–25 µl. The murine kidney/human implant was placed back into the animal in its natural position and the animal was recovered. 2 weeks following infection of the human tissue, the animal was sacrificed and the implant was removed and added to 2 ml of 4.5% skim milk/50% media.

The excised implant was homogenized with an automated Dounce apparatus (Glas-Col, Terre Haute, Ind.) and the suspension was stored at −80° C. until the titers were determined. The suspension was thawed at 37° C., sonicated on ice by three cycles of 10 sec on/10 sec off and centrifuged to remove the debris. The supernatent was recovered and the titer of CMV present was determined on confluent monolayers of HF cells. 7 to 10 days after plating the virus, the monolayers were fixed and stained with Giemsa and plaques enumerated.

Figure 6:
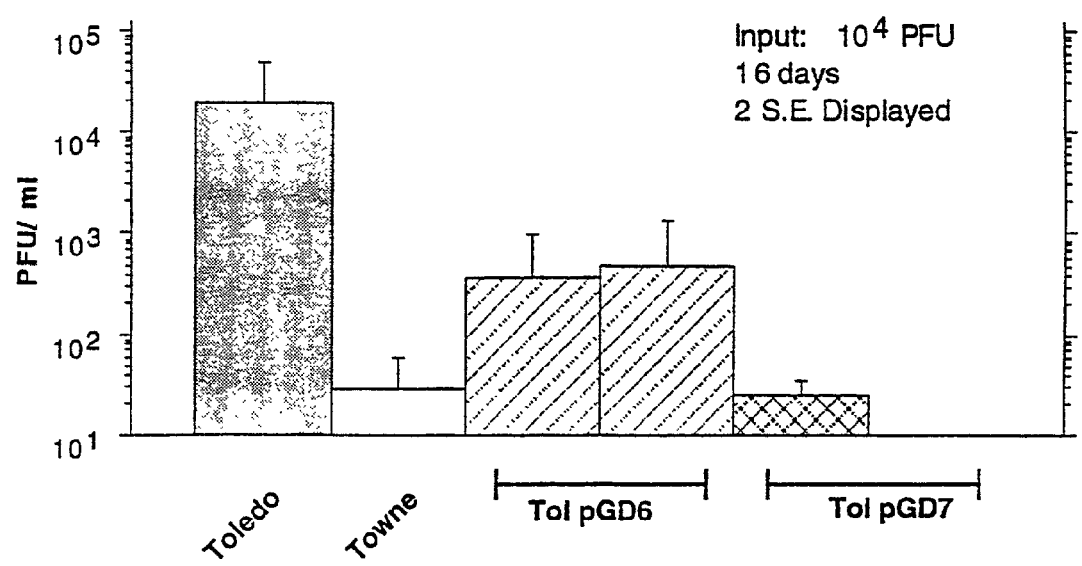
FIG. 6. Analysis of the gpt/LacZ recombinant viruses in the SCID-hu (thy/liv) model. Two independent isolates of Tol pGD6 and Tol pGD7 were tested in the model. 3 mice were used per group and the mean of the data is displayed. Error bars representing 2 standard errors from the mean are also displayed.
Figure 7:
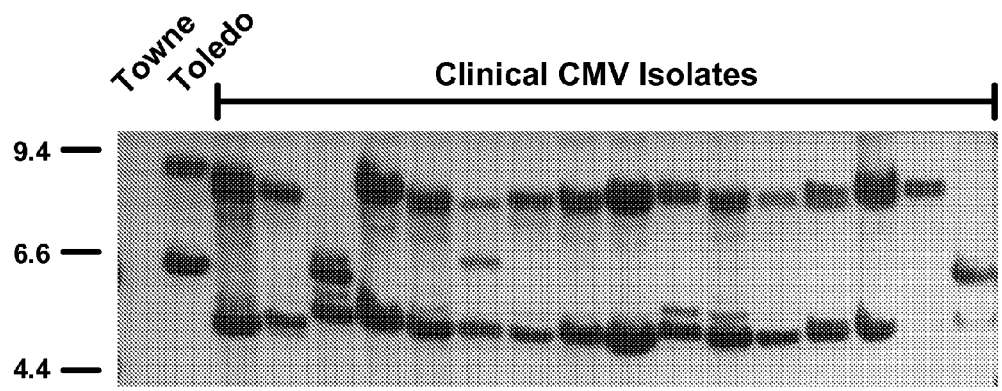
FIG. 7. Southern blot showing that a variety of clinical isolates of CMV contain sequences homologous to the Toledo $U_L/b'$ region. The Towne lane contains genomic DNA from Aviron's highyl-passaged Towne strain (Towne AV).

FIG. 6 shows results from this experiment. The virulence of the Toledo strain CMV is attenuated by functional disruption of Toledo genome region open reading frames.

The difference in virulence between the Towne and Toledo strainsappears to have resulted from genetic differences generated during the adaptation of Towne to growth in dipoid fibroblasts in culture. Both Towne and Toledo were originally isolated from the urine of a congenitally infected infant. Towne was subsequently passaged over 125 times in culture resulting in genetic alterations in the viral genome and an avirulent virus. The virulent Toledo virus, in contrast, was passaged approximately 5 times in diploid fibroblasts in order to produce material that could cause disease in humans.

These linked genetic and biological differences can be used to create a live, attenuated HCMV vaccine. The rationale for tissue culture adaptation of Towne was to generate a live, attenuated vaccine strain. Towne has been shown to be safe and somewhat immunogenic. Towne, however, is overattenuated. The immune response induced by inoculation with Towne does not protect against subsequent HCMV infection as effectively as that generated by natural infection. Vaccine candidates can be generated by replacing genetic elements of the overattenuated Towne strain with homologous portions of the virulent Toledo strain. Through the analysis of these "chimeric" viruses, a skilled artisan can select those that have the level of desirable characteristics of Towne and be attenuated to a more efficacious degree.

Figure 10:
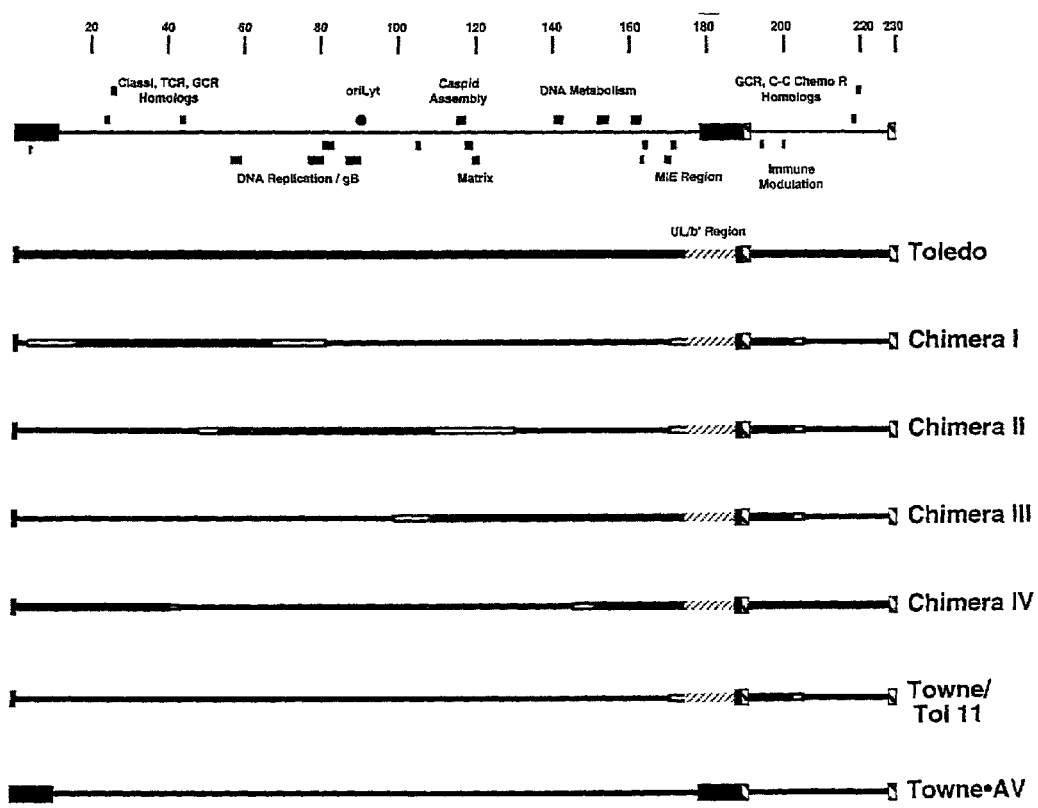
FIG. 10. Schematic deptiction of the specific exemplary embodiments denoted Chimera I, Chimera II, Chimera III, Chimera IV, and Towne/Tol 11. Toledo genome is depicted as "Toledo"; highly-passaged Towne genome is depicted as "Towne•AV"; selected reading frames of importance, proposed function/homologues of selected ORFs, and scale (in kbp) is shown on the top line.

Our first four chimeric viruses, as a set, will contain the entire Toledo genome introduced into the Towne genetic background. Each individual chimera of the set will contain approximately 40–55% of the Toledo genome; the remainder will be derived from Towne. Each of these chimeras will contain the UL/b' region derived from Toledo. Genes within this region of the Toledo genome can affect cell tropism of HCMV. The viruses, designated chimera I, II, III, and IV were constructed from the cosmids listed in Table 1 (see also FIGS. 9 and 10).

TABLE 1

Cosmids used to generate specific chimeras.

| Viruses | | | |
|---|---|---|---|
| I | II | III | IV |
| Tn46a | Tn46 | Tn46 | Tol29 |
| Tol58b | Tn45 | Tn45 | Tol58 |
| Tol182 | Tol239 | Tn23 | Tn23 |
| Tn47 | Tol22 | Tn47 | Tn47 |
| Tn44 | Tol158 | Tol184 | Tn44 |
| Tn26 | Tn26 | Tol24 | Tn26 |
| Tn20 | Tn20 | Tol212 | Tol212 |
| Tol11 | Tol11 | Tol11 | Tol122 |

Large quantities of each cosmid were prepared by purification of the *E. coli* produced material over a Qiagen column as described by the manufacturer. 10 micrograms of each cosmid was digested with the restriction enzyme Pac I (New England Biolabs) to physically separate cosmid vector from viral sequences. Following digestion, the enzyme was inactivated by incubation at 65° C. for 20 minutes and the appropriate cosmids were combined, precipitated with ethanol in the presence of 0.3M sodium acetate, rinsed in 70% ethanol, and air-dried briefly. The resulting DNA was solubilized in approximately 100 microliters of 10mM Tris pH 7.5/1 mM EDTA. Various amounts of the cosmid mix was transfected by the calcium phosphate technique into permissive fibroblast cells, specifically human lung fibroblasts (LF, prepared in our laboratory), human neonatal foreskin fibroblast (HF, a gift of Dr. Ed Mocarski, Stanford University), MRC-5 (ATCC) or IFIE1.3 cells (a gift of Ed Mocarski, Stanford University). The IFIE1.3 cell line constitutively expresses the HCMV ie1 gene product and has been transformed with the human papilloma virus E6 and E7 genes transduced by a retrovirus vector. 3 to 5 hours after transfection the cells were shocked by incubation in 15% glycerol/Hepes buffered saline for 3 minutes at 37° C. and fed with DME/10% fetal bovine serum. 7 to 10 days after transfection plaques with distinct HCMV CPE were evident.

Plaques derived from the chimeras were allowed to grow until 100% of the monolayer exhibited CPE. At this point, DNA was extracted from the supernatant and cellular fractions and analyzed by restriction enzyme digestion. The structures of the viruses can be deduced by the cosmids used for construction of the chimera and confirmed by comparing the EcoRI digestion pattern to the maps derived for Towne and Toledo (see FIG. 10). Table 2 describes the composition of each of the chimeras, the nucleotide limits are derived from sequence analysis of the end of each cosmid insert and its homology to the AD169 strain of HCMV, which has been sequenced in its entirety (EMBL accession number X17403). All of the chimeras had restriction enzyme patterns consistent with the proposed structures.

TABLE 2

Genetic composition of the chimeras.

| Chimera | Towne DNA | Toledo DNA | Crossover Region |
|---|---|---|---|
| I | 1–3799 | 15750–67568 | 3800–15749 |
| | 81647–170499 | 175069–203136 | 67569–81646 |
| | 205803 to S term. | | 170500–175068 |
| II | 1–47985 | 53244–~110000 | 47986–53243 |
| | 138834–170499 | 175069–203136 | ~110000–130833 |
| | 205803 to S term. | | 170500–175068 |
| | | | 203137–205802 |
| III | 1–~99000* | 108094–203136 | ~99000–108093 |
| | 205803 to S term | | 203137–205802 |
| IV | 43981–145583 | 1–41356 | 41357–43980 |
| | | 150754–S term | 145584–150753 |

*Sequence at end of cosmid was undefinable. Nucleotide number is not exact crossover region is the region of cosmid overlap. The contribution of each virus to this region has yet to be defined.

Figure 11:
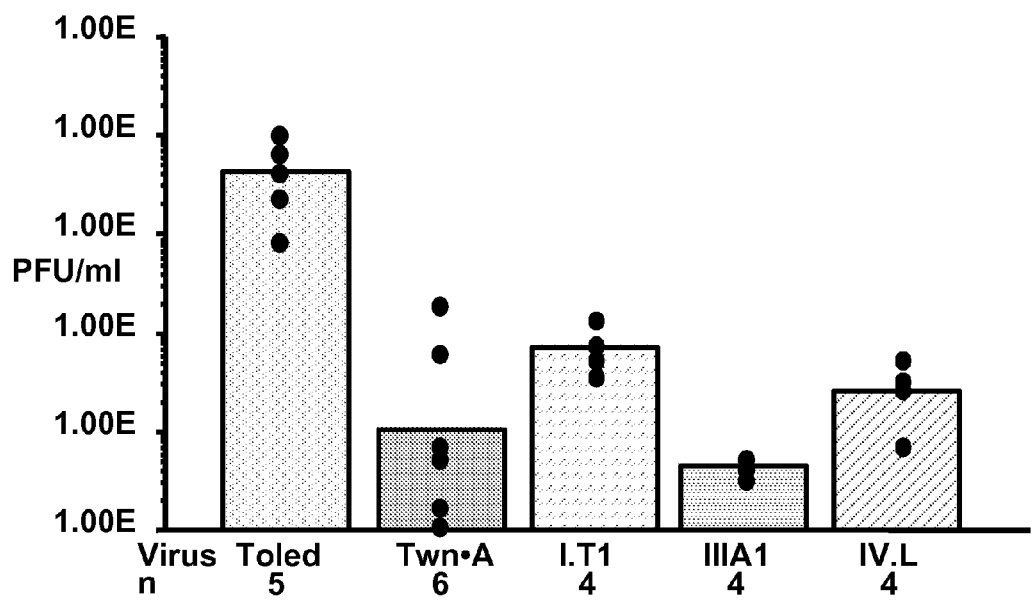
FIG. 11. Replication of Toledo, highly passaged Towne, and Chimeras I, III, and IV (in order, respectively) in SCID-hu mice having a thymus/liver implant.

Two other chimeras are constructed based on an observation derived from the sequence analysis of several different members of the beta-herpesvirus family including HCMV, human herpesvirus 6 (the causative agent of roseola) and murine cytomegalovirus. Representative members of each of these viruses have been sequenced in their entirety and a "core" set of genes corresponding to HCMV UL23 to UL122 are conserved among these evolutionarily divergent entities (Chee, et al. 1990; Gompels, et al. 1995; Rawlinson, et al. 1996, incorporated herein by reference). These core genes contribute to DNA replication, virion structure, and other basic features of the virus. Genes outside this core region are involved in virus-host and virus-immune system interaction and may determine specific properties of virus biology. Replication of the Chimeras was tested in SCID-hu mice having a thy/liv sandwich under the kidney capsule; representative data is shown in FIG. 11.

Two additional chimeras are constructed: one which has the core derived from Toledo with the remainder of the genes derived from Towne and an inverse construct in which the core is derived from Towne and the remainder of the genes are from Toledo. These viruses are constructed through the use of overlapping cosmids and derivatives of the cosmids. Table 3 outlines the constructs that can be used to generate these two chimeric viruses.

TABLE 3

Construction of chimeras containing conserved core regions.

| Towne Core/Tol Noncore | Tol Core/Towne Noncore |
|---|---|
| Tol29 | Tn43 |
| Tol58 nts: 3800–27862 | Tn45 nts: 7854–27862 |
| Tn45 nts: 27500–53243 | Tol58: 27500–43980 |
| Tn23 | Tol182 |
| Tn47 | Tol22 |
| Tn44 | Tol158 |
| Tn26 | Tol24 |
| Tn20 | Tol212 nts: 145584–17200 |
| Tol11 nts: 170852–188890 | Tn39 nts: 170852–183512 |
| Tol122 | Tn15 |

All of these viruses are used to inoculate healthy adult human volunteers. These individuals are assessed for symptoms of HCMV disease, including fever, malaise, and abnormal liver enzyme levels. Hallmarks of viral infection are also assessed by measuring HCMV specific antibody titers before and after inoculation as well as viral culture for the isolation of infectious virus from bodily fluids. A successful vaccine candidate is identified as a strain that maintains the safety profile of Towne while stimulating a greater immune response to the virus.

Figure 12:
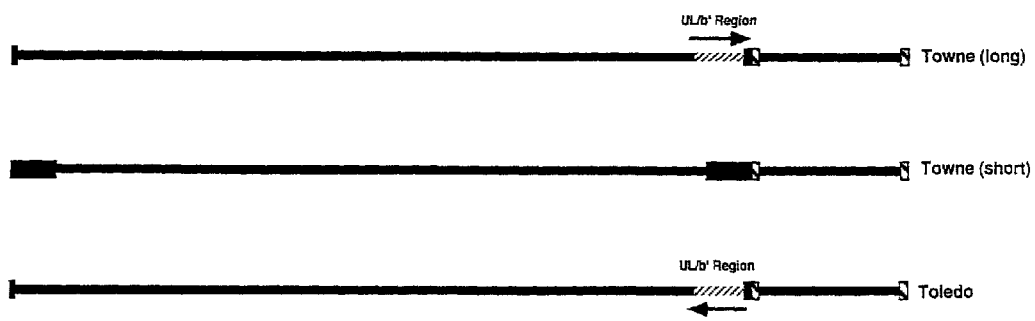
FIG. 12. Schematic comparison of low-passage (long) Towne genome and high-passage (short) Towne genome.

FIG. 12 shows schematic depiction of the Toledo genome incomparison with highly passaged Towne (short genome) and low-passage Towne (long genome).

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

The invention claimed is:

1. A chimeric cytomegalovirus (CMV) virus which comprises:
(a) a polynucleotide sequence of a high-passage Towne genome from nucleotides 1 to 3799; (b) a polynucleotide sequence of a Toledo genome from nucleotides 15750 to 67568; (c) a polynucleotide sequence of a high-passage Towne genome from nucleotides 81647 to 170499; (d) a polynucleotide sequence of a Toledo genome from nucleotides 175069 to 203136; and (e) a polynucleotide sequence of a high passage Towne genome from nucleotides 205803 to S-term, wherein the high-passage Towne genome has been passaged at least 50 times and wherein the nucleotide number of the Towne and Toledo genomes is according to the numbering convention of the AD169 genome.

2. A chimeric CMV virus which comprises: (a) a polynucleotide sequence of a high-passage Towne genome from nucleotides 1 to 3799;
(b) a crossover region comprising SEQ ID NO.: 28; (c) a polynucleotide sequence of a Toledo genome from nucleotides 15750 to 67568; (d) a crossover region comprising SEQ ID NO.: 29; (e) a polynucleotide sequence of a high-passage Towne genome from nucleotides 81647 to 170499; (f) a crossover region comprising SEQ ID NO.: 30; (g) a polynucleotide sequence of a Toledo genome from nucleotides 175069 to 203136; (h) a crossover region comprising SEQ ID NO.: 31 and (i) a polynucleotide sequence of a high passage Towne genome from nucleotides 205803 to S-term, wherein the high-passage Towne genome has been passaged at least 50 times and wherein the nucleotide number of the Towne and Toledo genomes is according to the numbering convention of the AD169 genome.

3. An immunogenic composition comprising the chimeric virus of claim 1.

4. An immunogenic composition comprising the chimeric virus of claim 2.

5. A method of inducing an immune response comprising administering to a human the immunological composition of claim 3 in an amount sufficient to stimulate an immune response in said human.

6. A method of inducing an immune response comprising administering to a human the immunological composition of claim 4 in an amount sufficient to stimulate an immune response in said human.

* * * * *

SEQUENCE LISTING

```
<160> NUMBER OF SEQ ID NOS: 31

<210> SEQ ID NO 1
<211> LENGTH: 18318
<212> TYPE: DNA
<213> ORGANISM: Human cytomegalovirus
<220> FEATURE:
<221> NAME/KEY: misc_feature
<222> LOCATION: (17955)..(17955)
<223> OTHER INFORMATION: n is a, c, g, or t
<220> FEATURE:
<221> NAME/KEY: misc_feature
<222> LOCATION: (18105)..(18105)
<223> OTHER INFORMATION: n is a, c, g, or t
<220> FEATURE:
<221> NAME/KEY: misc_feature
<222> LOCATION: (18154)..(18154)
<223> OTHER INFORMATION: n is a, c, g, or t
<220> FEATURE:
<221> NAME/KEY: misc_feature
<222> LOCATION: (18160)..(18160)
<223> OTHER INFORMATION: n is a, c, g, or t

<400> SEQUENCE: 1
```

-continued

```
cgctgtaggg ataaatagtg cgatggcgtt tgtgggagaa cgcagtagcg atgggttgcg      60
acgtgcacga tccttcgtgg caatgccaat ggggcgttcc cacgattatc gtggcctgga     120
taacatgcgc ggctttagga atttggtgtt tgcgggatc gtcggcggat gtctcttcgg      180
gacccggcat cgcagccgta gtcggctgtt ctgttttcat gattttcctc tgcgcgtatc     240
tcatccgtta ccgggaattc ttcaaagact ccgtaatcga cctccttacc tgccgatggg     300
ttcgctactg cagctgcagc tgtaagtgca gctgcaaatg catctcgggc ccctgtagcc     360
gctgctgttc agcgtgttac aaggagacga tgatttacga catggtccaa tacggtcatc     420
gacggcgtcc cggacacggc gacgatcccg acagggtgat ctgcgagata gtcgagagtc     480
ccccggtttc ggcgccgacg tgtccgtcc cccgccgtc ggaggagtcc caccagcccg       540
tcatcccacc gcagccgcca gcaccgacat cggaacccaa accgaagaaa ggtagggcga     600
aagataaacc gaagggtaga ccgaaagaca aacctccgtg cgaaccgacg gtgagttcac     660
aaccaccgtc gcagccgacg gcaatgcccg gcggtccgcc cgacgcgcct cccccgcca     720
tgccgcagat gccacccggc gtggccgagg cggtacaagc tgccgtgcag gcggccgtgg     780
ccgcggctct acaacaacag cagcagcatc agaccggaac gtaacccgcc cccggtgcga    840
taaggaattt tccgacttgg cgcacatctc cttcctcaat gtttggacaa taaacacatt    900
ccttgccaaa aaatgacgtt tccagaaatc caaggcataa atgtccgtac accggccctt    960
cccaacacgg agtttgagat tccaagcagg agagaagatc atggtgtgga tatggctcgg   1020
catcgggctc ctcggcggta ccggactggc ttccctggtc ctggccattt ccttatttac   1080
ccagcgccga ggccgcaagc gatccgacga gacttcgtcg cgaggccggc tcccgggtgc   1140
tgcttctgat aagcgtggtg cctgcgcgtg ctgctatcga aatccgaaag aagacgtcgt   1200
cgagccgctg gatctggaac tgggctcat gcgggtggac acccaccgc cgacgccgca    1260
ggtgccgcgg tgtacgtcgc tctacatagg agaggatggt ctgccgatag ataaacccga   1320
gtttcctccg gcgcggttcg agatccccga cgtatccacg ccgggaacgc cgaccagcat   1380
cggccgatct ccgtcgcatt gctcctcgtc gagctctttg tcgtcctcga ccagcgtcga   1440
cacggtgctg tatcagccgc cgccatcctg gaagccacct ccgccgcccg ggcgcaagaa   1500
gcggccgcct acgccgccgg tccgggcccc caccacgcgg ctgtcgtcgc acagaccccc   1560
gacgccgata cccgcgccgc gtaagaacct gagcacgccg cccaccaaga aaacgccgcc   1620
gcccacgaaa cccaagccgg tcggctggac accgccggtg acacccaggc ccttcccgaa   1680
aacgccgacg ccacaaaagc cgccgcggaa tccgagacta ccgcgcaccg tcggtctgga   1740
gaatctctcg aaggtgggac tctcgtgtcc ctgtccccga cccgcacgc cgacggagcc    1800
gaccacgctg cctatcgtgt cggtttccga gctagccccg cctcctcgat ggtcggacat   1860
cgaggaactc ttggaacagg cggtgcagag cgtcatgaag gacgccgagt cgatgcagat   1920
gacctgagac cgaaagagcg agcgcgtccg ttgtacagtt gtatagcagc acacgccttc   1980
cctcttttc accgcagcta agagagaaa agagagtatg tcagtcaagg gcgtggagat     2040
gccagaaatg acgtgggact tggacgttag aaataaatgg cggcgtcgaa aggccctgag   2100
tcgcattcac cggttctggg aatgtcggct acgggtgtgg tggctgagtg acgccggcgt   2160
aagagaaacc gacccaccgc gtccccgacg ccgcccgact tggatgaccg cggtgtttca   2220
cgttatctgt gccgttttgc ttacgcttat gattatggcc atcggcgcgc tcatcgcgta   2280
cttaagatat taccaccagg acagttggcg agacatgctc cacgatctat tttgcggctg   2340
```

-continued

```
tcattatccc gagaagtgcc gtcggcacca cgagcggcag agaaggagac ggcaagccat   2400
ggatgtgccc gacccggaac tcggcgaccc ggcccgccgg ccgttgaacg gagctatgta   2460
ctacggcagc ggctgtcgct tcgacacggt ggaaatggtg gacgagacga gacccgcgcc   2520
gccggcgctg tcatcgcccg aaaccggcga cgatagcaac gacgacgcgg ttgccggcgg   2580
aggtgctggc ggggtaacat cacccgcgac tcgtacgacg tcgccgaacg cactgctgcc   2640
agaatggatg gatgcggtgc atgtggcggt ccaagccgcc gttcaagcga ccgtgcaagt   2700
aagtggcccg cgggagaacg ccgtatctcc cgctacgtaa gagggttgag ggggccgttc   2760
ccgcgcgagt gctgtacaaa agagagagac tgggacgtag atccggacag aggacggtca   2820
ccatggacga tctgccgctg aatgtcgggt tacccatcat cggcgtgatg ctcgtgctga   2880
tcgtggccat cctctgctat ctggcttacc actggcacga caccttcaaa ctggtgcgca   2940
tgtttctgag ctaccgctgg ctgatccgct gttgcgagct gtacggggag tacgagcgcc   3000
ggttcgcgga cctgtcgtct ctgggcctcg gcgccgtacg gcgggagtcg acagacgat   3060 accgtttctc cgaacggccc gacgagatct tggtccgttg ggaggaagtg tcttcccagt   3120
gcagctacgg gtcgtcgcgg ataacagacc gccgtgtggg ttcatcgtct tcgtcgtcgg   3180
tccacgtcgc tagccagaga acagcgtgc ctccgccgga catggcggtg acggcgccgc   3240
tgaccgacgt cgatctgttg aaacccgtga cgggatccgc gacgcagttc accaccgtag   3300
ccatggtaca ttatcatcaa gagtacacgt gaatgagaaa agaaaaaag aggggagcgg   3360 atcgcgataa tgtcgctttg acattctctg ctcgatctac tcagcgtctg cacgaaacgg   3420
catccgcacg gaggcgagcc caagcgtatc tgcagcaagc ggttctttcc ctcggtgatg   3480
gtggcagcat cggtggcggg agcttgttcg gacgatggac ggtgaggagt ccctggcgat   3540
caggcggctc ccgggtgtgg agttcaacgg gtggtaatgg tggcggtgat cggtgttaga   3600
aaacggtggc cctggcaaac atatatctac tgtaaaccct ctgctctgtt aataaaaagc   3660 acactttca catgagttcg taattttatt gtgtagtgga aattttacg tcattgggaa   3720 accccagaat gaaagagtat aatgtgcata tcaccggggg ttccctgtca gtacgaatgt   3780
acacaacgcg ggttacatta cgataaactt tccggtaaaa cgatgccgat acagcgtgta   3840
taacgctgat tgttacgaca aacgagttgg tatatccatt atatagtaac gaacatgctg   3900
tggatattag ttttatttgc actcgccgca tcggcgagtg aaaccactac aggtaccagc   3960
tctaattcca gtcaatctac tagtgctacc gccaacacga ccgtatcgac atgtattaat   4020
gcctctaacg gcagtagctg gacagtacca cagctcgcgc tgcttgccgc tagcggctgg   4080
acattatctg gactccttct cttatttacc tgctgctttt gctgcttttg gctagtacgt   4140
aaaatctgca gctgctgcgg caactcctcc gagtcagaga gcaaaacaac ccacgcgtac   4200
accaatgccg cattcacttc ttccgacgca acgttaccca tgggcactac agggtcgtac   4260 actccccac aggacggctc atttccacct ccgcctcggt gacgtaggct aaaccgaaac   4320
ccacgttgaa cctaacgcgg tttcggaagg cctgagacgt cactttcaca atgacgtccg   4380
tatacacgtt catcataaaa caccgtagag gctaaggctt cggtagggag agacctcaac   4440
tgttcctgat gagcacccgt gctctcatct cttcagactt gtcatgaccc ccgctcagac   4500
taacgcgact accaccgtgc acccgcacga cgcaaaaaac ggcagcggcg gtagtgccct   4560
gccgaccctc gtcgttttcg gctttatcgt tacgctactt ttctttctct ttatgctcta   4620
cttttggaac aacgacgtgt tccgtaagct gctccgtgcg cttggatcca gcgctgttgc   4680
gaccgcttcg acgcgtggca agacgaggtc atctaccgtc gtccatcacg tcgttcccag   4740
```

-continued

```
agcgacgacg agagtcgtac taacagcgtg tcatcgtacg ttcttttatc acccgcgtcc    4800
gatggcggtt ttgacaaccc ggcactgaca gaggccgtcg acagcgtgga cgactgggcg    4860
accacctcgg ttttctacgc cacgtccgac gaaacggcgg acgccgagcg ccgagactcg    4920
cagcaactgc tcatcgagct tccgccggag ccgctcccgc ccgacgtggt ggcggccatg    4980
cagaaagcag tgaaacgcgc tgtacagaac gcactacgac acagccacga ctcttggcag    5040
cttcatcaga ccctgtgacg ccagatgaac gttccttctt aaacatccga ggtagcaatg    5100
agacaggtcg cgtaccgccg gcgacgcgag agttcctgcg cggtgctggt ccaccacgtc    5160
ggccgcgacg gcgacggcga gggggaggca gcaaaaaaga cctgcaaaaa aaccggacgc    5220
tcagttgcgg gcatcccggg cgagaagctg cgtcgcacgg tggtcaccac cacgccggcc    5280
cgacgtttga gcggccgaca cacggagcag gagcaggcgg gcatgcgtct ctgtgaaaaa    5340
gggaagaaaa gaatcatcat gtgccgccgg gagtcgctcc gaactctgcc gtggctgttc    5400
tgggtgctgt tgagctgccc gcgactcctc gaatattctt cctcttcgtt cccttcgcc    5460
accgctgaca ttgccgaaaa gatgtgggcc gagaattatg agaccacgtc gccggcgccg    5520
gtgttggtcg ccgagggaga gcaagttacc atccctgca cggtcatgac acactcctgg    5580
cccatggtct ccattcgcgc acgtttctgt cgttcccacg acggcagcga cgagctcatc    5640
ctggacgccg tcaaaggcca tcggctgatg aacggactcc agtaccgcct gccgtacgcc    5700
acttggaatt tctcgcaatt gcatctcggc caaatattct cgcttacttt taacgtatcg    5760
atggacacag ccggcatgta cgaatgcgtg ctacgcaact acagccacgg cctcatcatg    5820
caacgcttcg taattctcac gcagctggag acgctcagcc ggcccgacga accttgctgc    5880
acaccggcgt taggtcgcta ctcgctggga gaccagatct ggtcgccgac gccctggcgt    5940
ctacggaatc acgactgcgg aacgtaccgc ggctttcaac gcaactactt ctatatcggc    6000
cgcgccgacg ccgaggattg ctggaaaccc gcatgtccgg acgaggaacc cgaccgctgt    6060
tggacagtga tacagcgtta ccggctcccc ggcgactgct accgttcgca gccacacccg    6120
ccgaaatttt taccggtgac gccagcaccg ccggccgaca tagacaccgg gatgtctccc    6180
tgggccactc ggggaatcgc ggcgttttg gggttttgga gtattttac cgtatgtttc    6240
ctatgctacc tgtgttatct gcagtgttgt ggacgctggt gtcccacgcc gggaagggga    6300
cgacgaggcg gtgagggcta tcgacgccta ccgacttacg atagttaccc cggtgttaga    6360
aagatgaaga ggtgagaaca cgtataaaat aaaaaaataa tatgttaaaa aatgcagtgt    6420
gtgaagtgtg aatagtgtga ttaaaatatg cggattgaat gggtgtggtg gttattcgga    6480
tactttgtgt catccgttgg gagcgaacgg tcattatcct atcgttacca cttggaatct    6540
aattcatcta ccaacgtggt ttgcaacgga acatttccg tgtttgtaaa cggcaccta    6600
ggtgtgcggt ataacattac ggtaggaatc agttcgtctt tattaatagg acaccttact    6660
atacaagtat tggaatcatg gttcacaccc tgggtccaaa ataaaagtta caacaaacaa    6720
cccctaggtg acactgaaac gctttataat atagatagcg aaaacattca tcgcgtatct    6780
caatattttc acacaagatg gataaaatct ctgcaagaga atcacacttg cgacctcaca    6840
aacagtacac ctacctatac atatcaagta aacgtgaaca cacgaattta cctaacacta    6900
acatcctcgg gatggcaaga ccgtctaaat tacaccgtca taaatagtac acactttaac    6960
ctcacagaat cgaacataac cagcattcaa aaatatctca acactacctg catagaaaga    7020
ctccgtaact acaccttgga gtccgtatac accacaactg tgcctcaaaa cataacaaca    7080
```

-continued

```
tctcaacacg caacaaccac tatgcacaca atacctccaa atacaataac aattcaaaat   7140
acaactcaaa gccatactgt acagacgccg tcttttaacg acacacataa cgtgacgaaa   7200
cacacgttaa acataagcta cgttttatca caaaaaacga ataacacaac atcaccgtgg   7260
atatatgcca tacctatggg cgctacagcc acaataggcg ccggtttata tatcgggaaa   7320
cactttacgc cggttaagtt cgtatacgag gtatggcgcg gtcagtaaag acgattcgga   7380
ttcaacacat atactcccca cgatcctcga acaccttaca gcatatgagc aaaaaacaag   7440
aaagtatagc cacaatcaca tttgggcgaa taacatgctg tcatccacta gcgtctatta   7500
atctaatgtt taacgggagc tgtactgtca ccgttaaaat atccatggga atcaacgggt   7560
caaccaacgt ccatcagctt gtgattgtgc tccatctggg taaccgctgt cagccttggc   7620
gacaggtgta atcacagctg tcacataact cacgaagcct ccaatcacag cagcacacat   7680
agtcctaacg ccattggcgt gtataaaagt tcggaaaact tgacggttgt acggcacgac   7740
aaatcgatgt agtggtatgt ttttccagca gagaccgtgt gcggtctctt aggttcgcta   7800
tactgtggct ggaaactggt tacctgtgaa gatggctaac tatcctgttc tgtcctggaa   7860
aaacttttgg cgtcgtaggt ggactttgca gtatgcgggt tagtgaagtt atgtcattta   7920
tttacgttta cgatctcgta ttacaaaccg cggagaggat gataccgttc ggccccatga   7980
gttattttta ttcttccggt aggaggcatg aagcctctga taatgctcat ctgctttgct   8040
gtgatattat tgcagcttgg agtgactaaa gtgtgtcagc ataatgaagt gcaactgggc   8100
aatgagtgct gccctccgtg tggttcggga caaagagtta ctaaagtatg cacggattat   8160
accagtgtaa cgtgtacccc ttgccccaac ggcacgtatg tatcgggact ttacaactgt   8220
accgattgca ctcaatgtaa cgtcactcag gtcatgattc gtaactgcac ttccaccaat   8280
aataccgtat gcgcacctaa gaaccatacg tacttttcca ctccaggcgt ccaacatcac   8340
aaacaacgac agcaaaatca taccgcacat ataaccgtca aacaaggaaa aagcggtcgt   8400
catactctag cctggttgtc tctctttatc tttcttgtgg gtatcatact tttaattctc   8460
tatcttatag ccgcctatcg gagtgagaga tgccaacagt gttgctcaat cggcaaaatt   8520
ttctaccgca ccctgtaagc ttcctgttgt tgtttttaca tcacgtacg atgaagtcac    8580 acagataatt acagatgagc tgttcatatt ttttattatt ttttccaatt cctgcactaa   8640 aaaagaagc actttacgga accgtgtctg agtatctgtg gggaatttag gtacttttg     8700 ccgacgtcag gaaaaataag tgtcgcctac ataagagccc ggtgctatcg tgctgtcact   8760 cttcttgtt gccttcgatg tacggcgtcc tggctcatta ctactccttc atcagtagcc   8820
ccagcgttat ggttaatttt aagcatcata acgccgtgca gctgttatgt gcacggaccc   8880
gagacgcact gccggatggg aacgtttaac ccatcatgcg tcgtatcacg cgaactacgg   8940
ggcatacgcc gtgttgatgg ctacatcgca aagaaagtcc ctagtgttac atcgatacag   9000
tgccgtgaca gccgtggccc tgcagctcat gcctgttgag atcgtccgca agctagatca   9060
gtcggactgg gtgcgggggtg cctggatcgt gtcagagact tttccaacta gcgaccccaa   9120
aggagtttgg agcgacgatg actcctcgat gggtggaagt gatgattgat gatgagaacc   9180
tgacaagaaa gacgagagag aaatttagag ctgtcattgt agaattagtc tagattcctg   9240
ataataaaca gtatcgattt tgaaacctaa ttgacgtgtg atcgattttt aaacctctgt   9300
gttgtgtgat tgattggtat gtgggggggat ccgatttcaa agggggtac ttatcgggaa    9360 ttgatgtgtc atggacgcag ttttgagcga ttttccggga ataccggata ttcgaatta    9420 ctggtagtga cgtagataat aaaattataa tgcgattaat ttttggtgcg ttgattattt   9480
```

-continued

```
ttttagcata tgtgtatcat tatgaggtga atggaacaga attacgctgc agatgtcttc    9540
atagaaaatg gccgcctaat aaaattatat tgggtaatta ttggcttcat cgcgatccca    9600
gagggcccgg atgcgataaa aatgaacatt tattgtatcc agacggaagg aaaccgcctg    9660
gacctggagt atgtttatcg cccgatcacc tcttctcaaa atggttagac aaacacaacg    9720
ataataggtg gtataatgtt aacataacga aatcaccagg accgagacga ataaatataa    9780
ccttgatagg tgttagagga taatatttaa tgtatgtttt caaacagaca agttcgttaa    9840
aacaaaatat tacagtatgt gtttaatatg gtgctaacat ggttgcacca tccggtttca    9900
aactcgcata tcaatctgtt atcggtacga cacctgtcat taatcgcata tatgttactt    9960
accatatgtc ccctagccgt ccatgtttta gaactagaag attacgacag gcgctgccgt    10020
tgcaacaacc aaattctgtt gaatacctg ccggtcggaa ccgaattgct taagccaatc    10080
gcagcgagcg aaagctgcaa tcgtcaggaa gtgctggcta ttttaaagga caagggaacc    10140
aagtgtctca atcctaacgc gcaagccgtg cgtcgtcaca tcaaccggct attttttcgg    10200
ttaatcttag acgaggaaca acgcatttac gacgtagtgt ctaccaatat tgagttcggt    10260
gcctggccag tccctacggc ctacaaagcc tttctttgga aatacgccaa gagactgaac    10320
taccaccact tcagactgcg ctggtgatca tgtccctatt ttaccgtgcg gtagctctgg    10380
gcacgctaag cgctttggtg tggtacagca ctagcatcct cgcagagatt aacgaaaatt    10440
cctgctcctc atcttctgcg gatcacgaag actgcgagga accggacgag atcgttcgcg    10500
aagagcaaga ctatcgggct ctgctggcct ttttcctagt gatttgcggt acgctcctcg    10560
tcacttgtgt gatctgagac gtcatgctgg tagcgtttat gagtcgggcg gtggccgaca    10620
cgccgcattt cctaacccgc gcagcatgtt gcgcttgctg ttcacgctcg tcctgctggc    10680
cctccacggg cagtctgtcg gcgctagccg cgactatgtg catgttcggc tactgagcta    10740
ccgaggcgac cccctggtct tcaagcacac tttctcgggt gtgcgtcgac ccttcaccga    10800
gctaggctgg gctgcgtgtc gcgactggga cagtatgcat tgcacaccct tctggtctac    10860
cgatctggag cagatgaccg actcggtgcg gcgttacagc acggtgagcc ccggcaagga    10920
agtgacgctt cagcttcacg ggaaccaaac cgtacagccg tcgtttctaa gctttacgtg    10980
ccgcctgcag ctagaacccg tggtggaaaa tgttggcctc tacgtggcct acgtggtcaa    11040
cgacggcgaa cgcccacaac agttttttac accgcaggta gacgtggtac gctttgctct    11100
atatctagaa acactctccc ggatcgtgga accgttagaa tcaggtcgcc tggcagtgga    11160
atttgatacg cctgacctag ctctggcgcc cgatttagta agcagcctct tcgtggccgg    11220
acacggcgag accgactttt acatgaactg gacgctgcgt cgcagtcaga cccactacct    11280
ggaggagatg gccttacagg tggagattct aaaacccgc ggcgtacgtc accgcgctat    11340
tatccaccat ccgaagctac agccgggcgt tggcctgtgg atagatttct gcgtgtaccg    11400
ctacaacgcg cgcctgaccc gcggctacgt acgatacacc ctgtcaccga aagcgcgctt    11460
gcccgcaaaa gcagagggtt ggctggtgtc actagacaga ttcatcgtgc agtacctcaa    11520
cacattgctg attacaatga tggcggcgat atgggctcgc gttttgataa cctacctggt    11580
gtcgcggcgt cggtagaggc ttgcggaaac cacgtcctcg tcacacgtcg ttcgcggaca    11640
tagcaagaaa tccacgtcgc cacatctcga gaatgccggc cttgcggggt ccccttcgcg    11700
caacattcct ggccctggtc gcgttcgggt tgctgcttca gatagacctc agcgacgcta    11760
cgaatgtgac cagcagcaca aaagtcccta ctagcaccag caacagaaat aacgtcgaca    11820
```

```
acgccacgag tagcggaccc acaaccggga tcaacatgac caccacccac gagtcttccg   11880
ttcacaacgt gcgcaataac gagatcatga aagtgctggc tatcctcttc tacatcgtga   11940
caggcacctc cattttcagc ttcatagcgg tactgatcgc ggtagtttac tcctcgtgtt   12000
gcaagcaccc gggccgcttt cgtttcgccg acgaagaggc cgtcaacctg ttggacgaca   12060
cggacgacag tggcggcagc agcccgtttg gcagcggttc ccgacgaggt tctcagatcc   12120
ccgccggatt ttgttcctcg agcccttatc agcggttgga aactcgggac tgggacgagg   12180
aggaggaggc gtccgcggcc cgcgagcgca tgaaacatga tcctgagaac gtcatctatt   12240
tcagaaagga tggcaacttg gacacgtcgt tcgtgaatcc caattatggg agaggctcgc   12300
ctttgaccat cgaatctcac ctctcggaca atgaggagga ccccatcagg tactacgttt   12360
cggtgtacga tgaactgacc gcctcggaaa tggaagaacc ttcgaacagc accagctggc   12420
agattcccaa actaatgaaa gttgccatgc aacccgtctc gctcagagat cccgagtacg   12480
actaggcttt ttttttttgtc tttcggttcc aactcttttcc ccgccccatc acctcgcctg   12540
tactatgtgt atgatgtctc ataataaagc tttctttctc agtctgcaac atgcagctgt   12600
gtcgggtgtg gctgtctgtt tgtctgtgcg ccgtggtgct gggtcagtgc cagcgggaaa   12660
ccgcggaaaa aaacgattat taccgagtac cgcattactg ggacgcgtgc tctcgcgcgc   12720
tgcccgacca aacccgttac aagtatgtgg aacagctcgt ggacctcacg ttgaactacc   12780
actacgatgc gagccacggc ttggacaact ttgacgtgct caagaggtga gggtacgcgc   12840
taaaggtgca tgcaacgggaagg taagggg cgaacgggta acggctaagt aaccgcatgg   12900
ggtatgaaat gacgtttgga acctgtgctt gcagaatcaa cgtgaccgag gtgtcgttgc   12960
tcatcagcga ctttagacgt cagaaccgtc gcggcggcac caacaaaagg accacgttca   13020
acgccgccgg ttcgctggcg ccacacgccc ggagcctcga gttcagcgtg cggctctttg   13080
ccaactagcc tgcgtcacgg gaaataatat gctgcggctt ctgcttcgtc accactttca   13140
ctgcctgctt ctgtgcgcgg tttgggcaac gccctgtctg gcgtctccgt ggtcgacgct   13200
aacggcaaac cagaatccgt ccccgccatg gtctaaactg acgtattcca aaccgcatga   13260
cgcggcgacg ttttactgtc cttttctcta tccctcgccc ccacggtccc ccttgcaatt   13320
ctcgggttc cagcaggtat caacgggtcc cgagtgtcgc aacgagaccc tgtatctgct   13380
gtacaaccgg gaaggccaga ccttggtgga gagaagctcc acctgggtga aaaaggtgat   13440
ctggtatctg agcggtcgca accagaccat cctccaacgg atgccccaaa cggcttcgaa   13500
accgagcgac ggaaacgtgc agatcagcgt ggaagacgcc aagattttg gagcgcacat   13560
ggtgcccaag cagaccaagc tgctacgctt cgtcgtcaac gatggcacgc gttatcagat   13620
gtgtgtgatg aagctggaga gctgggccca cgtcttccgg gactacagcg tgtcttttca   13680
ggtgcgattg acgttcaccg aggccaataa ccagacttac accttctgta cccatcccaa   13740
tctcatcatt tgagcccgtc gcgcgcgcag ggaattttga aaaccgcgcg tcatgagtcc   13800
caaagacctg acgccgttct tgacgacgtt gtggctgcta ttgggtcaca gccgcgtgcc   13860
gcgggtgcgc gcagaagaat gttgcgaatt cataaacgtc aaccaccgc cggaacgctg   13920
ttacgatttc aaaatgtgca atcgcttcac cgtcgcgtac gtattttcat gattgtctgc   13980
gttctgtggt gcgtctggat ttgtctctcg acgtttctga tagccatgtt ccatcgacga   14040
tcctcgggaa tgccagagta gattttcatg aatccacagg ctgcggtgtc cggacggcga   14100
agtctgctac agtcccgaga aaacggctga gattcgcggg atcgtcacca ccatgaccca   14160
ttcattgaca cgccaggtcg tacacaacaa actgacgagc tgcaactaca atccgtaagt   14220
```

```
ctcttcctcg agggccttac agcctatggg agagtaagac agagagggac aaaacatcat    14280
taaaaaaaaa agtctaattt cacgttttgt accccccttc ccctccgtgt tgtagcccat    14340
cggccgcggc gatctcctag taacactcgt ccgacacttc caccatctcc agctcggccg    14400
gcggttcggc atcctctacc agcggcgtcg tctcatcttt gccgcagcag cggacgcaca    14460
ccttctccag gcagaacgcc accagctgcc gccgaacgta ccacaggtac acgtgcagac    14520
ctgcgaacag gactacggag gtcatgacca ccacgacgca cacgggaatc cagggatcga    14580
gattgttgct ggaactcatg gctatcgcca ccgacgtgcc cgcgtctgtc tcaccgccgc    14640
tcgcccgatg tcgcgcggct tgttatacgc tagcccgtcg ccgcctcggg gcacggtgcc    14700
ctcctaccca cgtaacttcc tccgtgactt aaagtcgcgt gtggtagatc tcctgctccg    14760
tggacgaacc gtccggcagg atagcggtta aggattcggt gctaaggccg tgtcgccaac    14820
gtcgaatgct acgttgcaac agcttcgacg gacggccatc ccctctctca tcgcaataat    14880
aaaacaccag cagcgcgcac gacgcgatca cggtgacacc catgattaga cccacgcaga    14940
tagccagccc cgctagcgta tctagcgcca tcccgttcgc tcccgttgtc tcctgagcga    15000
agcaacttct cggtccccgt tttcaacagt ttttgtttcc ttctccgcga ctagatgtta    15060
acgcccgcgg tctttccggc cgtgctctac ctcctggcgc ttgtcgtctg ggttgagatg    15120
ttctgcctcg tcgccgtagc cgtcgtcgag cgcgagatcg cctgggcgct gctgctgcgg    15180
atgctggtcg ttggcctgat ggtggaagtc ggcgccgccg ccgcttggac cttcgtgcgt    15240
tgtcttgcct atcagcgctc cttccccgtg cttacggcct tccctgaaa cccacgttaa    15300
ccgaccgtcc caaaaacgcc ggtgttaaca caggaaaaaa agaaaccacg caggaaccgc    15360
gcaggaacca cgcggaacat gggacactat ctggaaatcc tgttcaacgt catcgtcttc    15420
actctgctgc tcggcgtcat ggtcagtatc gtcgcttggt acttcacgtg aaccaccgtc    15480
gtcccggttt aaaaaccatc atcgacggcc gttataaagc cacccggaca cgcgccgcgg    15540
cacttgccta cggcgctgct tcagggaaac tcctcttcct tctgctcttc ctccttcacc    15600
gcagggatcg tttccctcga ccaggga ctc gccgaagcaa ccgccggagc aacctggagg    15660
agtcgcggca tgacggcgcc caagtgtgtc accaccagta cttatctggt caagaccaag    15720
gaacagccct ggtggcccga caacgccatc aggagatggt ggatcagtgt tgctatcgtc    15780
atcttcatcg gagtctgtct ggtggccctg atgtacttta cgcagcagca ggcacgcagc    15840
gggagcagca gcggctagac aagtctctgg cggctacagc tccaagcgcc gtagccgggc    15900
cgcctgccga tcgcgacgtc gtggaccatc gaacagagac tcacgcgtac gagaccccga    15960
ggtacgccac gcggtgccta acgcggtata ccacacccgt acggtctgca gtgcggcgta    16020
caacgtgtgg aaaacgcgtt gcgtcgcaga gtccgccacg ttcctgtctt gtcgctcccc    16080
aatcgtctcc cgcacacccc ccgcgacacc cagagggcgg gtgagccaag tattcttaag    16140
gccgttcttt gttccatagc ccataaattg ttgattccgg agctcgttgg cgcggaaata    16200
gccggataag gggagcaaca accgttggcg aaagccgtcc cgctcattca gtccgggttt    16260
cgcgtccagt cggacgtgtg accgttgggc aacggaacgg cgtttcactg ccaaaatcgt    16320
atcgggtagt gtacgagacg tcggcggtgc agaatgcgac tcgcggcgta gctcgccgtc    16380
gctatgcggc tcgtcgccgt gtggcgcggc ctggccggct gtctgcgtcc agatctgttg    16440
gccttttggt tcctctggct gctgctgcgt gtgtgctttg gtagacgcgg tggcagtttg    16500
cggtctgcgg taagtgagga tgtcgccgag caaacgcact tgcggcgcgt gggcggcacg    16560
```

-continued

```
cgtgtcattg taggttcgtt gccagatggc aagtgctgtc aacagcaggc gttgtgggcg      16620
gtcggtgtat ttttgtgggt tgcggtgaga gtcggcactc ggtgttttgt gagtcatctc      16680
aactatctgt gttgctttga gcagcgtcca gaacagcgac gcgactttgg ggatggcctc      16740
gtgctcacct ccgcggagag cgccgccgga cctgctcgtc agcagcgagc tacgcagacg      16800
gaatatctgg aggagagtta cgtgtgtcac aggagagcgc gggtctccgg cggtaacgac      16860
ggcggtgtcg tcgacacgtg tgcggcctgt tgtgctctgc ggaaaagtgc cggtctcgga      16920
gaccgtggac gaaaaagaga acgcagcagc taccgctggc ggcggcggcg cggtctcgga      16980
cgttgatgtt cgacgttgtg agcactcgga acagcggtg aggcagaagg tcgattctcc      17040
agggaacgac agtcgatgcg tggtagccgc agcaggtgag gttggggcgg acaacgtgtt      17100
gcggattgtg gcgagaacgt cgtcctcccc ttcttcaccg ccccacccac cctcggttgg      17160
tgtttctttt tcttgtgtc ctgcagatag ttccacggac agcgacggca agtccataat       17220
cagcggtgtg caagtggtgg aacacgacga agatatcatc gcgccgcaga gtttgtggtg      17280
cacggcgttc aaggaagccc tctgggatgt ggctctgttg gaagtgccgc gttgggcgtg      17340
gcagggctgg aagaggtggc gcaacagcga ggccgggcgt cgatggagtg ctgggtctgc      17400
gtcggcttcc agcttgtctg acttggcggg cgaggccgtt ggagaattgg tgggatcggt      17460
cgtcgcgtac gtgatccttg aacgtctgtg gttggcagcc agaggttggg tgtgcgaaac      17520
aggtgtggaa gccgaggagg ccatgtcgcg gcggcgacag cgcatgctgt ggcgtattgt      17580
tctctcgtgg aggcgacggc gaatgcagca gacggtgttc gatggagatg gcgtgcgggg      17640
aagaaagcgc cgtgttgtga gcagacgacg taggatgcgg gacgtcggag cacatgggcc      17700
atgtgtggtg gcagatggcg gtgtccgctg tgtctgctg cggcagtgca tagacgaagc       17760
aacatgtcgc tgtgaagaga tagagtgtga gcatagctgc atgcagcgtt gcgtgtataa      17820
gcggggggga ttaagacgtt aataaagaat agcggcggtt ctgataggc gaccgctgaa       17880 gtgagctgcg tgtgcgtgtg gtttgtggag tccccgccgc ccccggtccc gtgtccgccg      17940
gcaaagcccc ccggntccgc acactcctgg ccgcgcaacc ctcgtcgctg caaaagcccc      18000
ccgtccccgc acaccccgc gaccgccggt cccgcgagtc cccgtccccg ccgcaaaagg       18060 ccccgtcct cgccgcaaac accccgtca ccccgtccc tcagnccggg tccgcgagtc         18120
cccgttccca gcgtaatccc cgtacccgca acgncccggn cccaccgtcg tcccgcacac      18180 ccccgtccc ccagcccggt gcccagcgtg cgaaaaaagc tccgtccctc acacccgcag       18240
aaagatccct cagcgcggtg aaaccccgtc cccagcgccg tgccgctgac aaagaccatg      18300
ggacgacacg cacaggca                                                    18318
```

<210> SEQ ID NO 2
<211> LENGTH: 214
<212> TYPE: PRT
<213> ORGANISM: Human cytomegalovirus

<400> SEQUENCE: 2

```
Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
        50                  55                  60
```

-continued

Pro Arg Ser Pro Leu Gln Phe Ser Gly Phe Gln Gln Val Ser Thr Gly
 65                  70                  75                  80

Pro Glu Cys Arg Asn Glu Thr Leu Tyr Leu Leu Tyr Asn Arg Glu Gly
                 85                  90                  95

Gln Thr Leu Val Glu Arg Ser Ser Thr Trp Val Lys Lys Val Ile Trp
                100                 105                 110

Tyr Leu Ser Gly Arg Asn Gln Thr Ile Leu Gln Arg Met Pro Gln Thr
                115                 120                 125

Ala Ser Lys Pro Ser Asp Gly Asn Val Gln Ile Ser Val Glu Asp Ala
            130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
                180                 185                 190

Arg Leu Thr Phe Thr Glu Ala Asn Asn Gln Thr Tyr Thr Phe Cys Thr
                195                 200                 205

His Pro Asn Leu Ile Ile
                210

<210> SEQ ID NO 3
<211> LENGTH: 179
<212> TYPE: PRT
<213> ORGANISM: Human cytomegalovirus

<400> SEQUENCE: 3

Met Pro Ala Leu Arg Gly Pro Leu Arg Ala Thr Phe Leu Ala Leu Val
  1               5                  10                  15

Ala Phe Gly Leu Leu Leu Gln Ile Asp Leu Ser Asp Ala Thr Asn Val
                 20                  25                  30

Thr Ser Ser Thr Lys Val Pro Thr Ser Thr Ser Asn Arg Asn Asn Val
                 35                  40                  45

Asp Asn Ala Thr Ser Ser Gly Pro Thr Thr Gly Ile Asn Met Thr Thr
 50                  55                  60

Thr His Glu Ser Ser Val His Asn Val Arg Asn Asn Glu Ile Met Lys
 65                  70                  75                  80

Val Leu Ala Ile Leu Phe Tyr Ile Val Thr Gly Thr Ser Ile Phe Ser
                 85                  90                  95

Phe Ile Ala Val Leu Ile Ala Val Val Tyr Ser Ser Cys Cys Lys His
                100                 105                 110

Pro Gly Arg Phe Arg Phe Ala Asp Glu Glu Ala Val Asn Leu Leu Asp
            115                 120                 125

Asp Thr Asp Asp Ser Gly Gly Ser Ser Pro Phe Gly Ser Gly Ser Arg
            130                 135                 140

Arg Gly Ser Gln Ile Pro Pro Asp Phe Val Pro Arg Ala Leu Ile Ser
145                 150                 155                 160

Gly Trp Lys Leu Gly Thr Gly Thr Arg Arg Arg Arg Pro Arg Pro
                165                 170                 175

Ala Ser Ala

<210> SEQ ID NO 4
<211> LENGTH: 20
<212> TYPE: PRT
<213> ORGANISM: Human cytomegalovirus -continued

```
<400> SEQUENCE: 4

Asn Met Ile Leu Arg Thr Ser Ser Ile Ser Glu Arg Met Ala Thr Trp
1               5                   10                  15

Thr Arg Arg Ser
            20

<210> SEQ ID NO 5
<211> LENGTH: 9
<212> TYPE: PRT
<213> ORGANISM: Human cytomegalovirus

<400> SEQUENCE: 5

Ile Pro Ile Met Gly Glu Ala Arg Leu
1               5

<210> SEQ ID NO 6
<211> LENGTH: 23
<212> TYPE: PRT
<213> ORGANISM: Human cytomegalovirus

<400> SEQUENCE: 6

Pro Ser Asn Leu Thr Ser Arg Thr Met Arg Arg Thr Pro Ser Gly Thr
1               5                   10                  15

Thr Phe Arg Cys Thr Met Asn
            20

<210> SEQ ID NO 7
<211> LENGTH: 18
<212> TYPE: PRT
<213> ORGANISM: Human cytomegalovirus

<400> SEQUENCE: 7

Pro Pro Arg Lys Trp Lys Asn Leu Arg Thr Ala Pro Ala Gly Arg Phe
1               5                   10                  15

Pro Asn

<210> SEQ ID NO 8
<211> LENGTH: 16
<212> TYPE: PRT
<213> ORGANISM: Human cytomegalovirus

<400> SEQUENCE: 8

Lys Leu Pro Cys Asn Pro Ser Arg Ser Glu Ile Pro Ser Thr Thr Arg
1               5                   10                  15

<210> SEQ ID NO 9
<211> LENGTH: 257
<212> TYPE: PRT
<213> ORGANISM: Human cytomegalovirus

<400> SEQUENCE: 9

Met Gly Cys Asp Val His Asp Pro Ser Trp Gln Cys Gln Trp Gly Val
1               5                   10                  15

Pro Thr Ile Ile Val Ala Trp Ile Thr Cys Ala Ala Leu Gly Ile Trp
                20                  25                  30

Cys Leu Ala Gly Ser Ser Ala Asp Val Ser Ser Gly Pro Gly Ile Ala
            35                  40                  45

Ala Val Val Gly Cys Ser Val Phe Met Ile Phe Leu Cys Ala Tyr Leu
        50                  55                  60

Ile Arg Tyr Arg Glu Phe Phe Lys Asp Ser Val Ile Asp Leu Leu Thr
```

```
                65                  70                  75                  80
            Cys Arg Trp Val Arg Tyr Cys Ser Cys Ser Cys Lys Cys Ser Cys Lys
                                85                  90                  95

Cys Ile Ser Gly Pro Cys Ser Arg Cys Cys Ser Ala Cys Tyr Lys Glu
                            100                 105                 110

Thr Met Ile Tyr Asp Met Val Gln Tyr Gly His Arg Arg Pro Gly
                        115                 120                 125

His Gly Asp Asp Pro Asp Arg Val Ile Cys Glu Ile Val Glu Ser Pro
                130                 135                 140

Pro Val Ser Ala Pro Thr Val Ser Val Pro Pro Ser Glu Glu Ser
            145                 150                 155                 160

His Gln Pro Val Ile Pro Pro Gln Pro Ala Pro Thr Ser Glu Pro
                            165                 170                 175

Lys Pro Lys Lys Gly Arg Ala Lys Asp Lys Pro Lys Gly Arg Pro Lys
                        180                 185                 190

Asp Lys Pro Pro Cys Glu Pro Thr Val Ser Ser Gln Pro Pro Ser Gln
                        195                 200                 205

Pro Thr Ala Met Pro Gly Gly Pro Pro Asp Ala Pro Pro Ala Met
            210                 215                 220

Pro Gln Met Pro Pro Gly Val Ala Glu Ala Val Gln Ala Ala Val Gln
            225                 230                 235                 240

Ala Ala Val Ala Ala Leu Gln Gln Gln Gln His Gln Thr Gly
                            245                 250                 255

Thr

<210> SEQ ID NO 10
<211> LENGTH: 175
<212> TYPE: PRT
<213> ORGANISM: Human cytomegalovirus

<400> SEQUENCE: 10

Met Ala Arg Thr Arg Glu Ala Ser Pro Val Pro Pro Arg Ser Pro Met
            1               5                   10                  15

Pro Ser His Ile His Thr Met Ile Phe Ser Pro Ala Trp Asn Leu Lys
                            20                  25                  30

Leu Arg Val Gly Lys Gly Arg Cys Thr Asp Ile Tyr Ala Leu Asp Phe
                        35                  40                  45

Trp Lys Arg His Phe Leu Ala Arg Asn Val Phe Ile Val Gln Thr Leu
                    50                  55                  60

Arg Lys Glu Met Cys Ala Lys Ser Glu Asn Ser Leu Ser His Arg Gly
            65                  70                  75                  80

Arg Val Thr Phe Arg Ser Asp Ala Ala Val Val Glu Pro Arg
                            85                  90                  95

Pro Arg Pro Ala Arg Gln Leu Val Pro Arg Pro Arg Arg Val
                        100                 105                 110

Ala Ser Ala Ala Trp Arg Gly Glu Ala Arg Arg Ala Asp Arg Arg Ala
                        115                 120                 125

Leu Pro Ser Ala Ala Thr Val Val Asn Ser Pro Ser Val Arg Thr
                130                 135                 140

Glu Val Cys Leu Ser Val Tyr Pro Ser Val Tyr Leu Ser Pro Tyr Leu
            145                 150                 155                 160

Ser Ser Val Trp Val Pro Met Ser Val Leu Ala Ala Val Gly
                            165                 170                 175
```

<210> SEQ ID NO 11
<211> LENGTH: 328
<212> TYPE: PRT
<213> ORGANISM: Human cytomegalovirus

<400> SEQUENCE: 11

```
Met Ser Val His Arg Pro Phe Pro Thr Arg Ser Leu Arg Phe Gln Ala
1               5                   10                  15

Gly Glu Lys Ile Met Val Trp Ile Trp Leu Gly Ile Gly Leu Leu Gly
            20                  25                  30

Gly Thr Gly Leu Ala Ser Leu Val Leu Ala Ile Ser Leu Phe Thr Gln
        35                  40                  45

Arg Arg Gly Arg Lys Arg Ser Asp Glu Thr Ser Ser Arg Gly Arg Leu
    50                  55                  60

Pro Gly Ala Ala Ser Asp Lys Arg Gly Ala Cys Ala Cys Cys Tyr Arg
65                  70                  75                  80

Asn Pro Lys Glu Asp Val Val Glu Pro Leu Asp Leu Glu Leu Gly Leu
                85                  90                  95

Met Arg Val Asp Thr His Pro Pro Thr Pro Gln Val Pro Arg Cys Thr
            100                 105                 110

Ser Leu Tyr Ile Gly Glu Asp Gly Leu Pro Ile Asp Lys Pro Glu Phe
        115                 120                 125

Pro Pro Ala Arg Phe Glu Ile Pro Asp Val Ser Thr Pro Gly Thr Pro
    130                 135                 140

Thr Ser Ile Gly Arg Ser Pro Ser His Cys Ser Ser Ser Ser Ser Leu
145                 150                 155                 160

Ser Ser Ser Thr Ser Val Asp Thr Val Leu Tyr Gln Pro Pro Pro Ser
                165                 170                 175

Trp Lys Pro Pro Pro Pro Gly Arg Lys Lys Arg Pro Pro Thr Pro
            180                 185                 190

Pro Val Arg Ala Pro Thr Thr Arg Leu Ser Ser His Arg Pro Pro Thr
        195                 200                 205

Pro Ile Pro Ala Pro Arg Lys Asn Leu Ser Thr Pro Pro Thr Lys Lys
    210                 215                 220

Thr Pro Pro Pro Thr Lys Pro Lys Pro Val Gly Trp Thr Pro Pro Val
225                 230                 235                 240

Thr Pro Arg Pro Phe Pro Lys Thr Pro Thr Pro Gln Lys Pro Pro Arg
                245                 250                 255

Asn Pro Arg Leu Pro Arg Thr Val Gly Leu Glu Asn Leu Ser Lys Val
            260                 265                 270

Gly Leu Ser Cys Pro Cys Pro Arg Pro Arg Thr Pro Thr Glu Pro Thr
        275                 280                 285

Thr Leu Pro Ile Val Ser Val Ser Glu Leu Ala Pro Pro Arg Trp
    290                 295                 300

Ser Asp Ile Glu Glu Leu Leu Glu Gln Ala Val Gln Ser Val Met Lys
305                 310                 315                 320

Asp Ala Glu Ser Met Gln Met Thr
                325
```

<210> SEQ ID NO 12
<211> LENGTH: 240
<212> TYPE: PRT
<213> ORGANISM: Human cytomegalovirus

<400> SEQUENCE: 12

Met Ser Val Lys Gly Val Glu Met Pro Glu Met Thr Trp Asp Leu Asp

```
             1               5              10              15
         Val Arg Asn Lys Trp Arg Arg Lys Ala Leu Ser Arg Ile His Arg
                         20              25              30

Phe Trp Glu Cys Arg Leu Arg Val Trp Trp Leu Ser Asp Ala Gly Val
                         35              40              45

Arg Glu Thr Asp Pro Pro Arg Pro Arg Arg Pro Thr Trp Met Thr
                 50              55              60

Ala Val Phe His Val Ile Cys Ala Val Leu Leu Thr Leu Met Ile Met
         65              70              75              80

Ala Ile Gly Ala Leu Ile Ala Tyr Leu Arg Tyr Tyr His Gln Asp Ser
                         85              90              95

Trp Arg Asp Met Leu His Asp Leu Phe Cys Gly Cys His Tyr Pro Glu
                         100             105             110

Lys Cys Arg Arg His His Glu Arg Gln Arg Arg Arg Gln Ala Met
                     115             120             125

Asp Val Pro Asp Pro Glu Leu Gly Asp Pro Ala Arg Arg Pro Leu Asn
                     130             135             140

Gly Ala Met Tyr Tyr Gly Ser Gly Cys Arg Phe Asp Thr Val Glu Met
         145                 150             155             160

Val Asp Glu Thr Arg Pro Ala Pro Pro Ala Leu Ser Ser Pro Glu Thr
                         165             170             175

Gly Asp Asp Ser Asn Asp Asp Ala Val Ala Gly Gly Ala Gly Gly
                     180             185             190

Val Thr Ser Pro Ala Thr Arg Thr Thr Ser Pro Asn Ala Leu Leu Pro
                     195             200             205

Glu Trp Met Asp Ala Val His Val Ala Val Gln Ala Ala Val Gln Ala
                     210             215             220

Thr Val Gln Val Ser Gly Pro Arg Glu Asn Ala Val Ser Pro Ala Thr
         225                 230             235             240

<210> SEQ ID NO 13
<211> LENGTH: 96
<212> TYPE: PRT
<213> ORGANISM: Human cytomegalovirus

<400> SEQUENCE: 13

Met Ala Thr Ile Ser Thr Ser Ile Thr Pro Met Met Gly Asn Pro Thr
         1               5              10              15

Phe Ser Gly Arg Ser Ser Met Val Thr Val Leu Cys Pro Asp Leu Arg
                         20              25              30

Pro Ser Leu Ser Leu Leu Tyr Ser Thr Arg Ala Gly Thr Ala Pro Ser
                         35              40              45

Thr Leu Leu Arg Ser Gly Arg Tyr Gly Val Leu Pro Arg Ala Thr Tyr
                     50              55              60

Leu His Gly Arg Leu Asn Gly Gly Leu Asp Arg His Met His Arg Ile
         65              70              75              80

His Pro Phe Trp Gln Gln Cys Val Arg Arg Arg Thr Ser Arg Gly
                         85              90              95

<210> SEQ ID NO 14
<211> LENGTH: 169
<212> TYPE: PRT
<213> ORGANISM: Human cytomegalovirus

<400> SEQUENCE: 14

Met Asp Asp Leu Pro Leu Asn Val Gly Leu Pro Ile Ile Gly Val Met
```

```
                1               5                    10                   15
Leu Val Leu Ile Val Ala Ile Leu Cys Tyr Leu Ala Tyr His Trp His
                    20                  25                  30

Asp Thr Phe Lys Leu Val Arg Met Phe Leu Ser Tyr Arg Trp Leu Ile
                    35                  40                  45

Arg Cys Cys Glu Leu Tyr Gly Glu Tyr Glu Arg Arg Phe Ala Asp Leu
                    50                  55                  60

Ser Ser Leu Gly Leu Gly Ala Val Arg Arg Glu Ser Asp Arg Arg Tyr
 65                     70                  75                  80

Arg Phe Ser Glu Arg Pro Asp Glu Ile Leu Val Arg Trp Glu Glu Val
                    85                  90                  95

Ser Ser Gln Cys Ser Tyr Ala Ser Ser Arg Ile Thr Asp Arg Arg Val
                    100                 105                 110

Gly Ser Ser Ser Ser Ser Val His Val Ala Ser Gln Arg Asn Ser
                    115                 120                 125

Val Pro Pro Asp Met Ala Val Thr Ala Pro Leu Thr Asp Val Asp
                    130                 135                 140

Leu Leu Lys Pro Val Thr Gly Ser Ala Thr Gln Phe Thr Thr Val Ala
145                     150                 155                 160

Met Val His Tyr His Gln Glu Tyr Thr
                    165
```

<210> SEQ ID NO 15
<211> LENGTH: 135
<212> TYPE: PRT
<213> ORGANISM: Human cytomegalovirus

<400> SEQUENCE: 15

```
Met Leu Trp Ile Leu Val Leu Phe Ala Leu Ala Ala Ser Ala Ser Glu
 1               5                   10                  15

Thr Thr Thr Gly Thr Ser Ser Asn Ser Ser Gln Ser Thr Ser Ala Thr
                    20                  25                  30

Ala Asn Thr Thr Val Ser Thr Cys Ile Asn Ala Ser Asn Gly Ser Ser
                    35                  40                  45

Trp Thr Val Pro Gln Leu Ala Leu Leu Ala Ala Ser Gly Trp Thr Leu
                    50                  55                  60

Ser Gly Leu Leu Leu Leu Phe Thr Cys Cys Phe Cys Cys Phe Trp Leu
 65                     70                  75                  80

Val Arg Lys Ile Cys Ser Cys Cys Gly Asn Ser Ser Glu Ser Glu Ser
                    85                  90                  95

Lys Thr Thr His Ala Tyr Thr Asn Ala Ala Phe Thr Ser Ser Asp Ala
                    100                 105                 110

Thr Leu Pro Met Gly Thr Thr Gly Ser Tyr Thr Pro Pro Gln Asp Gly
                    115                 120                 125

Ser Phe Pro Pro Pro Arg
                    130                 135
```

<210> SEQ ID NO 16
<211> LENGTH: 114
<212> TYPE: PRT
<213> ORGANISM: Human cytomegalovirus

<400> SEQUENCE: 16

```
Met Thr Pro Ala Gln Thr Asn Ala Thr Thr Val His Pro His Asp
 1               5                   10                  15

Ala Lys Asn Gly Ser Gly Gly Ser Ala Leu Pro Thr Leu Val Val Phe
```

```
                    20                  25                  30
Gly Phe Ile Val Thr Leu Leu Phe Phe Leu Phe Met Leu Tyr Phe Trp
            35                  40                  45

Asn Asn Asp Val Phe Arg Lys Leu Leu Arg Ala Leu Gly Ser Ser Ala
 50                  55                  60

Val Ala Thr Ala Ser Thr Arg Gly Lys Thr Arg Ser Ser Thr Val Val
 65                  70                  75                  80

His His Val Val Pro Arg Ala Thr Thr Arg Val Val Leu Thr Ala Cys
                85                  90                  95

His Arg Thr Phe Phe Tyr His Pro Arg Pro Met Ala Val Leu Thr Thr
                100                 105                 110

Arg His

<210> SEQ ID NO 17
<211> LENGTH: 425
<212> TYPE: PRT
<213> ORGANISM: Human cytomegalovirus

<400> SEQUENCE: 17

Met Arg Gln Val Ala Tyr Arg Arg Arg Glu Ser Ser Cys Ala Val
 1               5                  10                  15

Leu Val His His Val Gly Arg Asp Gly Asp Gly Glu Gly Glu Ala Ala
                20                  25                  30

Lys Lys Thr Cys Lys Lys Thr Gly Arg Ser Val Ala Gly Ile Pro Gly
            35                  40                  45

Glu Lys Leu Arg Arg Thr Val Val Thr Thr Thr Pro Ala Arg Arg Leu
 50                  55                  60

Ser Gly Arg His Thr Glu Gln Glu Gln Ala Gly Met Arg Leu Cys Glu
 65                  70                  75                  80

Lys Gly Lys Lys Arg Ile Ile Met Cys Arg Arg Glu Ser Leu Arg Thr
                85                  90                  95

Leu Pro Trp Leu Phe Trp Val Leu Leu Ser Cys Pro Arg Leu Leu Glu
                100                 105                 110

Tyr Ser Ser Ser Phe Pro Phe Ala Thr Ala Asp Ile Ala Glu Lys
                115                 120                 125

Met Trp Ala Glu Asn Tyr Glu Thr Thr Ser Pro Ala Pro Val Leu Val
 130                 135                 140

Ala Glu Gly Glu Gln Val Thr Ile Pro Cys Thr Val Met Thr His Ser
 145                 150                 155                 160

Trp Pro Met Val Ser Ile Arg Ala Arg Phe Cys Arg Ser His Asp Gly
                165                 170                 175

Ser Asp Glu Leu Ile Leu Asp Ala Val Lys Gly His Arg Leu Met Asn
                180                 185                 190

Gly Leu Gln Tyr Arg Leu Pro Tyr Ala Thr Trp Asn Phe Ser Gln Leu
                195                 200                 205

His Leu Gly Gln Ile Phe Ser Leu Thr Phe Asn Val Ser Met Asp Thr
                210                 215                 220

Ala Gly Met Tyr Glu Cys Val Leu Arg Asn Tyr Ser His Gly Leu Ile
 225                 230                 235                 240

Met Gln Arg Phe Val Ile Leu Thr Gln Leu Glu Thr Leu Ser Arg Pro
                245                 250                 255

Asp Glu Pro Cys Cys Thr Pro Ala Leu Gly Arg Tyr Ser Leu Gly Asp
                260                 265                 270

Gln Ile Trp Ser Pro Thr Pro Trp Arg Leu Arg Asn His Asp Cys Gly
```

-continued

```
                275                 280                 285
Thr Tyr Arg Gly Phe Gln Arg Asn Tyr Phe Tyr Ile Gly Arg Ala Asp
290                 295                 300

Ala Glu Asp Cys Trp Lys Pro Ala Cys Pro Asp Glu Pro Asp Arg
305                 310                 315                 320

Cys Trp Thr Val Ile Gln Arg Tyr Arg Leu Pro Gly Asp Cys Tyr Arg
                325                 330                 335

Ser Gln Pro His Pro Pro Lys Phe Leu Pro Val Thr Pro Ala Pro Pro
                340                 345                 350

Ala Asp Ile Asp Thr Gly Met Ser Pro Trp Ala Thr Arg Gly Ile Ala
                355                 360                 365

Ala Phe Leu Gly Phe Trp Ser Ile Phe Thr Val Cys Phe Leu Cys Tyr
370                 375                 380

Leu Cys Tyr Leu Gln Cys Cys Gly Arg Trp Cys Pro Thr Pro Gly Arg
385                 390                 395                 400

Gly Arg Arg Gly Gly Glu Gly Tyr Arg Arg Leu Pro Thr Tyr Asp Ser
                405                 410                 415

Tyr Pro Gly Val Arg Lys Met Lys Arg
                420                 425

<210> SEQ ID NO 18
<211> LENGTH: 306
<212> TYPE: PRT
<213> ORGANISM: Human cytomegalovirus

<400> SEQUENCE: 18

Met Arg Ile Glu Trp Val Trp Trp Leu Phe Gly Tyr Phe Val Ser Ser
1               5                   10                  15

Val Gly Ser Glu Arg Ser Leu Ser Tyr Arg Tyr His Leu Glu Ser Asn
                20                  25                  30

Ser Ser Thr Asn Val Val Cys Asn Gly Asn Ile Ser Val Phe Val Asn
            35                  40                  45

Gly Thr Leu Gly Val Arg Tyr Asn Ile Thr Val Gly Ile Ser Ser Ser
        50                  55                  60

Leu Leu Ile Gly His Leu Thr Ile Gln Val Leu Glu Ser Trp Phe Thr
65                  70                  75                  80

Pro Trp Val Gln Asn Lys Ser Tyr Asn Lys Gln Pro Leu Gly Asp Thr
                85                  90                  95

Glu Thr Leu Tyr Asn Ile Asp Ser Glu Asn Ile His Arg Val Ser Gln
                100                 105                 110

Tyr Phe His Thr Arg Trp Ile Lys Ser Leu Gln Glu Asn His Thr Cys
            115                 120                 125

Asp Leu Thr Asn Ser Thr Pro Thr Tyr Thr Tyr Gln Val Asn Val Asn
130                 135                 140

Asn Thr Asn Tyr Leu Thr Leu Thr Ser Ser Gly Trp Gln Asp Arg Leu
145                 150                 155                 160

Asn Tyr Thr Val Ile Asn Ser Thr His Phe Asn Leu Thr Glu Ser Asn
                165                 170                 175

Ile Thr Ser Ile Gln Lys Tyr Leu Asn Thr Cys Ile Glu Arg Leu
                180                 185                 190

Arg Asn Tyr Thr Leu Glu Ser Val Tyr Thr Thr Val Pro Gln Asn
            195                 200                 205

Ile Thr Thr Ser Gln His Ala Thr Thr Thr Met His Thr Ile Pro Pro
210                 215                 220
```

```
Asn Thr Ile Thr Ile Gln Asn Thr Thr Gln Ser His Thr Val Gln Thr
225                 230                 235                 240

Pro Ser Phe Asn Asp Thr His Asn Val Thr Lys His Thr Leu Asn Ile
            245                 250                 255

Ser Tyr Val Leu Ser Gln Lys Thr Asn Asn Thr Thr Ser Pro Trp Ile
        260                 265                 270

Tyr Ala Ile Pro Met Gly Ala Thr Ala Thr Ile Gly Ala Gly Leu Tyr
    275                 280                 285

Ile Gly Lys His Phe Thr Pro Val Lys Phe Val Tyr Glu Val Trp Arg
290                 295                 300

Gly Gln
305

<210> SEQ ID NO 19
<211> LENGTH: 92
<212> TYPE: PRT
<213> ORGANISM: Human cytomegalovirus

<400> SEQUENCE: 19

Met Ala Arg Ser Val Lys Thr Ile Arg Ile Gln His Ile Tyr Ser Pro
1               5                   10                  15

Arg Ser Ser Asn Thr Leu Gln His Met Ser Lys Lys Gln Glu Ser Ile
            20                  25                  30

Ala Thr Ile Thr Phe Gly Arg Ile Thr Cys Cys His Pro Leu Ala Ser
        35                  40                  45

Ile Asn Leu Met Phe Asn Gly Ser Cys Thr Val Thr Val Lys Ile Ser
    50                  55                  60

Met Gly Ile Asn Gly Ser Thr Asn Val His Gln Leu Val Ile Val Leu
65                  70                  75                  80

His Leu Gly Asn Arg Cys Gln Pro Trp Arg Gln Val
            85                  90

<210> SEQ ID NO 20
<211> LENGTH: 176
<212> TYPE: PRT
<213> ORGANISM: Human cytomegalovirus

<400> SEQUENCE: 20

Met Lys Pro Leu Ile Met Leu Ile Cys Phe Ala Val Ile Leu Leu Gln
1               5                   10                  15

Leu Gly Val Thr Lys Val Cys Gln His Asn Glu Val Gln Leu Gly Asn
            20                  25                  30

Glu Cys Cys Pro Pro Cys Gly Ser Gly Gln Arg Val Thr Lys Val Cys
        35                  40                  45

Thr Asp Tyr Thr Ser Val Thr Cys Thr Pro Cys Pro Asn Gly Thr Tyr
    50                  55                  60

Val Ser Gly Leu Tyr Asn Cys Thr Asp Cys Thr Gln Cys Asn Val Thr
65                  70                  75                  80

Gln Val Met Ile Arg Asn Cys Thr Ser Thr Asn Asn Thr Val Cys Ala
            85                  90                  95

Pro Lys Asn His Thr Tyr Phe Ser Thr Pro Gly Val Gln His His Lys
            100                 105                 110

Gln Arg Gln Gln Asn His Thr Ala His Ile Thr Val Lys Gln Gly Lys
            115                 120                 125

Ser Gly Arg His Thr Leu Ala Trp Leu Ser Leu Phe Ile Phe Leu Val
    130                 135                 140
```

```
Gly Ile Ile Leu Leu Ile Leu Tyr Leu Ile Ala Ala Tyr Arg Ser Glu
145                 150                 155                 160

Arg Cys Gln Gln Cys Ser Ile Gly Lys Ile Phe Tyr Arg Thr Leu
            165                 170                 175
```

<210> SEQ ID NO 21
<211> LENGTH: 100
<212> TYPE: PRT
<213> ORGANISM: Human cytomegalovirus

<400> SEQUENCE: 21

```
Met Cys Thr Asp Pro Arg Arg Thr Ala Gly Trp Glu Arg Leu Thr His
1               5                   10                  15

His Ala Ser Tyr His Ala Asn Tyr Gly Ala Tyr Ala Val Leu Met Ala
            20                  25                  30

Thr Ser Gln Arg Lys Ser Leu Val Leu His Arg Tyr Ser Ala Val Thr
            35                  40                  45

Ala Val Ala Leu Gln Leu Met Pro Val Glu Ile Val Arg Lys Leu Asp
            50                  55                  60

Gln Ser Asp Trp Val Arg Gly Ala Trp Ile Val Ser Glu Thr Phe Pro
65                  70                  75                  80

Thr Ser Asp Pro Lys Gly Val Trp Ser Asp Asp Ser Ser Met Gly
                85                  90                  95

Gly Ser Asp Asp
            100
```

<210> SEQ ID NO 22
<211> LENGTH: 117
<212> TYPE: PRT
<213> ORGANISM: Human cytomegalovirus

<400> SEQUENCE: 22

```
Met Arg Leu Ile Phe Gly Ala Leu Ile Ile Phe Leu Ala Tyr Val Tyr
1               5                   10                  15

His Tyr Glu Val Asn Gly Thr Glu Leu Arg Cys Arg Cys Leu His Arg
            20                  25                  30

Lys Trp Pro Pro Asn Lys Ile Ile Leu Gly Asn Tyr Trp Leu His Arg
            35                  40                  45

Asp Pro Arg Gly Pro Gly Cys Asp Lys Asn Glu His Leu Leu Tyr Pro
        50                  55                  60

Asp Gly Arg Lys Pro Pro Gly Pro Gly Val Cys Leu Ser Pro Asp His
65                  70                  75                  80

Leu Phe Ser Lys Trp Leu Asp Lys His Asn Asp Asn Arg Trp Tyr Asn
                85                  90                  95

Val Asn Ile Thr Lys Ser Pro Gly Pro Arg Arg Ile Asn Ile Thr Leu
                100                 105                 110

Ile Gly Val Arg Gly
        115
```

<210> SEQ ID NO 23
<211> LENGTH: 159
<212> TYPE: PRT
<213> ORGANISM: Human cytomegalovirus

<400> SEQUENCE: 23

```
Met Val Leu Thr Trp Leu His His Pro Val Ser Asn Ser His Ile Asn
1               5                   10                  15

Leu Leu Ser Val Arg His Leu Ser Leu Ile Ala Tyr Met Leu Leu Thr
```

```
                  20                  25                  30
Ile Cys Pro Leu Ala Val His Val Leu Glu Leu Glu Asp Tyr Asp Arg
         35                  40                  45

Arg Cys Arg Cys Asn Asn Gln Ile Leu Leu Asn Thr Leu Pro Val Gly
 50                  55                  60

Thr Glu Leu Leu Lys Pro Ile Ala Ala Ser Glu Ser Cys Asn Arg Gln
 65                  70                  75                  80

Glu Val Leu Ala Ile Leu Lys Asp Lys Gly Thr Lys Cys Leu Asn Pro
                 85                  90                  95

Asn Ala Gln Ala Val Arg Arg His Ile Asn Arg Leu Phe Phe Arg Leu
             100                 105                 110

Ile Leu Asp Glu Glu Gln Arg Ile Tyr Asp Val Val Ser Thr Asn Ile
         115                 120                 125

Glu Phe Gly Ala Trp Pro Val Pro Thr Ala Tyr Lys Ala Phe Leu Trp
     130                 135                 140

Lys Tyr Ala Lys Arg Leu Asn Tyr His His Phe Arg Leu Arg Trp
145                 150                 155

<210> SEQ ID NO 24
<211> LENGTH: 316
<212> TYPE: PRT
<213> ORGANISM: Human cytomegalovirus

<400> SEQUENCE: 24

Met Leu Arg Leu Leu Phe Thr Leu Val Leu Ala Leu His Gly Gln
 1               5                  10                  15

Ser Val Gly Ala Ser Arg Asp Tyr Val His Val Arg Leu Leu Ser Tyr
                 20                  25                  30

Arg Gly Asp Pro Leu Val Phe Lys His Thr Phe Ser Gly Val Arg Arg
         35                  40                  45

Pro Phe Thr Glu Leu Gly Trp Ala Ala Cys Arg Asp Trp Asp Ser Met
 50                  55                  60

His Cys Thr Pro Phe Trp Ser Thr Asp Leu Glu Gln Met Thr Asp Ser
65                  70                  75                  80

Val Arg Arg Tyr Ser Thr Val Ser Pro Gly Lys Glu Val Thr Leu Gln
                 85                  90                  95

Leu His Gly Asn Gln Thr Val Gln Pro Ser Phe Leu Ser Phe Thr Cys
             100                 105                 110

Arg Leu Gln Leu Glu Pro Val Val Glu Asn Val Gly Leu Tyr Val Ala
         115                 120                 125

Tyr Val Val Asn Asp Gly Glu Arg Pro Gln Gln Phe Thr Pro Gln
     130                 135                 140

Val Asp Val Val Arg Phe Ala Leu Tyr Leu Glu Thr Leu Ser Arg Ile
145                 150                 155                 160

Val Glu Pro Leu Glu Ser Gly Arg Leu Ala Val Glu Phe Asp Thr Pro
                 165                 170                 175

Asp Leu Ala Leu Ala Pro Asp Leu Val Ser Ser Leu Phe Val Ala Gly
             180                 185                 190

His Gly Glu Thr Asp Phe Tyr Met Asn Trp Thr Leu Arg Arg Ser Gln
         195                 200                 205

Thr His Tyr Leu Glu Glu Met Ala Leu Gln Val Glu Ile Leu Lys Pro
     210                 215                 220

Arg Gly Val Arg His Arg Ala Ile Ile His His Pro Lys Leu Gln Pro
225                 230                 235                 240
```

```
Gly Val Gly Leu Trp Ile Asp Phe Cys Val Tyr Arg Tyr Asn Ala Arg
                245                 250                 255

Leu Thr Arg Gly Tyr Val Arg Tyr Thr Leu Ser Pro Lys Ala Arg Leu
            260                 265                 270

Pro Ala Lys Ala Glu Gly Trp Leu Val Ser Leu Asp Arg Phe Ile Val
        275                 280                 285

Gln Tyr Leu Asn Thr Leu Leu Ile Thr Met Met Ala Ala Ile Trp Ala
    290                 295                 300

Arg Val Leu Ile Thr Tyr Leu Val Ser Arg Arg
305                 310                 315

<210> SEQ ID NO 25
<211> LENGTH: 122
<212> TYPE: PRT
<213> ORGANISM: Human cytomegalovirus

<400> SEQUENCE: 25

Met Val Asp Gln Cys Cys Tyr Arg His Leu His Arg Ser Leu Ser Gly
1               5                  10                  15

Gly Pro Asp Val Leu Tyr Ala Ala Ala Gly Thr Gln Arg Glu Gln Gln
            20                  25                  30

Arg Leu Asp Lys Ser Leu Ala Ala Thr Ala Pro Ser Ala Val Ala Gly
        35                  40                  45

Pro Pro Ala Asp Arg Asp Val Val Asp His Arg Thr Glu Thr His Ala
    50                  55                  60

Tyr Glu Thr Pro Arg Tyr Ala Thr Arg Cys Leu Thr Arg Tyr Thr Thr
65                  70                  75                  80

Pro Val Arg Ser Ala Val Arg Arg Thr Thr Cys Gly Lys Arg Val Ala
                85                  90                  95

Ser Gln Ser Pro Pro Arg Ser Cys Leu Val Ala Pro Gln Ser Ser Pro
            100                 105                 110

Ala His Pro Pro Arg His Pro Glu Gly Gly
        115                 120

<210> SEQ ID NO 26
<211> LENGTH: 642
<212> TYPE: PRT
<213> ORGANISM: Human cytomegalovirus

<400> SEQUENCE: 26

Met Gln Leu Cys Ser His Ser Ile Ser Ser Gln Arg His Val Ala Ser
1               5                  10                  15

Ser Met His Cys Arg Ser Arg His Gln Arg Thr Pro Pro Ser Ala Thr
            20                  25                  30

Thr His Gly Pro Cys Ala Pro Thr Ser Arg Ile Leu Arg Arg Leu Leu
        35                  40                  45

Thr Thr Arg Arg Phe Leu Pro Arg Thr Pro Ser Pro Ser Asn Thr Val
    50                  55                  60

Cys Cys Ile Arg Arg Arg Leu His Glu Arg Thr Ile Arg His Ser Met
65                  70                  75                  80

Arg Cys Arg Arg Arg Asp Met Ala Ser Ser Ala Ser Thr Pro Val Ser
                85                  90                  95

His Thr Gln Pro Leu Ala Ala Asn His Arg Arg Ser Arg Ile Thr Tyr
            100                 105                 110

Ala Thr Thr Asp Pro Thr Asn Ser Pro Thr Ala Ser Pro Ala Lys Ser
        115                 120                 125
```

```
Asp Lys Leu Glu Ala Asp Ala Asp Pro Ala Leu His Arg Arg Pro Ala
    130                 135                 140

Ser Leu Leu Arg His Leu Phe Gln Pro Cys His Ala Gln Arg Gly Thr
145                 150                 155                 160

Ser Asn Arg Ala Thr Ser Gln Arg Ala Ser Leu Asn Ala Val His His
                165                 170                 175

Lys Leu Cys Gly Ala Met Ile Ser Ser Cys Ser Thr Thr Cys Thr
            180                 185                 190

Pro Leu Ile Met Asp Leu Pro Ser Leu Ser Val Glu Leu Ser Ala Gly
            195                 200                 205

His Lys Lys Glu Thr Pro Thr Glu Gly Gly Trp Gly Gly Glu
    210                 215                 220

Gly Glu Asp Asp Val Leu Ala Thr Ile Arg Asn Thr Leu Ser Ala Pro
225                 230                 235                 240

Thr Ser Pro Ala Ala Thr Thr His Arg Leu Ser Phe Pro Gly Glu
                245                 250                 255

Ser Thr Phe Cys Leu Thr Ala Val Ser Glu Cys Ser Gln Arg Arg Thr
            260                 265                 270

Ser Thr Ala Ala Leu Thr Pro Pro Pro Ala Val Ala Ala Phe
            275                 280                 285

Ser Phe Ser Ser Thr Val Ser Glu Thr Gly Thr Phe Pro Gln Ser Thr
    290                 295                 300

Thr Gly Arg Thr Arg Val Asp Asp Thr Ala Val Val Thr Ala Gly Asp
305                 310                 315                 320

Pro Arg Ser Pro Val Thr His Val Thr Leu Leu Gln Ile Phe Arg Leu
                325                 330                 335

Arg Ser Ser Leu Leu Thr Ser Arg Ser Gly Ala Leu Arg Gly Gly
            340                 345                 350

Glu His Glu Ala Ile Pro Lys Val Ala Ser Leu Phe Trp Thr Leu Leu
            355                 360                 365

Lys Ala Thr Gln Ile Val Glu Met Thr His Lys Thr Pro Ser Ala Asp
370                 375                 380

Ser His Arg Asn Pro Gln Lys Tyr Thr Asp Arg Pro Gln Arg Leu Leu
385                 390                 395                 400

Leu Thr Ala Leu Ala Ile Trp Gln Arg Thr Tyr Asn Asp Thr Arg Ala
                405                 410                 415

Ala His Ala Pro Gln Val Arg Leu Leu Gly Asp Ile Leu Thr Tyr Arg
            420                 425                 430

Arg Pro Gln Thr Ala Thr Ala Ser Thr Lys Ala His Thr Gln Gln Gln
        435                 440                 445

Pro Glu Glu Pro Lys Gly Gln Gln Ile Trp Thr Gln Thr Ala Gly Gln
    450                 455                 460

Ala Ala Pro His Gly Asp Glu Pro His Ser Asp Gly Glu Leu Arg Arg
465                 470                 475                 480

Glu Ser His Ser Ala Pro Pro Thr Ser Arg Thr Leu Pro Asp Thr Ile
                485                 490                 495

Leu Ala Val Lys Arg Arg Ser Val Ala Gln Arg Ser His Val Arg Leu
            500                 505                 510

Asp Ala Lys Pro Gly Leu Asn Glu Arg Asp Gly Phe Arg Gln Arg Leu
            515                 520                 525

Leu Leu Pro Leu Ser Gly Tyr Phe Arg Ala Asn Glu Leu Arg Asn Gln
    530                 535                 540

Gln Phe Met Gly Tyr Gly Thr Lys Asn Gly Leu Lys Asn Thr Trp Leu
```

```
                 545                 550                 555                 560
Thr Arg Pro Leu Gly Val Ala Gly Val Arg Glu Thr Ile Gly Glu
                565                 570                 575

Arg Gln Asp Arg Asn Val Ala Asp Ser Ala Thr Gln Arg Val Phe His
                580                 585                 590

Thr Leu Tyr Ala Ala Leu Gln Thr Val Arg Val Trp Tyr Thr Ala Leu
                595                 600                 605

Gly Thr Ala Trp Arg Thr Ser Gly Ser Arg Thr Arg Glu Ser Leu Phe
                610                 615                 620

Asp Gly Pro Arg Arg Asp Arg Gln Ala Ala Arg Leu Arg Arg Leu
625                 630                 635                 640

Glu Leu

<210> SEQ ID NO 27
<211> LENGTH: 336
<212> TYPE: PRT
<213> ORGANISM: Human cytomegalovirus
<220> FEATURE:
<221> NAME/KEY: MISC_FEATURE
<222> LOCATION: (47)..(47)
<223> OTHER INFORMATION: X is unknown (one of the naturally occurring
      amino acids)
<220> FEATURE:
<221> NAME/KEY: MISC_FEATURE
<222> LOCATION: (49)..(49)
<223> OTHER INFORMATION: X is unknown (one of the naturally occurring
      amino acids)
<220> FEATURE:
<221> NAME/KEY: MISC_FEATURE
<222> LOCATION: (115)..(115)
<223> OTHER INFORMATION: X is unknown (one of the naturally occurring
      amino acids)

<400> SEQUENCE: 27

Met Val Phe Val Ser Gly Thr Ala Leu Gly Thr Gly Phe His Arg Ala
1               5                   10                  15

Glu Gly Ser Phe Cys Gly Cys Glu Gly Arg Ser Phe Phe Arg Thr Leu
                20                  25                  30

Gly Thr Gly Leu Gly Asp Gly Gly Cys Ala Gly Arg Arg Trp Xaa Arg
                35                  40                  45

Xaa Val Ala Gly Thr Gly Ile Thr Leu Gly Thr Gly Thr Arg Gly Pro
50                  55                  60

Gly Leu Arg Asp Gly Gly Asp Gly Gly Val Cys Gly Glu Asp Gly Gly
65                  70                  75                  80

Leu Leu Arg Arg Gly Arg Gly Leu Ala Gly Pro Ala Val Ala Gly Val
                85                  90                  95

Cys Gly Asp Gly Gly Leu Leu Gln Arg Arg Gly Leu Arg Gly Gln Glu
                100                 105                 110

Cys Ala Xaa Pro Gly Gly Phe Ala Gly His Gly Thr Gly Gly Gly
                115                 120                 125

Gly Asp Ser Thr Asn His Thr His Thr Gln Leu Thr Ser Ala Val Ala
                130                 135                 140

Leu Ser Glu Pro Pro Leu Phe Phe Ile Asn Val Leu Ile Pro Pro Ala
145                 150                 155                 160

Tyr Thr Arg Asn Ala Ala Cys Ser Tyr Ala His Thr Leu Ser Leu His
                165                 170                 175

Ser Asp Met Leu Leu Arg Leu Cys Thr Ala Ala Ala Asp Thr Ser Gly
                180                 185                 190

His Arg His Leu Pro Pro His Met Ala His Val Leu Arg Arg Pro Ala
```

-continued

```
            195                 200                 205
Ser Tyr Val Val Cys Ser Gln His Gly Ala Phe Phe Pro Ala Arg His
    210                 215                 220

Leu His Arg Thr Pro Ser Ala Ala Phe Ala Val Ala Ser Thr Arg Glu
225                 230                 235                 240

Gln Tyr Ala Thr Ala Cys Ala Val Ala Ala Ala Thr Trp Pro Pro Arg
                245                 250                 255

Leu Pro His Leu Phe Arg Thr Pro Asn Leu Trp Leu Pro Thr Thr Asp
                260                 265                 270

Val Gln Gly Ser Arg Thr Arg Arg Pro Ile Pro Pro Ile Leu Gln Arg
                275                 280                 285

Pro Arg Pro Pro Ser Gln Thr Ser Trp Lys Pro Thr Gln Thr Gln His
    290                 295                 300

Ser Ile Asp Ala Arg Pro Arg Cys Cys Ala Thr Ser Ser Ser Pro Ala
305                 310                 315                 320

Thr Pro Asn Ala Ala Leu Pro Thr Glu Pro His Pro Arg Gly Leu Pro
                325                 330                 335

<210> SEQ ID NO 28
<211> LENGTH: 11950
<212> TYPE: DNA
<213> ORGANISM: Human herpesvirus 5 (AD169)

<400> SEQUENCE: 28
cctcgccatg aggatcgcga caggcgcgtc gaggggcag  gaacacccctt gcggattgac      60 attcttggtg gtgtttcgtt gttgtcggta gttgttgttg acgatgagga taaataaaaa     120
tgaccttgtt tttgttctgt tttctcttgt tgggaatcgt cgactttgaa ttcttcgagt     180
tatcggaaag ctgaggtacc caaatgtctg tagctttttt ctttttaccc tcttgtttat     240
catctgcgat tcgtggtagg taggagaggg aaatgataat ccgagattaa ggaaaggaga     300
agataaaaaa taaaaaaaaa taataaaaca gaagccgacc ggccgccgac ccgttcccca     360
ggaccagcct acgaggaacg gataacgcgg tggcgacggc agcggtggtg gcgctggggg     420
tggcggcagt ggtactgctg atggtagtcg ggacggagga gaggcgatgc atacatacac     480
gcgtgcatgc tgcatgggtg gatggtacgg ccgggagacg cggaagagaa actcacataa     540
aaaggtgaca aaaagagcgg ttgaaaaaag aaaacaagat tcgaccagac agaagagaag     600
gaccggggct tggcgaccct tccacgactg ctgttgtcat ctcggctcct ccgtcttctc     660
ccggccacgg gcggctaagt caccgccgtt ctccccatcc gtccgagcgc cgaccgacca     720
gccggccgat tcgcccgccg gggcttctgg agaacgccgg ggcagcagcg atctggggaa     780
gctgctaaac ccctgcgttt ttatatggta gctctgccga gcgcgggctg acgcgttggg     840
taagcggaaa gacgtgtgtg acgaaaaggg gtcccatggt atttcacgtg acgatgagga     900
gatacggttt ggagcacata cggtttagaa aaaggggagtt gtcgtgacaa gggctgaggg     960
acctctgtct ccatgtgtgt ataaaaagca aggcacgttc ataatgtaaa aagaacacg    1020 ttgtaaacaa gctattgctg tatcattcgg ctgactatgc ttcattcgga ctgatttttct   1080 tttcctaacg gcgtaactta agtgattaa cgtatgatat tgttccccca gagttatact    1140
atagtcatca tcctaaaatt cagatataaa tgaacacatg tcgtatggga ttattaagaa    1200
accgaaactc tccacagttc accatcttct tcgtcattca accgatgacc cactccgtac    1260
aacgaatcag tctgctgcgt catattgcaa agcacaagcg acgtatgcga caacttgaa    1320 acacaggctg ttgtattgac gaccgttgta ccattattag tcaccaccgt tatcccatgt   1380
```

-continued

```
ttcccacccg atggaaaacc gtcttctatc atcaactgtg gtaagatttc gaccctgcga    1440
ggtattcagt ttcctcatat ccataacctg gattttatca ttaaacccca atattaaaca    1500 ctttttagt accccccacc caccaaaaaa tgtgactgga ccggttccta gcagctctgg     1560
gagccatgtt caggttgaac cacagctaca gcgaaaccga gtccagtgac cggtaaccac    1620
gtccagcccc tgcgtatgta ccagtccaag cacgtccggt cattgttcta cacaggaaat   1680
ctaactaggt caacgcaatt ttattccacc gttacgcaga atactaacaa aaaaacacac   1740
aaatttaacg aattacacgt agtttattac atgaaaactg taagaacacc aattcactaa   1800
gcgatacaac atttagctga cttccaagtg ccacacatca ccactgtatt catccatgtt   1860
ttcaccgaac caacgagaca gatcgaagaa gccagaatct cccgacttta aattacataa   1920
atccaacgta ttatgaccac agctcgacac acaaatagtt gcgttactat tcacagtagc   1980
attacctata cccgtaacgt tgcacaacca ctgatcacca ttgttaccaa aaacggtttt    2040
ccacttagtt gtcaacggat ctttcctatg cgtaatggta aaattactac cagtcgtcgc   2100
ttttagctca ttacgagtat tatccgcatc cacatatatc aacgtcatag ctaggcacgc   2160
tataagtacc cccccccac aatggaatgt tgccaaaccg gttctttccc gttatagcca    2220
tagcgttccc aggcaaaagc aaacgccaaa cctaatgcag tgaaaagcgc ttgcagccag   2280
aaccagctta tgtaccagcc acaatcacat ccggttattg ttttccacagg aaatcctacc   2340 aggcaaagcc ccgcttgttt tgttcctatc ttgtttagca attcgtaaac tgtcagccta   2400
gcgacgtccg tttagatcaa aagtcacgta tatagcgacg ctgtttccat ccgtttcccc    2460
gtcccgccgt ttccgaacaa ccccacccggg ttcagacaac cgaccaccaa cagaaatata   2520
cacacagacc actgggagtt cagttaaaga tttcatcagg tttattttgg ctgctgctag   2580
tcttttgctt cttagaaaaa aaatacccat atagagaaat aatgatagtt tgacaacaca   2640
tatggcaggg atttcttctt catcaataag atatgcaatt cccccaggga gagactttca   2700
acaattgaat ttacaaaaac aaaattacat caggagaaag agaggataca ttaataaata   2760
tattatatct ggtgtatata ctgaatgctg ctggttcata aggtaacgat gctacttttt   2820
ttaattccaa gatggttttt ctttgttagt cttttgttga cttgctggtt cctaaaagtt   2880
cgcaaaaacg attgtgtgaa gattttatga cgttggttga ctagttcatg agattctgct   2940
gtacgtgtga tggttattcg ctggttcgtt ctaagatgag tatcgtactg tgtctgcgat   3000
ggtcgtctct tactgcatt ctctcggctg cctcttgctt tcatgattga aaaggaaaaa    3060
aggactccga gggcgcggtc atcttttact tttcggtttt ctcgttggcg ggtcagaggt   3120
agtcagatca tgagactgtc gtggtcgatg aaactgtgtc tgctcaagtg acgtccattt   3180
cttgtacgga gaaaaagtc atcgggataa ataaggctat acaaggcgtt gtcaagcgtg    3240
cggctctaaa caaattaagc gatacaaaat tacagtaata cgaataataa attaccccc    3300 tcccctgtg gtcccccgag acgagagcca cccatcgtgt actctcgcac cacccacgac   3360
cacagaggga gacgggacga agagacgacg cacagcgcca tctcctcctg gaggccggcg   3420
acgttaactg ctacagctgc ggcggcgaag acagctgcga tttgtcggcc gacatgccga   3480
tggtatgggc ggcggcggca atggccgcgc cagcggggag gagaggagag agaagaggag   3540
cggggcgtcc gaaggcgagg atggcatggt ctcgccggag cgcccggctt ttatggaaca   3600
ctcgcgtccg gttgggtatc acccacagga agatgagtca caacttccaa accatcttga   3660
gacccgagta acggtttaca ggtcgcacgc cagtcagcta aaaacagcgg acagtcccac   3720
```

```
gctgtttctg ttgtggctct ctccagtttc ctcatcaccg tcccggtctc cgtcgtcatc    3780
ggaagaatac cacccgctct catgcggcag tcgatcggcc tcgacgaacg agacgcggcg    3840
acgcctctcc acggccgact ggttgtggtg gtgaaagaag agcaccagca atcccaggag    3900
gagcaacaag ccctcacatg tccaggaggt cggggagagg gcctgtcgga gatggccgtg    3960
aggcatcacg tacggcagct gaggagaaac ggagaagaaa ggaaaattac cgtcaggggc    4020
cggggttctt attagagaaa cagcacgtag gtcaggatcc agatgctaat ggcaatcatg    4080
atgacgatga tcatgcaggc caagacgcgg cgcaccaatg ccgaatccaa tagccgccgt    4140
gcctccggtt ggtggccggc ggcatctaga gacatgattt ggggggggacc ggcggcgcaa    4200
aaagacaggg agatggacag tgtcacggtg ttttgttata attaggacat ggggaccgga    4260
agccgagaca gagtactaca gggtgttgaa gggtaacgtg agggagatca tgtcatgggc    4320
gggctgaaga ccgtgcgggg aggattgacg tgtgcggtgc ttgtggaaca cggtgtttta    4380
atatgtatcc gcgtgtaatg cacgcggtgt gctttctggc actcagcttg gtaagctatg    4440
tggccgtctg cgccgaaacc aaagtcgcca ccaactgtct cgtgaaatca aagatacccc    4500
atttgacgtg caagtgcagt ccgaataaca catcatctaa taccggcaat ggcagcaagt    4560
gccacgcgat gtgcaaatgc cggatcacag aacccattac catgctaggc gcatactcgg    4620
cctggggcgc gggctcgttc gtggctacgc tgatagtcct gctggtggtc ttctttgtaa    4680
tttacgcgcg cgaggaggag aaaaacaaca cgggcaccga ggtagatcaa tgtctggcct    4740
atcggagcct gacacgcaaa aagctggaac aacacgcggc taaaaagcag aacatctacg    4800
aacggattcc ataccgaccc tccagacaga aagataactc cccgttgatc gaaccgacgg    4860
gcacagacga cgaagaggac gaggacgaca acgtctgata aggaaggcga gaacgtgttt    4920
tgcaccatgc agacctacag cacccccctc acgcttgtca tagtcacgtc gctgtttttg    4980
ttcacaactc agggaagttc atcgaacgcc gtcgaaccaa ccaaaaaacc cctaaagctc    5040
gccaactacc gtgccacctg cgaggaccgt acacgcacgc tggttaccag gcttaacact    5100
agccatcaca gcgtagtctg gcagcgttat gatatctaca gcagatacat gcgtcgtatg    5160
ccgccacttt gtatcattac agacgccatt aaagaaacca cgcgtcaggg cggtgcggcg    5220
ttcgcgtgca cgcgccaaaa tctgacgctg tacaatctca cggttaaaga tacgggagtc    5280
tacctcctgc aggatcagta taccggcgat gtcgaggctt tctacctcat catccaccca    5340
cgtagcttct gccgagcctt ggaaacgcgt cgatgctttt atccgggacc agggagagtt    5400
gtggttacgg attcccaaga ggcagaccgg gcaattatct cggatttaaa acgccagtgg    5460
tccggcctct cactccattg cgcctgggtt tcgggaatga tgatctttgt tggcgcgctg    5520
gtcatctgct tcctgcgatc gcaacgaatc ggggaacagg acgctgaaca tctgcggacg    5580
gacctagata cggaaccttt gttgttgacg gtggacgggg atttacagta aaagatgcgt    5640
gtcgcctgcc aagacctca ccatctcacg tacaggcata cggcgtatac aatcataata    5700
ttctatattc tgcatagagt tacatgcaac agtactacta ccaatactgc atccatcaca    5760
tcacccaaca ctgcttctac caccttttgt accagcgtat tttctactcc gaataacaac    5820
acatcaacga cgccacacac atctgtcacc tcacaagcgt caaccattgg caacatcacc    5880
aacgttacct ccgacttgag tactttcaca accgtatatt ctcacattcaa tacatcatat    5940
gctaatatat ccaatacggc tgccactaca gaattgattt caacaaatac caacactata    6000
ttatcttta ccaacgtaac agcaaacgct acatcatctt ataacacaac aatcaccgta    6060
actatcacgt cagatgaaac ttcgcacaac gtatccacta atactgcact tataagcacg    6120
```

```
ccatggctta caaattgcag cgccacaacg tacaccacgt acaaccgtac taactcttcc    6180
aacgcttgtc acacagagac aacaatcata cgtttcaaag aaactaatac aacaggaata    6240
gaagggagta atgtcaccat aaaaggtaat tctacgtggg attgtctttc agtcgcctgg    6300
atacgacatt acaatcgatc cacacacgga catcatctag gtcatcgtaa aacgcacat    6360 acccaatctt ggtattggtt acgcatcctt acctctcata ctgtatgtca ttctcaacat    6420
gaaagacctt cactgtacca tgacttatgt cgttcgtgca acaacacaga actacatctg    6480
tacgatctaa atatcaccaa ttccggcagg tacagcagac gttgttttaa agaaaattac    6540
ttcacaggac atcacgaaga tgaaaatttc tacctattag taacaccaaa aaatcatact    6600
gaagctatta atgctacttt cgtttgccct agatacaaca ccgatatcga aaatgaagat    6660
agagagaaag gaagtcaaca tactaacaat acacatcacc acaaacgtaa tctctatcat    6720
agctcgcaaa gaagccgcac cgtatggacc atcgtgttgg tttgtatggc ctgcatagtt    6780
ctgttttttg cacgacgagc ctttaacaaa aagtaccata tgttgcaaga caccgtcagt    6840
gaatcagaat tcattgttcg atatcacaca gaacatgaag attgagctac gtttccgggc    6900
agacatctta tgaagctgaa caataaacta aacattctg taaggctcag cgttcaaagg    6960
aatattaatg cccattgagc gagaactaat attgcaatgg actggcgatt tacgttatg    7020 tggacgatac taatatccgc gttatcagaa agctgcaatc aaacctgttc ctgtcaatgt    7080
ccctgtagta ctaccgttaa ctattccact agtactgaga cagccacatc aacatacagt    7140
acaacagtta tcagcaataa aagcacttca gaatctataa attgctctac tgcaactgca    7200
ccagcaacca ccgtttctac aaaaccgtcg aaaacaacca cacagatatc cacaacgaca    7260
aatacaaacg ttgagactac cacatgtacc aacaccacca cgaccgttac ttgtgatggt    7320
ttcaattata cagtccataa aagatgcgac cgcagttacg aggtaatcaa cgtaacagga    7380
tacgttggtg gcaacataac tctaaaaat gcaatcagac tgagaaatgg cacaatgtag    7440
actggattca ttatgagtac cccacgcata aaatgtgcga attaggcaac tatcaccaaa    7500
caacaccacg gcacgacata tgttttgact gcaacgacac ctccctaact atctacaact    7560
taaccacaag aaacgctgga aaatatacca ggcatcaccg tgataacggt caagaagaaa    7620
attactacgt aacggtgtta attggagaca caacgttatc cactcttggc acatgccctg    7680
taagatataa agaatctagg aacactgaaa acaccattgg aagtaacatc ataaaaacca    7740
ttgagaaagc taacattccc ctgggaattc atgctgtatg ggcaggcgta gtggtatcag    7800
tggcgcttat agcgttgtac atgggtagcc atcgcattcc caaaaaaccg cattacacca    7860
aacttcccaa atatgatcca gatgaatttt ggactaaggc ttaacatgca catcaataaa    7920 cttttttaa ccaataacat gtctctgttt tttttgtta acaacctatg atataaagcg    7980
gtatattcaa tcattactaa acaaaaaaac atgggcatgc aatgcaacac taaattgtta    8040
ttgccagtcg cactaatacc ggttgtaatc atcctaattg gtactctagt gcccatactt    8100
ttacatgaac aaaaaaaggc gttttactgg cgacttttc tgcaaagtca acatgtagaa    8160
gcacccatta cagtaacgca gggagacaca gtctacctag atgctagcaa taatccctgt    8220
aattattcca gcttttggta ccacggtaat tgcgaacttt gtggatggaa cggatatcta    8280
cgcaatgtta cacattacta cacaaacaca tcgtgttccc cgcaattcat gtgcataaac    8340
gaaactaaag gtctgcagtt atataatgta acattaaacg attcaggtgc ttatactgaa    8400
cacgtttacg aatgtgatct ttcatgtaac attactactt ataacgaata tgaaatactc    8460
```

```
aattacttcg ataactgtaa ctacaccata aatagcacca agcatattat caccgtggtg   8520
tcttcacgtc attctaaaca aacaaattcc cacgtatcca ctcacgctgg ttgggcagcc   8580
gccgtggtga cggtaattat gatctacgtt ttgatccact ttaacgttcc ggcaactctg   8640
agacacaaac tacgaactag aaacaacgta atcgcatag cgtgattaca aagtatcgac   8700
actaatttat ccaagataaa atttgattac tccgtgcggt tctcaaaaac tgtaaggtcc   8760
cgcttttcta ctccatcatg aaggatcgca atagaatact gctatgtatc atctttattt   8820
gcatcatgtg cctcatttgt atttacttta acgtcgttg tgttcttact ccgtctccag    8880
acaaagcgga tctgcgagtg gaatttccct cgttaccccc gtgtatcggc atacaatgtg   8940
ctgcatgaga acacgcgtga cacatagcgt acccctggac ggtacagttt atgataacgt   9000
cattcagggg aagtatacat tactatcgac gtgttatcac agaacacaca gattttctgc   9060
gtgttttata aagagcgtc tcgaagcagc ttgagccaca ctacggtcca gatgacgagc    9120
gtaatcaaaa atatgccgcg cagtagtcga aagccgtact gagcgtgcga ggcgggtagg   9180
gtgccgaacg acggatatgc gtcgttgtca tcttcgacta aaggatcgc gaccgagtct    9240 tcggccatgt taaacgtcac cctgtgtggc tggtatgtag cgtatccggt ttggaattgt   9300
tctgctccag ctcggggat agtgaggaat tctcaaggga tacgggaccc aatgactgga    9360
taagagaagg gttttttcccc gtaagatgat cctcgtatca catgaggtct ggatatgtat  9420
aaatgaagag tgaaataggc acagggaatc agatgccagc ctcgtgatgc agccgctggt   9480
tctctcggcg aagaaattgt cgtctctgtt ggcttgcaaa tacatcccac cttaagcgat   9540
gagtccataa agcaccgttg tccgggtacg gtgaaagtga ctcggattgt agcacgtccc   9600
ttttttttgt ttttgtatcg cttatcgcca ctgacagtgc aatatttga tcgtgaggct    9660 gagtatggtt atgatgctta gaacgtggag attattacca atggtactac ttgccgcgta   9720
ctgttattgt gtttttggga cttgttcaat cggcacgacg actgctcccg tggaatggaa   9780
gtctcccgac cgtcagattc ctaagaatat tacttgcgct aactactcag ggaccatcaa   9840
cggcaacgtt acatttcgag gtcttcagaa caaaacggaa gacttttttgc actggttgtt  9900 agggtgggggt cataagtcca tctgttcgtt cttcccgaaa ctccagggca actataacga  9960
acaacattac agatatgaag tagcgaacct gacgtataac tgcacctata accgcttgac   10020
gttgctaaat ctgacgacgg aaaacagcgg aaagtactat tttaaaaggg aagatgcgaa   10080
tttcaccttt tattactctt gttacaacct gaccgtgtcc taaagaacgc acgtgaagtt   10140
ccacagagcc gcgtggctgt agctattgtg tttacgttgc ttttgaaatg ttaagcgtcc   10200
ctacggcgct aacatgtttc taggctactc tgactgtgta gatcccggcc ttgctgtgta   10260
tcgtgtatct agatcacgct taaagctcgt gttgtctttt tgtgtggttgg tcggtttgcg  10320 tctccatgat tgtgccgcgt tcgagtcctg ctgttacgac atcaccgagg cggagagtaa   10380
caaggctata tcaagggaca aagcagcatt cacctccagc gtgagcaccc gtacaccgtc   10440
cctggcgatc gcgcctcctc ctgatcgatc gatgctgttg tcgcgggagg aagaactcgt   10500
tccgtggagt cgtctcatca tcactaagca gttctacgga ggcctgattt tccacaccac   10560
ctgggtcacc ggcttcgtct tactaggact tttgacgctt ttcgccagcc tgtttcgcgt   10620
accgcaatcc atctgtcgtt tctgcataga ccgtctccgg gacatcgccc gtcctctgaa   10680
ataccgctat caacgtctcg tcgctaccgt gtagctagtt agccagctgt gtatagtttg   10740
ttgtgttttg cttttgcata tttgtttttca gtcagagagt ctgaaacggg gtgggaggga   10800
cttttacggg taatgcatgc taagatgaac gggtgggctg gggtgcgctt ggtaactcac    10860
```

```
tgtttgaata cgcgctcacg cacatatgta gcactcaaca tgttagcttt tgcccgcacg   10920 cccggggcg tgccgagctg ccttttaat aaagtctggg tttccagata cgcgctggtt   10980
ctgattttga tggtttgtgc ctctgaaagc tctacgagct gggccgtgac atccaatcga   11040
ctgcctaact gtagcacgat aactacaaca gcgggtcaag acgctgaatt gcacggtccg   11100
gcaccgttaa gctgtaatgt gacccagtgg ggacgttacg agaatggaag cacacccgta   11160
ttatggtgca ctttatgggg atcacgcacg cgagtctcat taggacaccg tgtagcgttt   11220
ggctgttctt ggaaaacatt ttttatttat aacgtttctg aaagtagtgg tggcacttat   11280
tatcaaaaag gttacaactg caccgacaaa catataacac tatcttgttt caacctaacg   11340
gtggttcctc gagcggttca agcacaacc accgtaatga cacccacggt ggttacaaac   11400
tccacattca gtgtgtcact tgttgcgtcg agactgacga caaattccag cgcgtttaga   11460
cacgctagtt atcaacggca acagcgtgtc ggaaacggga cgttatccaa gaacataact   11520
aacttggcat tcacctacgg cagctggggc gtcgcgatgc tgctgttcgc cgccgtgatg   11580
gtgctcgttg atttgggttt gcctcaatcg gcttggcgac gctggcgaag ccacgtggac   11640
gatgaagaac gtggtttgtt aatgtaggaa ataaaggca ctgtttgagc atgactgttt   11700
ccaaaccgta acgtggtaaa taaatcatg cttccgacgt gagctcccat cttctaacgg   11760
ttacacaatc ccgttggaca atacatcata tgtacaataa actgttgatt ttggcgttgt   11820
ttacccccgt gattctggaa tccatcatct acgtgtctgg gccacaggga gggaacgtta   11880
ccctggtatc caacttcact tcaaacatca gcgcacggtg gtttcgctgg gacggcaacg   11940
atagtcatct                                                         11950

<210> SEQ ID NO 29
<211> LENGTH: 14078
<212> TYPE: DNA
<213> ORGANISM: Human cytomegalovirus

<400> SEQUENCE: 29
cggtctggca gcgactggaa cccggacgcg tagccggcgg cgccgcgcgt catcaaaaag     60
tgcaggaact gttgcagcgc ttgggtcaga cgctaggcga cctagaactg caggaaacgt    120
tggcgacgga atactttgcg ctgttacacg gaatccagac cttcagctac gggctggact    180
ttcggtcgca gttggaaaag atccgcgatc tgcggactcg ttttgcggaa ctggccaagc    240
gacgcggcac gcgtctctcc aacgagggag tcctgcccaa cccccggaaa ccgcaggcga    300
cgacttcact gggcgccttt acacgcgggt tgaacgcgct ggaacgacac gtccagctgg    360
gtcaccagta tctgctcaac aagctcaacg gctcatcgct agtctatagg ctggaagaca    420
ttcctagcgt gcttccggca acacacgaga ccgaccccgc gctgataatg cgcgaccgcc    480
tgcgtcgcct atgcttcgcg cgtcaccacg acaccttcct tgaagtggta gacgtcttcg    540
gcatgcggca atcgtcacg caggccggcg aacccattca cctggtcacc gattatggca    600
acgtagcctt taagtacttg gcgctgcgag acgatggtcg gccctggca tggcggcgcc    660 gctgtagcgg cggaggactc aagaacgtcg tcaccacacg ttataaagcc atcacggtag    720
ccgtggccgt ctgtcagaca ttgcgcactt tctggccaca gatctcgcag tacgacctac    780
gaccctacct cacgcagcat cagagccaca cgcaccccgc ggagactcac acgttgcata    840
accttaagct cttttgttat ctggtgagca ccgcctggca ccagcgcatc gacacgcagc    900
aggagctgac ggccgccgat cgcgtaggca gcggcgaggg tggtgacgta ggggaacaga    960
```

-continued

```
gaccgggccg cggtaccgtg ctgcgcctga gtctgcaaga gttttgtgta ctcatagcgg    1020
ctctgtaccc cgagtacatc tacaccgtcc tcaaataccc ggtgcagatg tcactaccct    1080
ccctcacagc tcacctacat caggatgtga tacacgcggt agtcaataac acacacaaaa    1140 tgcccccga ccacctcccc gaacaggtca aggccttctg tatcacccc acccaatggc     1200 ccgccatgca gctcaataaa ctgttttggg aaaataaact ggtacagcaa ctgtgccagg    1260
taggcccgca aaaagcaca ccgcccttag gcaagctatg gctctacgcc atggccacgc    1320
tggtctttcc acaagacatg ctgcagtgtc tgtggctaga actgaaaccc cagtacgccg    1380
agacatacgc ctcggtgtcc gaattggtac agacgttgtt tcagattttc acgcaacaat    1440
gcgaaatggt gaccgagggg tacacgcaac cgcagctccc caccggagag ccggtgcttc    1500
agatgatccg cgtgccacgt caggacacaa ccaccacaga cacaaacacg accacggagc    1560
cgggactttt agatgttttt attcaaacag aaaccgccct agactacgcg ctgggctcct    1620
ggcttttcgg cataccgtg tgtctcggcg tgcatgtagc cgacctgctg aaaggccaac    1680
gtatactagt agcgcgccac ctcgaataca cgtcgcgaga ccgcgacttc ctccgcatcc    1740
aacgctcccg ggatctcaat ctcagtcaac tgctccagga cacgtggacc gaaacgccgc    1800
tggagcactg ctggctacaa gcccaaatca gacggctacg cgattacctg cgtttcccca    1860
cccgcttaga gtttattccc ctagtcattt acaacgcaca ggaccacacc gtcgtacgcg    1920
tgctgcgacc gccctccacg ttcgaacagg accacagtcg gctggtgttg gacgaggcct    1980
tccccacctt cccgctgtat gaccaagatg ataactcatc cgcggacaac atcgctgcgt    2040
ctggcgccgc tccaacaccg ccggtacctt tcaaccgcgt gccagtcaat attcagtttc    2100
tgcgtgaaaa cccgccaccc atcgcgcgag ttcagcagcc gccgcgccga catcgtcatc    2160
gagcggccgc ggccgcagac gacgacggac agatagatca cgtacaagac gatacatcaa    2220
ggacagccga ctctgcatta gtctctaccg cctttggcgg gtccgtcttt caagaaaacc    2280
gattgggaga aacaccacta tgccgagatg aacttgtggc cgtggcgccc ggcgccgcca    2340
gcaccagttt cgcctcgccg cctatcacgg tgcttacgca gaacgtcctc agtgctctag    2400
aaatactgcg gctagtgcga ttggacctgc gacaactggc gcaatccgta caggacacta    2460
ttcaacacat gcggtttctc tatcttttgt aaccgacact gacagtagcg ggtaataaaa    2520
acaataggat ttttatcgtt tttttatgtt acaaaacaac gtatcacttt cacggtgatt    2580
tattcttgct attccttttc cccttgggct gtcagcgccg ggtgcgcgac acggctacca    2640
tgcgcaacag gtccagctta aaggcgcact tgtcattaaa caggctggac atgcgcgtgt    2700
acttgctcag catggtggcc aacaccgggt gggtggcctc tgatatctcg gtcggcagct    2760
ccaaaacgac gttaacgacg tgacggtgtt tttcgtcccg cttgttggcc accgtgggtc    2820
ccggcgcggt gttagacatg gggcaggccg tgggggagg acgaagagga agccgctgct    2880
aaaccgccgc gcgcctgctg cacaatgtgg ccgccgacgt ggcaggcggt ctgtttaacc    2940
agcgcgcagc cccgacacag cggggcgccg tcctcgcttt ccaaacagct gtcgcggtac    3000
tcgcccgtct gacagcgcgc gcacagcagg ccgtgcccgt gcgaagtgag gcgcaggaga    3060
cgcgggaccg tcacgtcgcg taccaccaca gtggagtcgc aggtgcgtgc cgcgcagggc    3120
agaatgacgt cgaaagccag ccggtgatcg tacacgcac aagccgcgtt gaggcccagc     3180
acggctttcc agcccacgcg tacgcagcgc tgtccaaaga gcgtctcgga gacgagctcg    3240
tagacgcgct gccgcaccac ccgctgactg ccgcagagcg agcagtgcac gagctcggcg    3300
tgcgtgttga agatgacgct cttttcttga cggtcccgat aatagaacat cgagttgagc    3360
```

-continued

```
ggaaagtttt gctggcagtg tagcttttcc ttacccaggt tgaggcagtg tccgcactgc    3420
cgacagacca cggccaccag cgagcgcgcg tccagatggc gctcgcactt gagtcgacac    3480
agacaccaga gcggcaggtc gatgacgctg ccgatgaggc cgccgcgcag cgcggcgctg    3540
agtgcaaaga ggacgatctt ggtgggctct acgtgacgcg cctgctgtcc ggcgcccgcg    3600
tgtcctaccg ccgcagctgc cgccgtcgag cctcctccgc gcgtctcgtc gtgcagaccc    3660
agtgcccgca acggcaccag gtatcgcgga cacgtgtcgc aaaacgtctg caccgcttgt    3720
cgggccagta cgtagagcgg gtttccgcag ggtaccttcc cggcgtaccg gcgcaaggct    3780
gcgatgaggc cccgcaactg cggcgaccgc ggctgccgtt ggtgacacca ctggttacgg    3840
tggtatacgg ccaaatcagc gcgggcgtcg aagcgcttgg cgcgtagtaa tgctaggcac    3900
ggcgagctgg tggggtgaag cacgggcagc cgaaggtcca ccccgaaaag gaaacggtga    3960
aggtcaccta gcagcgaggc ggtgacaccg tccaacaacg cgtgcagccg ctcgggcggg    4020
tagagccgca gacggcgcag caggtagtcg gtgtcgtagc gttcgaaacg cagaaaggcc    4080
atcgtgcgga cggccacggt gtgcagacag tccatgctgt agacgtaagc gagaaacaca    4140
aagtagggct tggtcataac catacgctga agagcgccg tcaccgcctc ccgctcggct     4200
tgccgacaca ccagccattc gcgcaggaag cgttggtaga cggtcgcc cagctcgcga      4260 ttcagaaagc gcttatccgt cacgaagaga tgaaggacg aagaacgtgg cacgtgatgc     4320
accagctgct gctggaggac cgccgacgtc tgcgccgcaa actgcgccgg tggctgcgac    4380
gtttctaccg ccgcttcctc cggctgcagc gcaccgcgc cgatcaccag ctgcacatgg     4440
aaatggtcct cgtgaacgca gaggggcgcg aagagacggc gcagagcctg gtggaactca    4500
tcagtcgcgg tgtgcggagc gtgtcggaga cgacgactgg ccatgaccgc gccacagcag    4560
agccagcacc agcagaagag ccagcaccag cgggcccaga gtcgcaaagc gcgcgggcag    4620
ccacggccca gactgcggtc gcgatgcgcc ggagcgcgct cgccaccacg atgacggtgc    4680
ccaacgataa ccagtccgct ccaaggacgg cgcgcacggc ggagacggcg gatgacggtg    4740
atgggtcgac acccctcgcc gacgactcac gtgctcctcc agaggccgac gcgcggaccc    4800
tccgacgtcc tggcccgccg ctgccgctgc cgccttccct tctcccgcca gagccagcaa    4860
ctcctcctcc tcttcatcag cgtctccctc gcttgcgcat ccgcatcgtc ccatacaggc    4920
ctcacaacga cacagccgcc acgaccccgc cgccatgggt ggcggcggcg gccgaggccc    4980
ggcagcggcg ccgccagcgg cgaccatggt gggagagcaa ctcggatgac gaggaggagg    5040 aggggagat gcggtccgag aggaccgctt tcccgccgtt cgcgtaagcg cggccgacat     5100 gcggcgcgc cacagggacg gaccgctgcc gctgtgactg cttacggtga cgtggttccg     5160
gaccgccaac gacgtcgacg cggctttctt ggcgtacagc tcgcgcagca gattctcgta    5220
ctcgccctcg ttttcgggtc cgaaggcgat gagctcgatg ttgaagaccg acgccgaatt    5280
ggatttgcgc accacgcact cgtcagcac tccgtaggcc gagggcttga tctcctcgat     5340
gtccttgagc gtgacgatga cgactcgtt caccttaagc acattgaact cacctacgtg     5400
gcgcgccggc gaaacgagct tgacgggcgc tcgtacaaaa cagcagaggg agacggcgca    5460
gccagtgttt ttaaagataa aacaaggcac gtggtctgtg cggctctccc agtagctgag    5520
tagatactcg acacaataga ccgtgtctgt cttgagcatg gcgtcgcaca ccgagtaatt    5580
ggggttttta cagatgaggc cggcatcggt gacgcgcagc tcgctgggac ccaacttgag    5640
gatacgccgc gtggcctgca ccagatcctg atggagaacc ttgttcatct ccatcgcacc    5700
```

```
gacgccaccg ccgatttatt tacccggcgc cgactcgtct tttccctcca ggattccgtt    5760
aatgtccatg agcttgctga cgatcgccgt taatagttgc gtcttctcac ggaggatctc    5820
tccgtgactg caggtcgcgc agtcgccgtg cacgtacttg aggaaggcgg cgtacttctg    5880
acccgcgttc acgaaattta agcgcgcgtc cagagagggc agcaacagat cgtagacgcg    5940
cggcagcatc ggctcgaact gtaatagcag atcgtcgtca agatcgggta gcgcgtgtcc    6000
gtcttcaccg tcctcgtcgt caccacctcc cccctcgagc ccaccgctcg taccagccgc    6060
gggctccgcg tcctcgtcga tcaccagcgg tcgcgtcggc accggagaat ccacgtcatc    6120
ctgcacgtcg ttttcctcct ctccgtcgtc atcgtccaga aacggcaccc gctgcttagc    6180
ccaggacatt cttttttccg cgtcctcaat cagcggcgcc gatcgccatg aatccgagta    6240
cccacgtgag cagtaacggc ccaacgactc cccctcacgg gccccacacc acgtttcttc    6300
ccccgaccag cccggccccg tccaccagct ccgtcgccgc cgctaccttg tgcagtccgc    6360
aacgacaggc cgtttcgcgt tacagcggct ggagcaccga gtacacccag tggcactcgg    6420
acttgacaac tgagctgcta tggcacgcgc accgcgtca agtacctatg acgaagcgc     6480 tggccgccgc ggcggccgcc tcataccagg taaatcctca acaccccgcc aaccgttacc    6540
gtcattacga attccagacg ctcagcctcg gcacctcgga ggtagacgaa ctgctcaact    6600
gttgtgcgga agaaaccacg tgcggcggca cgcaatccac cgtactcacc aatgcgacca    6660
acaccactag ctgcggcgga gccgtcgccg gcagtagcaa cgtaggaccc gccggcgctt    6720
cggccgcctg cgacctagat gcagaactgg ccggcctcga aacctcggcg gccgactttg    6780
aacaactgcg gcgactgtgc gcgccgctgg ccatcgacac gcgctgtaac ctatgcgcca    6840
tcatcagcat ctgcctcaaa caggactgcg accagagctg gctcctcgag tacagcttgc    6900
tgtgcttcaa atgcagttac gcgccccgtg cggcgctcag cacgctcatc atcatgtccg    6960
agtttacgca tctgctgcag cagcactttt ccgatctgcg catcgacgac ctgttccgac    7020
accacgttct cacggtcttc gatttccacc tgcactttt catcaatcgt tgctttgaaa     7080
aacaagtggg cgacgcggtt gataacgaga atgtcaccct gaaccatctg gccgtggtgc    7140
gggccatggt catgggtgaa gacacggtgc cttacaacaa gcctcggcgc cacccgcaac    7200
agaagcaaaa aaacaaccct tatcacgtcg aagtgccgca agaactgatc gacaactttc    7260
tagaacacag ctcacctagc cgcgaccgct tcgtgcagct gcttttctat atgtgggccg    7320
gcaccggcgt catgagcacc acgccactca cggaactcac gcacactaag ttcgcgcgac    7380
tagacgcgtt atccacggcc tcggaaagag aagacgcaag gatgatgata gaagaagagg    7440
aggatgaaga aggaggagaa aaaggaggag acgatccggg ccgtcacaac ggcggtggca    7500
ccagcggggg gttcagcgag agcacgctaa aaaaaaacgt gggtcccatt tacctatgtc    7560
ccgtacccgc ttttttttacc aagaaccaaa ccagtaccgt gtgtctgctg tgcgaactca    7620
tggcctgctc ctattacgat aacgtcgtcc tgcgcgagct gtaccgccgc gtcgtctcgt    7680
attgtcagaa caatgtgaag atggtggacc gcattcagct ggtattggcc gatctgttgc    7740
gcgaatgcac gtcgccgctc ggcgcggcac acgaggacgt ggcgcgctgt ggactcgaag    7800
cacccacctc gcccggaggc gactcggact accacggcct gagcggcgtc gacggcgcac    7860
tggcgcgacc cgacccggta ttttgccacg tcctgcgtca ggcaggcgtc acgggcatct    7920
acaagcactt tttctgcgac ccgcagtgcg ccggcaacat ccgcgtcacc aacgaggccg    7980
tgctcttcgg acgcctgcac ccccaccacg tccaggaggt gaaactggcc atctgtcacg    8040
acaattacta tataagtcga cttccgcgac gtgtgtggct ctgcatcaca ctcttcaagg    8100
```

-continued

```
cctttcagat tacaaaacgc acctacaaag gcaaagtgca cctggcggac tttatgcgcg    8160
atttcacgca gctgttggag agttgcgaca tcaagctggt ggaccccacg tacgtgatag    8220
acaagtatgt ctagcgtgag cggcgtgcgc acgccgcgcg aacgacgctc ggccttgcgc    8280
tccctgctcc gcaagcgccg ccaacgcgag ctggccagca aagtggcgtc gacggtgaac    8340
ggcgctacgt cggccaacaa ccacggcgaa ccgccgtcgc cggccgacgc gcgcccgcgc    8400
ctcacgctgc acgacctgca cgacatcttc cgcgagcacc ccgaactgga gctcaagtac    8460
cttaacatga tgaagatggc catcacgggc aaagagtcca tctgcttacc cttcaatttc    8520
cactcgcacc ggcagcacac ctgcctcgac atctcgccgt acggcaacga gcaggtctcg    8580
cgcatcgcct gcacctcgtg cgaggacaac cgcatcctgc ccaccgcctc cgacgccatg    8640
gtggccttca tcaatcagac gtccaacatc atgaaaaata gaaactttta ttacgggttc    8700
tgtaagagca gcgagctact caagctctcc accaaccagc cgcccatctt ccaaatttat    8760
tacctgctgc acgccgccaa ccacgacatc gtgcccttta tgcacgccga ggacggccgg    8820
ttgcacatgc acgtcatctt cgaaaacccc gacgtgcaca tccctgcga ctgcatcacg    8880 cagatgctca cggcggcgcg cgaagactac agcgtcacgc tcaacatcgt gcgcgaccac    8940
gtcgttatca gcgtgctgtg tcacgccgtc tcggccagca gcgtcaagat cgacgtgact    9000
attttgcaac gcaagattga cgagatggac attcccaacg acgtgagcga gtcctttgag    9060
cgctacaaag agctcattca ggagctgtgt cagtccagcg gcaacaacct atacgaggag    9120
gccacgtcgt cctacgcgat acggtctccc ttaaccgcgt cgccgttgca cgtagtttcc    9180
accaacggct gcggcccctc ctcctcgtcc cagtccacgc cgcctcatct ccacccgccg    9240
tcgcaggcga cgcagcccca ccactactct caccaccagt ctcagtctca gcagcatcat    9300
caccgtcccc agtcaccacc gccgccgctg tttctcaaca gcattcgtgc gccttgacac    9360
tgtacggcag aaaagccggc tccaagtgca agcgccgcgg cagcaccatg tgcaaaaact    9420
tgtccttgcg cgcggtttcg ccgccgggaa agacgggcga cagcacgtta gttacagcct    9480
tgagaacctg ctcaaagtac ttgtcggcgt gaatgggcac gccgtgctcg cgcacgtagc    9540
tcggatcttc ggctacctcg tagttgcaca cggccgacgg tggtttccgc gccctcttct    9600
ttgccggctc tcctcctctc ctgttgctct cctctacccc gccgccgtca gcgtcgtcgt    9660
ccgtgccatc aatcgcgtcc gaccgggaaa ccacgccggc ggttacagaa tcaccgttgt    9720
cggaggaacc ctgcggcgcc gtccggacac cgggcgccgt cagaacgtaa aagacccgat    9780
ccccgaccga gggtagctcc tcagaacggg ccgccaatcg cttaatgacg gcaatgtgcg    9840
gcaggttaga ttgacggtac agcgagatgt ccttagagag caccgacgaa agcaccaggt    9900
cctcgacacg cacacggtgc aggtacagat cgtcgcgggc ctgcaccaag cggcgtaaga    9960
tacgccagaa accgcgtggc acgccgtact tcttgacttc atcgagtgag aggcgcgaca    10020
ggcgcacggc tgcttccgag acctcgcgat cctcaaagag cagcgagagg acgtcacgcg    10080
tgacgccctt gacgaactcg caggccgtct tgcgcaccag atccacgccc ttcatgctca    10140
gacccgaggc gccctccact tgccgatgt aacgtttctt gcagatcatc ataagagaga    10200
cgaagacctt tcaaaactcc agcttgacgg gctccacaaa aagacaggcc gtcacgtagt    10260
gcgccaggct gggcccacgc gccaccagag cctgcggcgt caggccacga aagcggacaa    10320
acacgctgtc cgtgtccccg tagatgaccg gcgcctccac ccgccgttcg ttcgagcccc    10380
ctgacgatgt ttcgagcccc tccggtaacg cgctgctctc ctccgaatcc ccctcccgcg    10440
```

-continued

```
ttcccactac atagtcttcc tgattaaaaa aattgtgcaa aaaacacggc tctgaaaagt    10500
tgtctttgat gaaccgcgcc gtgcgctcta gcatgtcgcg accgatgcgc gtgatgctgg    10560
cggcgatggg cagacacggc atcataccgt tgaccacgcc ggtaaaaccg tagaaagcgt    10620
tgcacgttac tttgagcgcc atctgttcct tgtcgagcag catacggcgc acagggtctt    10680
gacactcgcg catgcattcg cgcacggcac gccgctgcga aacccacttg ttgagcagtt    10740
ccgagagcac cgagacgcgc accgaagcac gcacaaagcg gtgggtcacg ccgttctcta    10800
gcgtgacgct gtatacgtcg gcggggtcca cagggtactc gccacccggc accagcaggg    10860
tggagtagca gaggttgtgg gccatgatga tggaagggta gaggctggca aagtcgaaca    10920
cggccacggg gtcgttgtag taacccacct cgggctcaaa caccgtggcg ccctggtacg    10980
aaaccgccgc agtaccgccg cgccgtgat tgtcgttgga aacgccgacg ccgccactac    11040
tgccggagcc gacgctgaaa acgccgacgc tgctactact gttactgccg gagccgggtg    11100
aaacgccgtc ctgactggac ggcgcagatt gcaagggcgg cgacatctga acatagccg    11160
ccacagaacc cgcgtcgccg ggcacagcgg cggtagagat gatagcagcg ttaggtgaca    11220
cagcaacgct attcgtttcg ggcaccgtcg tacctttgct gtagtggttg ggcaggataa    11280
aatcgcggca ggcgcactcg tccagcagcg aggtgtagat acggatctgc tgtccgtcaa    11340
agatgacacg ccgcaacgga attttagcca gccgcgcgat ggccccggcc tcgtagtgaa    11400
aattaatggt gttgaacaga tcgcgcacca atacggcgtc ctgcagacag taacggccta    11460
cctgggcgcg gccctcggca ttagccacga acaacgcgg gatgtccttg taagacaggt    11520
catccttgcg ttgccgcagg taaagctcgg ccatagtgtt gagcttatag ttgggcgagt    11580
tagtcttggc catgcataca gggtacatgt cgataaccac cgaacccgca atatacacct    11640
tggtggcggc cgtgctggcc ggattgttgt gagaagccga gggaaaagcg gcggcgtact    11700
gccgcttaaa acccacggcg gggctgtgta aaaagaaacg gccgccctgc gccgtaggca    11760
acttgcagaa gcgctgcgag tccaccttat acaggtactc gagacgcgtg aggatgtact    11820
tcaagtcaaa agagttgatg ttgtaaccgg tcacaaaggc cggcgcgtac cgttgaaaga    11880
aaagcataaa gcccagcagc agctcgtatt cggaagggaa ctcgtagacg tccacgtctg    11940
ggcccacctg cccgcaggtg ccgatcgtaa agagatgaag acccgagtgc caaagatca    12000
caccctccga agtgcagccc cgaccatcgt tcccgtttgg gatccctga tccacggcgg    12060
tgtttccccc cgtctcgtag cacacgcacg agatctgaat gacaatgtca tcggacttct    12120
cggcgcaggg aaaaccaccc tcgccgctca tgcactcgat atcgaaggac aggcatcgat    12180
agcgcggcca cgagctgtcg tcgggcacag ccaccaggtc agagacatcg cagtctacct    12240
cgatatcaca agtcgacgcg cgaccctgct gccgccagtc gtaacgattc acggagcacc    12300
agccgaacgt ggtgatccgc cgatcgatga ccaaacgcgt cagcggatcc acacggacct    12360
cgtacacggg aaaaccctgc tccagcagat actcgccgat ttttctggcc atggtccagt    12420
tgctgataga cacacactgc aaatcgggca cgggtcgcgt cccgtaccca tagatggagg    12480
tcttggtggc cggcgtgaca gacacggcgt atggcgtccg cggttcgggc actagttcgc    12540
ccacgctggc aatgacctca cgcagcctat cggtgtcgct gtactcacag taaaagtagc    12600
tgcgctgccc gaaaacgttg acgcagatac tgtagccgtg ttctgtgcc ccgaagaaac    12660
gcaacacgtt ccccgaaggc accagatgct gacgatagcg cggcgacacg ttttcgggcg    12720
agtcgaagaa gagcacggcg tccgtctgat cgtaggtgtg aaaacgaata ggtcccacca    12780
cgcgacccac cagggtctcg cgccaaggac acggccaaac catgtcatga ctcaacaaat    12840
```

-continued

```
gtttaatctc tcgatagaac atgagaggca gccgtcccgt cttatgcttg atcaaccccg    12900
tctgaccgtc gaacatgaca cctcgcggca cgatctgcaa aaactgtttc tgtggcggcc    12960
gcttgcccga gccctgcgcg gagccgggct gcgaacgctg acgccggcca cccgcgaccg    13020
caccgccggt cacgccgccg ctcagatacg ggttgaaaaa catagcggac cgtgagaggc    13080
tgacagctta cgaagcaaaa tcacaaagaa aatacacatg cagcacctag atatccagtt    13140 taacccccgta tatcacaagt ctctgtgtca atatttttttg tctagttttt ttttcctcct   13200
ggttcagacg ttctcttctt cgtcggagtc tttcaagtgt ctgtagccgt ttttgcgatg    13260
tcgcagccgg tctagcaggt taggcttctg tcccttgtcc tgcgtgccag tctgtccgtc    13320
caaagaatct gtaccgttct gctgcgctcg ctgctctgcg tccagacggg ccagggccag    13380
aagcatctgg taagcctgct cgttggtgta aggcggagcc gccgtggatg catcagacga    13440
cggtggtccc ggtcctttgc gaccagaatt ataaacactt tcctcgtagg aaggcggagc    13500
ctgtaacgac gtgtctttgg tgctgcccga cgtcacggtg gtcccgtcgg cggacaccag    13560 ataggggaaag aggttctgca gcggctgcgt gcacagacgc cgctgtcgag tatagatcaa    13620
ataagtgata atgactacgg ctatggccac gaggatgatg gtgaaggctc cgaagggggtt   13680 tttgaggaag gtggcaacgc cttcgaccac ggaggccacc gcgccaccca cggcccccaat   13740 ggctacgcca acggcctttc ccgcggcgcc caggccgctc atgaggtcgt ccagacccct    13800
gaggtagggc ggtagcgggt cgactaccct gtcctccacg tactttaccc gctgcttgta    13860
cgagttgaat tcgcgcatga tctcttcgag gtcaaaaacg ttgctggaac gcagctcttt    13920
ctgcgagtaa agttccagta ccctgaagtc ggtatttttcc agcgggtcga tatccagggc    13980
gatcatgctg tcgacggtgg agatactgct gaggtcaatc atgcgtttga agaggtagtc    14040
cacgtactcg taggccgagt tcccggcgat gaagatct                            14078
```

<210> SEQ ID NO 30
<211> LENGTH: 4569
<212> TYPE: DNA
<213> ORGANISM: Human cytomegalovirus

<400> SEQUENCE: 30

```
agatcacgat acagccggcg gtatcgataa tcttgttgcg gtactggatg gtaaagtcgg      60
gctcgggctt gatgtcttcc tgtttgatga ggggcagcat gataggcgcg ggaggcacgg     120
gcggtttaat aatcaccttg aaaggacgcg tggttttgcg cggtttctta cgcgggctga    180
gctcgggagt agcggatgcc ccggggagag gagtgttagt aaccgcgacg ctggtggggg    240
tcggcttgtt aagagggggcg ctgctaacgc tgcaagagtg ggttgtcagc gtggggccgg    300
tgctactgga atcgataccg gcatgattga cagcctgggc gaggatgtca cctgatggtg    360
ataagaagac acgggagact tagtacggtt tcacaggcgt gacacgtttta ttgagtagga    420 ttacagagta taacatagag tataatatag agtatacaat agtgacgtgg gatccataac    480
agtaactgat atatatatac aatagtttac tggtcagcct tgcttctagt caccataggg    540
tgggtgctct tgcctccaga ggcggtgggt tcctcagcac catcctcctc ttcctctggg    600
gcaacttcct ctatctcaga cactggctca gacttgacag acacagtgtc ctcccgctcc    660
tcctgagcac cctcctcctc ttcctcatca ctctgctcac tttcttcctg atcactgttc    720
tcagccacaa ttactgagga cagagggata gtcgcgggta caggggactc tgggggtgac    780
accagagaat cagaggagct gacaccagcg gtggccaaag tgtaggctac aatagcctct    840
```

-continued

```
tcctcatctg actcctcggc gatggcccgt aggtcatcca cactaggaga gcagactctc    900
agaggatcgg cccccagaat gtactgggca aagaccttca tgcagatctc ctcaatgcgg    960
cgcttcatta cactgataac ctcaggcttg gttatcagag gccgcttggc cagcatcaca   1020
ctagtctcct ctaagacata gcagcacagc acccgacaga actcacttaa gagagagatg   1080
cccccgtaca tggtcatcat acaagcgtca ctagtgacct tgtactcatt acacattgtt   1140
tccacacatg tagtgaggat atccataaat atgtgatcaa tgtgcgtgag caccttgtct   1200
ctctcctcat ccaaaatctt aaatattttc tgggcataag ccataatctc atcagggagg   1260
cactgaggca agttctgcag tgccgccatg gcctgactgc agccattggt ggtcttaggg   1320
aaggctgagt tcttggtaaa gaactctata ttcctgtagc acatatacat catctttctc   1380
ctaagttcat cctttttagc acgggcctta gcctgcagtg cacccccaa cttgttagcg   1440
gcgcccttgc tcacatcatg cagctcctta atacaagcca tccacatctc ccgcttatcc   1500
tcaggtacaa tgtagttctc atacatgctc tgcatagtta gcccaataca cttcatctcc   1560
tcgaaaggct catgaacctt atctaagata tctaaggcat tctgcaaaca tcctcccatc   1620
atattaaagg cgccagtgaa tttctcttcc gtctgggtat attttttcag catgtgctcc   1680
ttgattctat gccgcaccat gtccactcga accttaatct gtttgactgt agaggaggat   1740
aacaacacat ataagtatcc gtcctcctga ctcatttatc gctatctcga tgccccgctc   1800
acatgcaaga gttaatcttt actctatctg acatacacaa gtaaatccac gtcccatgca   1860
ggttagtata catcacatac atgtcaacag acttaccgag ttctgccagg acatctttct   1920
cggggttctc gttgcaatcc tcggtcactt gttcaaaagt tttgagggat tcttcggcca   1980
actctggaaa cagcgggtct cccagactca gctgactgtt aacctccttc ctcaacatag   2040
tctgcaggaa cgtcgtggcc ttggtcacgg gtgtctcggg cctaaacaca tgagaaatag   2100
agtcataagc acatgggtca catacaggag atatgtatat aacattaata caattttatt   2160
aaaaaaaaag gggggcaca aaccccgaca cgtaccgtgg caccttggag aagggccct    2220
cgtcaggatt atcagggtcc atctttctct tggcagagga ctccatcgtg tcaaggacgg   2280
tgactgcaga aaagacccat ggaaaggaac agtctgttag tctgtcagct attatgtctg   2340
gtggcgcgcg cggcagcaac gagtactgct cagactacac tgccctccac cgttaacagc   2400
accgcaacgg gagttacctc tgactcttat cagaacacaa caactcagct gcctgcatct   2460
tcttctgccg ctgccttaag tcttccaaat gcgtcagcgg tgcaagcccg ctcccccgagc  2520
tcattttcag acacataccc taccgccacg gccttgtgcg gcacactggt ggtggtgggc   2580
atcgtgctgt gcctaagtct ggcctccact gttaggagca aggagctgcc gagcgaccat   2640
gagtcgctgg aggcatggga gcagggctcg gatgtagaag ctccgccgct accggagaag   2700
agcccatgtc cggaacacgt acccgagatt cgcgtggaga tcccacgtta tgtttaataa   2760
aaactgcggg cactggggac ggtggtgttg tatatgtgaa tttgtaaata ataaatgaga   2820
ccccatcctg taaaaataca gagtccgtgt cagtctctga aggacagtgt attggcatat   2880
agccaataaa gagagttgtg gcaaagagcc atgttatgga ttagtaatgg aaagtatcgt   2940
caccaatagg ggagtggtca ataatggtca ataacccaca cctataggct aagctatacc   3000
atcacctata acatgaggaa gcgggggtgt atagacccca agccaaaaac agtatagcat   3060
gcataagaag ccaagggggt gggcctatag actctatagg cggtacttac gtcactcttg   3120
gcacggggaa tccgcgttcc aatgcaccgt tccggccgc ggaggctgga tcggtcccgg   3180
tgtcttctat ggaggtcaaa acagcgtgga tggcgtctcc aggcgatctg acggttcact   3240
```

-continued

```
aaacgagctc tgcttatata gacctcccac cgtacacgcc taccgcccat ttgcgtcaat    3300
ggggcggagt tgttacgaca ttttggaaag tcccgttgat tttggtgcca aaacaaactc    3360
ccattgacgt caatgggtg gagacttgga atccccgtg agtcaaaccg ctatccacgc      3420
ccattgatgt actgccaaaa ccgcatcacc atggtaatag cgatgactaa tacgtagatg    3480
tactgccaag taggaaagtc ccataaggtc atgtactggg cataatgcca ggcgggccat    3540
ttaccgtcat tgacgtcaat aggggcgta cttggcatat gatacacttg atgtactgcc    3600
aagtgggcag tttaccgtaa atactccacc cattgacgtc aatggaaagt ccctattggc    3660
gttactatgg gaacatacgt cattattgac gtcaatgggc ggggtcgtt gggcggtcag    3720 ccaggcgggc catttaccgt aagttatgta acgcggaact ccatatatgg gctatgaact    3780
aatgaccccg taattgatta ctattaataa ctagtcaata atcaatgtca acatggcggt    3840
aatgttggac atgagccaat ataaatgtac atattatgat atggatacaa cgtatgcaat    3900
ggccaatagc caatattgat ttatgctata taaccaatga ataatatggc taatggccaa    3960
tattgattca atgtatagat cgatatgcat tggccatgtg ccagcttgat gtcgcctcta    4020
tcggcgatat agcctcatat cgtctgtcac ctatatcgaa actgcgatat ttgcgacaca    4080
cagaatcgcc caagtcacca aagtcgtcta tcgccatccc ccgtaaacga tataagcgct    4140
atcgccagat atcgcgtatg cccaaaaatc acttttggaa aaatggcgat atcagttaca    4200
cagaaactca catcgcgac attttcaata tgccatattt tcaaatatcg attttttccaa    4260 tatcgccatc tctatcggcg ataaacacca ctatcgcgcg acatgaattt agtcggcgac    4320
agaaatctca aaacgcgtat ttcggacaaa cacacatttt attattcact gcagcatata    4380 gcccattta gcgcggcaca catccagccg tttgtgtttt ttaacgctct ccaggtactg    4440
atccaggccc acgatccggg ttatcttgtc gtattccagg ttgatccatc gatagggaac    4500
gctgccagcg gcgcccagca ggtactgcgc cttgtcgttc actttgccgc agcgtattcg    4560
cccgtcagc                                                            4569
```

<210> SEQ ID NO 31
<211> LENGTH: 2666
<212> TYPE: DNA
<213> ORGANISM: Human cytomegalovirus

<400> SEQUENCE: 31

```
agatcgtgct tccctcttcc aaggatcgga aagtagcgtc cgtcgtttcc gcggacgcgg     60
cttccctggt acgctccgtt tccgacgacg cggtttcccg ctgcgtggaa actgtctcca    120
tgtcgggacc gcagcgcccg gcggcgtatc cgcaaggtct cgaagctaca gcttgtcaga    180
ggaaaagtag gtttgcaaaa aggtgcgcag ggtcatgatt ctcagcacca tcagcagagt    240
gaaaaccaga ctgagaaaca ccttgacggc cgccaaaagc gcgcgttcca gcggcgtctc    300
gtagcgtaca gccagggccg cttcgtggaa atgcgagacg gctagacagg taatgagcac    360
gctgaaggac aagacgatct taaagcacca ggaccaacca cgcctcaaga tgaccaccac    420
gattgccgtg aaggtcaacg tgatcaaagc atggacgacc acgatctgac ggcggacggt    480
acgttcggga gccaacaacg ctacgccggt gcagctgaga aggccagta aggtgaacaa    540 cgcggccgag atgaccaacg taccgtccag gcagagacat atcacgatca acggcggcac    600
gtgaagcagc gtgtaaaaga gcagaacgcc gatattgctg ggatgcgatg tttcgtaaca    660
gtgaatgaag atcactgacg tgacgggtat gacaaagacg aggctgggcg aggactccgt    720
```

-continued

```
gagacacaga cgagaatggt gaaaccacgt cgcgggcgcc gcgtagcaga aggcgctcaa      780
caacgcggtc aagccggcca gctgccaacc cacggcgcca taggtgtgca gcgccacgcg      840
gcaacagtcg acccaagcca gactgcgggt cgccagccgg gtctcttgga tcccggggg      900 cacgtagatg accgtgccat cggtgggtac ttgaaaccct ttttctcttc tcatggtgcg      960
ctgcgttctc tggaaacggc tgctctgtcc gaaaaccagt tccgaacgaa aatctagggc     1020
gagagggtgg acaacggcgt cgacgacgaa gcatgggaca ggtcgttcgg cgttaacgtc     1080
atcgcgtcgg acgacggtag ttctaagaga cgtagatcgc tcagcaggtc ctgacagttg     1140
cggattcgca agatcagaaa aaaaaggaa atgaacgtaa taaagagctg tagcgacgta     1200
tgcgccacat cgcgtggcat aagaacgtga cggacgaaaa ggacctgctg cgaaaagtga     1260
ccggcgaaga taaggcccac cgtgctgtag aagcccaaaa gcagccgcag gggccaagtc     1320
cagggccgcg tgaagacgat gagaacgttg accagaaaga ccacgaccca gacgccgttg     1380
atgagggtaa attgatcgga cagggtgcag ttgtcgcgac agatgaagac tacttccgcg     1440
cagagcaagg tgatgaccaa cgtgagcaca aacgacgtca cacctcgcg gggctcctgg     1500 caggcacacg tgacacctag cgccgggatg tgcgccagga ggccggcgag taatagcacc     1560
agctgtcgga acggacgacg gcagcgcggg tgccggtttc gctgagcgag aaccggtcgc     1620
tcatagcgga aatacacgaa gagcgcggag gccacaggca ccaggaggag cacctcgggc     1680
gcccagacaa cgtgacaagg aaagcccgga cgcgacttga gagtcgctgt agggaagacc     1740
agagagaagc tacccaagac ggccaccgcc gcggagattt ggaagaggag caagccggcg     1800
attcggacga caacctcgaa gcgatgcacc cagcccagca cggccaccac ggccgcttca     1860
tcatagtcgt cgttgttgcc gctgtcgaac agccgccgaa acacgatctg tcgctgggtc     1920
gcggtgggaa agcgcagacc catgacagcc ggaggctata tgaccgcgcg tctaagacgc     1980
gagatccgtg gggggacttt tagatgtttg ggcggcccgc ggttctaaca ggcttgattg     2040
gtggagacgg ccggcgcggc gggtggggga aacgacgagt ttttccgtta cgccatggtt     2100
cgcgtgaggt ttctctgtac ctcccgcaaa aggtcacagc ccgaaatgga ggccgcgttg     2160
gtggccccgg tggcgcgtga cgataaccag gtcatccaag cgatgagttt gtctaatgag     2220
tcctcggtgg tgaagaggat gagaatgagc aggtacaggt acaccaggtt ctcatagaga     2280
cacaaggtga gcaggtcagc ctcggaccac gcgatctcaa acaggcgcgt ggtgtcaaag     2340
accgtgacga ccagcatgaa gctgagcgcc atggcgtaat agcccaaaaa aagtttgtgc     2400
cccaacggta cgggctgcag gtaaagtgcg atcaagaacg cgataacgcc gatcacaaac     2460
agcgtgacga tgacctgcca tcgacggtga ttatggccgg ctagacccgt gacgcagctg     2520
cagaggctaa aaagcacgca agccaagagg cccgagaagg tcactagcgt agaggaggag     2580
caggcgctgg ccacgatcac cgaaagcgtc gtgagcacgc tataaatggt gagcaggcca     2640
gggctcggtg gcgacgtgaa cgatcc                                         2666
```